(12) United States Patent
Schildroth et al.

(10) Patent No.: US 10,028,426 B2
(45) Date of Patent: Jul. 24, 2018

(54) AGRONOMIC SYSTEMS, METHODS AND APPARATUSES

(71) Applicant: 360 YIELD CENTER, LLC, Morton, IL (US)

(72) Inventors: Rhett Schildroth, North Liberty, IA (US); Daryl B. Starr, Lafayette, IN (US)

(73) Assignee: 360 YIELD CENTER, LLC, Morton, IL (US)

( * ) Notice: Subject to any disclaimer, the term of this patent is extended or adjusted under 35 U.S.C. 154(b) by 0 days.

(21) Appl. No.: 15/099,793

(22) Filed: Apr. 15, 2016

(65) Prior Publication Data

US 2016/0302351 A1      Oct. 20, 2016

Related U.S. Application Data

(60) Provisional application No. 62/149,211, filed on Apr. 17, 2015.

(51) Int. Cl.
*A01B 79/00* (2006.01)
*B64C 39/02* (2006.01)
(Continued)

(52) U.S. Cl.
CPC .......... *A01B 79/005* (2013.01); *B64C 39/024* (2013.01); *H04L 67/12* (2013.01);
(Continued)

(58) Field of Classification Search
CPC ..... A01B 79/005; B64C 39/024; H04L 67/12; G01N 21/3554; G01N 21/55; G01N 2201/0216
See application file for complete search history.

(56) References Cited

U.S. PATENT DOCUMENTS 4,265,076 A    5/1981 Krutz
RE31,023 E    9/1982 Hall, III
(Continued)

FOREIGN PATENT DOCUMENTS

GB    2513976 A    11/2014
JP    H0899070 A    4/1996
(Continued)

OTHER PUBLICATIONS

International Search Report and Written Opinion for PCT/US15/37435 dated Nov. 20, 2015, 29 pages.
(Continued)

*Primary Examiner* — Calvin Cheung
(74) *Attorney, Agent, or Firm* — Klintworth & Rozenblat IP LLP

(57) ABSTRACT

In one aspect, an agricultural system is provided and includes an information gathering component, a first component and a second component. The information gathering component is configured to gather information pertaining to at least one agricultural characteristic and generate agricultural data associated with the gathered information. The agricultural data is transmitted over a network and used to generate an agricultural prescription, which is comprised of at least one agricultural characteristic and at least one agricultural action. The first component includes a network interface for receiving the agricultural prescription over the network and the second component is in communication with the first component. The second component is configured to receive the agricultural prescription from the first component and is configured to output the at least one agricultural action.

29 Claims, 48 Drawing Sheets

(51) Int. Cl.
*H04L 29/08* (2006.01)
*G01N 21/55* (2014.01)
*G01N 21/3554* (2014.01)

(52) U.S. Cl.
CPC ......... *G01N 21/3554* (2013.01); *G01N 21/55* (2013.01); *G01N 2201/0216* (2013.01)

(56) References Cited

U.S. PATENT DOCUMENTS

| | | | |
|---|---|---|---|
| 4,630,773 | A | 12/1986 | Ortlip |
| 5,220,876 | A | 6/1993 | Monson et al. |
| 5,467,271 | A | 11/1995 | Abel et al. |
| 5,585,626 | A | 12/1996 | Beck et al. |
| 5,668,719 | A | 9/1997 | Bobrov et al. |
| 5,789,741 | A | 8/1998 | Kinter et al. |
| 5,884,224 | A * | 3/1999 | McNabb ............... A01G 7/00 700/284 |
| 5,897,619 | A | 4/1999 | Hargrove, Jr. et al. |
| 6,058,351 | A | 5/2000 | McCauley |
| 6,070,539 | A | 6/2000 | Flamme et al. |
| 6,119,069 | A | 9/2000 | McCauley |
| 6,505,146 | B1 | 1/2003 | Blackmer |
| 6,549,852 | B2 | 4/2003 | Hanson |
| 6,597,991 | B1 | 7/2003 | Meron et al. |
| 6,606,542 | B2 | 8/2003 | Hauwiller et al. |
| 6,745,128 | B2 | 6/2004 | Hanson |
| 6,792,882 | B2 | 9/2004 | Aspelin et al. |
| 6,889,620 | B2 | 5/2005 | Fraisse et al. |
| 6,990,459 | B2 | 1/2006 | Schneider |
| 6,999,877 | B1 | 2/2006 | Dyer et al. |
| 7,047,133 | B1 | 5/2006 | Dyer et al. |
| 7,047,135 | B2 | 5/2006 | Dyer et al. |
| 7,081,611 | B2 | 7/2006 | Scott |
| 7,167,187 | B2 | 1/2007 | Scott et al. |
| 7,167,800 | B2 | 1/2007 | Faivre et al. |
| 7,171,912 | B2 | 2/2007 | Fraisse et al. |
| 7,184,892 | B1 | 2/2007 | Dyer et al. |
| 7,313,478 | B1 | 12/2007 | Anderson et al. |
| 7,343,867 | B2 | 3/2008 | Fraisse et al. |
| 7,412,330 | B2 | 8/2008 | Spicer et al. |
| 7,440,901 | B1 * | 10/2008 | Dlott ............... G06Q 10/06393 235/375 |
| 7,702,597 | B2 | 4/2010 | Singh et al. |
| 7,723,660 | B2 | 5/2010 | Holland |
| 7,848,865 | B2 | 12/2010 | Di Federico et al. |
| 7,930,085 | B2 | 4/2011 | Anderson et al. |
| 7,991,754 | B2 | 8/2011 | Maizel et al. |
| 8,032,389 | B2 | 10/2011 | Avey et al. |
| 8,046,280 | B2 | 10/2011 | Avey et al. |
| 8,050,876 | B2 | 11/2011 | Feen et al. |
| 8,098,894 | B2 | 1/2012 | Soderstrom |
| 8,150,554 | B2 | 4/2012 | Anderson |
| 8,249,926 | B2 | 8/2012 | Avey et al. |
| 8,290,795 | B2 | 10/2012 | Avey et al. |
| 8,306,750 | B2 | 11/2012 | Grifin |
| 8,319,165 | B2 | 11/2012 | Holland |
| 8,335,653 | B2 | 12/2012 | Pruett et al. |
| 8,412,419 | B1 * | 4/2013 | Seamon ............... A01B 79/005 700/283 |
| 8,417,534 | B2 | 4/2013 | Belzer et al. |
| 8,417,602 | B2 | 4/2013 | Avey et al. |
| 8,437,879 | B2 | 5/2013 | Anderson |
| 8,489,437 | B1 | 7/2013 | Dlott et al. |
| 8,521,372 | B2 | 8/2013 | Hunt et al. |
| 8,558,157 | B2 | 10/2013 | Holland |
| 8,643,495 | B2 | 2/2014 | Lan et al. |
| 8,671,006 | B2 | 3/2014 | Zyskowski et al. |
| 8,816,262 | B2 | 8/2014 | Holland |
| 8,863,012 | B2 * | 10/2014 | Nara ............... A01C 21/007 702/5 |
| 8,924,030 | B2 | 12/2014 | Wendte et al. |
| 9,008,409 | B2 | 4/2015 | Hausmann et al. |
| 9,516,802 | B2 * | 12/2016 | Zemenchik ............ A01B 71/02 |
| 2002/0059091 | A1 | 5/2002 | Hay et al. |
| 2003/0070103 | A1 | 4/2003 | Kim |
| 2006/0074560 | A1 | 4/2006 | Dyer |
| 2007/0186830 | A1 * | 8/2007 | Fraisse ............... A01B 49/06 111/200 |
| 2009/0112637 | A1 * | 4/2009 | Avey ............... A01B 79/005 705/4 |
| 2009/0177330 | A1 | 7/2009 | Kah, Jr. |
| 2009/0259483 | A1 * | 10/2009 | Hendrickson .......... G06Q 10/06 705/315 |
| 2011/0301755 | A1 | 12/2011 | Anderson |
| 2011/0320229 | A1 * | 12/2011 | Stehling ............. G06Q 10/0631 705/7.12 |
| 2012/0101634 | A1 | 4/2012 | Lindores |
| 2012/0101796 | A1 | 4/2012 | Lindores |
| 2012/0101861 | A1 | 4/2012 | Lindores |
| 2012/0123817 | A1 * | 5/2012 | Hohenberger ...... G06Q 10/0631 705/7.12 |
| 2012/0310679 | A1 | 12/2012 | Olson et al. |
| 2013/0018586 | A1 | 1/2013 | Peterson et al. |
| 2013/0066666 | A1 | 3/2013 | Anderson, Jr. et al. |
| 2013/0160164 | A1 | 6/2013 | He et al. |
| 2013/0185104 | A1 | 7/2013 | Klavins |
| 2013/0231968 | A1 | 9/2013 | Willness |
| 2013/0232642 | A1 | 9/2013 | Allen et al. |
| 2013/0255783 | A1 | 10/2013 | Runge et al. |
| 2013/0318867 | A1 | 12/2013 | Skinner |
| 2014/0012732 | A1 | 1/2014 | Lindores |
| 2014/0035752 | A1 | 2/2014 | Johnson |
| 2014/0067745 | A1 * | 3/2014 | Avey ........................ G06N 5/02 706/46 |
| 2014/0089045 | A1 | 3/2014 | Johnson |
| 2014/0108280 | A1 | 4/2014 | Dlott et al. |
| 2014/0285673 | A1 | 9/2014 | Hundley et al. |
| 2014/0299749 | A1 | 10/2014 | Zielke et al. |
| 2014/0311014 | A1 | 10/2014 | Feugier |
| 2014/0312165 | A1 | 10/2014 | Mkrtchyan |
| 2014/0316692 | A1 | 10/2014 | Hillger et al. |
| 2014/0321714 | A1 | 10/2014 | Masten |
| 2014/0324490 | A1 | 10/2014 | Gurin |
| 2014/0326801 | A1 | 11/2014 | Upadhyaya et al. |
| 2014/0358381 | A1 | 12/2014 | Holland |
| 2015/0027040 | A1 | 1/2015 | Redden |
| 2015/0032273 | A1 | 1/2015 | Romney et al. |
| 2015/0040473 | A1 * | 2/2015 | Lankford ............... A01G 1/001 47/58.1 SC |
| 2015/0061888 | A1 | 3/2015 | Lankford et al. |
| 2015/0073716 | A1 | 3/2015 | Johnson |
| 2015/0075068 | A1 | 3/2015 | Stowe et al. |
| 2015/0081058 | A1 | 3/2015 | Oliver et al. |
| 2015/0105984 | A1 * | 4/2015 | Birrell .................. A01D 41/127 701/50 |
| 2015/0106141 | A1 | 4/2015 | Klavins |
| 2016/0125331 | A1 * | 5/2016 | Vollmar ............ G06Q 10/06311 705/7.13 |
| 2017/0061052 | A1 * | 3/2017 | Gates .................... A01G 25/167 |
| 2017/0228118 | A1 * | 8/2017 | Sugumaran ........... G06F 3/0484 |
| 2018/0103596 | A1 | 4/2018 | Ozawa |

FOREIGN PATENT DOCUMENTS

| | | |
|---|---|---|
| WO | 2013101806 A1 | 7/2013 |
| WO | 2013169349 A1 | 11/2013 |
| WO | 2014026183 | 2/2014 |
| WO | 2014105852 A1 | 7/2014 |
| WO | 2014186810 A1 | 11/2014 |
| WO | 2014203664 A1 | 12/2014 |
| WO | 2015013723 A2 | 1/2015 |
| WO | 2015051339 A1 | 4/2015 |

OTHER PUBLICATIONS

International Search Report and Written Opinion for PCT /US2016/024096 dated Jun. 10, 2016, 18 pages.
Partial Supplementary European Search Report for European Patent Application No. 15811981.8 dated Nov. 20, 2017, 7 pages.

* cited by examiner

SHREDDING OR COLLECTING?

FIELD PROJECTIONS WORKSHEET

Field (Sloped) 163.75 Acres
Solver Advantage: 50 bpa   What is solver?

Seed: AAS Generic Seeds - Brand X 108
Planting Date: 04/23/2015
Forecast: NW Indiana Norm

| Zone | Seeding Rate | Projected Yield | Limiting Factor | 03/20/2015 | Planting |
|---|---|---|---|---|---|
| Average | 32 | 170.8 bpa | Nitrogen | 150N | 30N |
| 26.99 ac / RevA / 0 | 32 | 193.2 bpa | Nitrogen | 150N | 30N |
| 19.73 ac / WmiA / 0 | 32 | 190.2 bpa | Nitrogen | 150N | 30N |
| 8.04 ac / WmiA / 0 | 32 | 190.2 bpa | Nitrogen | 150N | 30N |
| 7.59 ac / MouA / 0 | 32 | 213.3 bpa | Nitrogen | 150N | 30N |
| 5.00 ac / BstA / 0 | 32 | 130.1 bpa | Nitrogen | 150N | 30N |
| Show all zones... | | | | | |
| Average | 32 | 170.8 bpa | Nitrogen | 150N | 30N |

*FIG. 20*

FIELD PROJECTIONS WORKSHEET

Field (Sloped) 163.75 Acres    What is solver?
Solver Advantage: 23 bpa

Seed: AAS Generic Seeds - Brand X 108
Planting Date: 04/23/2015
Forecast: NW Indiana Norm

| Zone | Seeding Rate | Projected Yield | Limiting Factor | Planting | V4 |
|---|---|---|---|---|---|
| Average | 32 | 173.8 bpa | Nitrogen | 30N | 150N |
| 26.99 ac / RevA / 0 | 32 | 213.4 bpa | Seed | 30N | 150N |
| 19.73 ac / WmiA / 0 | 32 | 213.4 bpa | Seed | 30N | 150N |
| 8.04 ac / WmiA / 0 | 32 | 213.4 bpa | Seed | 30N | 150N |
| 7.59 ac / MouA / 0 | 32 | 213.4 bpa | Seed | 30N | 150N |
| 5.00 ac / BstA / 0 | 32 | 90.2 bpa | Nitrogen | 30N | 150N |
| Show all zones... | | | | | |
| Average | 32 | 173.8 bpa | Nitrogen | 30N | 150N |

*FIG. 21*

FIELD PROJECTIONS WORKSHEET

Field (Sloped) 163.75 Acres  
Solver Advantage: 3 bpa  ✎ What is solver? ✨

Seed: AAS Generic Seeds - Brand X 108 ✎  
Planting Date: 04/23/2015 ✎  
Forecast: NW Indiana Norm ✎

| Zone | ✨ Seeding Rate ✨ | Projected Yield ✨ | Limiting Factor | Planting | ✨ V8 | ✨ |
|---|---|---|---|---|---|---|
| Average | 32 ✎ | 194.0 bpa | Nitrogen | 30N ✎ | 150N ✎ | |
| 26.99 ac / RevA / 0 | 32 ✎ | 213.4 bpa | Seed | 30N ✎ | 150N ✎ | |
| 19.73 ac / WmiA / 0 | 32 ✎ | 213.4 bpa | Seed | 30N ✎ | 150N ✎ | |
| 8.04 ac / WmiA / 0 | 32 ✎ | 213.4 bpa | Seed | 30N ✎ | 150N ✎ | |
| 7.59 ac / MouA / 0 | 32 ✎ | 213.4 bpa | Seed | 30N ✎ | 150N ✎ | |
| 5.00 ac / BstA / 0 | 32 ✎ | 148.3 bpa | Nitrogen | 30N ✎ | 150N ✎ | |
| Show all zones... | | | | | | |
| Average | 32 ✎ | 194.0 bpa | Nitrogen | 30N ✎ | 150N ✎ | |

FIG. 22

FIELD PROJECTIONS WORKSHEET

Field (Sloped) 163.75 Acres     ✎   What is solver? ✱     Seed: AAS Generic Seeds - Brand X 108 ✎
Solver Advantage: 0 bpa                                         Planting Date: 04/23/2015 ✎
                                                                                  Forecast: NW Indiana Norm ✎

| Zone | ✱ Seeding Rate ✱ | Projected Yield ✱ | Limiting Factor | Planting | ✱ | V8 | ✱ |
|---|---|---|---|---|---|---|---|
| Average | 31 ✎ | 203.1 bpa | Nitrogen | 30N ✎ | | 150N ✎ | |
| 26.99 ac / RevA / 0 | 33 ✎ | 215.3 bpa | Nitrogen | 30N ✎ | | 150N ✎ | |
| 19.73 ac / WmiA / 0 | 33 ✎ | 215.3 bpa | Nitrogen | 30N ✎ | | 150N ✎ | |
| 8.04 ac / WmiA / 0 | 33 ✎ | 215.3 bpa | Nitrogen | 30N ✎ | | 150N ✎ | |
| 7.59 ac / MouA / 0 | 33 ✎ | 220.1 bpa | Seed | 30N ✎ | | 150N ✎ | |
| 5.00 ac / BstA / 0 | 27 ✎ | 174.1 bpa | Nitrogen | 30N ✎ | | 150N ✎ | |
| Show all zones... | | | | | | | |
| Average | 31 ✎ | 203.1 bpa | Nitrogen | 30N ✎ | | 150N ✎ | |

*FIG. 23*

FIELD PROJECTIONS WORKSHEET

Field (Sloped) 163.75 Acres  
Solver Advantage: 0 bpa   What is solver?

Seed: AAS Generic Seeds - Brand X 108  
Planting Date: 04/23/2015  
Forecast: NW Indiana Norm

| Zone | Seeding Rate | Projected Yield | Limiting Factor | Planting | V8 |
|---|---|---|---|---|---|
| Average | 31 | 203.1 bpa | Nitrogen | 30N | 132N |
| 26.99 ac / RevA / 0 | 33 | 215.3 bpa | Nitrogen | 30N | 130N |
| 19.73 ac / WmiA / 0 | 33 | 215.3 bpa | Nitrogen | 30N | 135N |
| 8.04 ac / WmiA / 0 | 33 | 215.3 bpa | Nitrogen | 30N | 135N |
| 7.59 ac / MouA / 0 | 33 | 220.1 bpa | Seed | 30N | 125N |
| 5.00 ac / BstA / 0 | 27 | 174.1 bpa | Nitrogen | 30N | 125N |
| Show all zones... | | | | | |
| Average | 31 | 203.1 bpa | Nitrogen | 30N | 132N |

*FIG. 24*

| 8.04 ac / WmiA / 0 | 33 ✏ | 215.3 bpa | Nitrogen | 30N ✏ | 135N ✏ |
| --- | --- | --- | --- | --- | --- |
| 7.59 ac / MouA / 0 | 33 ✏ | 220.1 bpa | Seed | 30N ✏ | 125N ✏ |
| 5.00 ac / BstA / 0 | 27 ✏ | 174.1 bpa | Nitrogen | 30N ✏ | 125N ✏ |
| Show all zones... | | | | | |
| Average | 31 ✏ | 203.1 bpa | Nitrogen | 30N ✏ | 132N ✏ |

Add Nitrogen

Add Irrigation

Adding pivot irrigation to this field will help you accurately plan and control water applications, leading to significant yield increases and more accurate projections

[Add pivot irrigation to this field]

Slope and Elevation

FIG. 25

FIELD PROJECTIONS WORKSHEET

Field (Sloped) 163.75 Acres
Solver Advantage: 0 bpa   What is solver?

Seed: AAS Generic Seeds - Brand X 108
Planting Date: 04/23/2015
Forecast: NW Indiana Norm

| Zone | Seeding Rate | Projected Yield | Limiting Factor | Planting | V4 | V10 |
|---|---|---|---|---|---|---|
| Average | 38 | 254.8 bpa | Water | 30N | 130N | 107N |
| 17.00 ac / RevA / 0 | 42 | 280.1 bpa | Seed | 30N | 130N | 85N |
| 13.25 ac / WmiA / 0 | 42 | 279.2 bpa | Water | 30N | 130N | 85N |
| 7.76 ac / WmiA / 0 | 42 | 279.3 bpa | Water | 30N | 130N | 85N |
| 5.74 ac / MouA / 0 | 42 | 279.3 bpa | Water | 30N | 130N | 55N |
| 5.00 ac / BstA / 0 | 33 | 220.1 bpa | Seed | 30N | 130N | 140N |

FIG. 27

FIELD PROJECTIONS WORKSHEET

Field (Sloped) 163.75 Acres
Solver Advantage: 0 bpa   What is solver?

Seed: AAS Generic Seeds - Brand X 108
Planting Date: 04/23/2015
Forecast: NW Indiana Norm

| Zone | Seeding Rate | Projected Yield | Limiting Factor | Planting | V4 | V10 |
|---|---|---|---|---|---|---|
| Average | 38 | 254.8 bpa | Water | 30N | 130N | 107N |
| 17.00 ac / RevA / 0 | 42 | 280.1 bpa | Seed | 30N | 130N | 85N |
| 13.25 ac / WmiA / 0 | 42 | 279.2 bpa | Water | 30N | 130N | 85N |
| 7.76 ac / WmiA / 0 | 42 | 279.3 bpa | Water | 30N | 130N | 85N |
| 5.74 ac / MouA / 0 | 42 | 279.3 bpa | Water | 30N | 130N | 55N |
| 5.00 ac / BstA / 0 | 33 | 220.1 bpa | Seed | 30N | 130N | 140N |

FIG. 28

| Time (Hour) | Notes | Daily Rain Value | Hourly Rain | Begin Soil Moisture (trailing replace with higher quality, daily feed) | Begin Water Volume | Soil Dry Rate | Crop Uptake | Net Soil Moist Change | End Water Volume | End Soil Moist |
|---|---|---|---|---|---|---|---|---|---|---|
| 7:00:00 | Fri 5/31 7am | | 0.1 | 60.00% | 3.6 | | | 0.1 | 3.7 | 61.67% |
| 8:00:00 | | | 0 | 61.67% | 3.7 | 0.015625 | 0 | -0.015625 | 3.684375 | 61.41% |
| 9:00:00 | | | 0 | 61.41% | 3.684375 | 0.015625 | 0 | -0.015625 | 3.66875 | 61.15% |
| 10:00:00 | | | 0 | 61.15% | 3.66875 | 0.015625 | 0 | -0.015625 | 3.653125 | 60.89% |
| 11:00:00 | | | 0 | 60.89% | 3.653125 | 0.015625 | 0 | -0.015625 | 3.6375 | 60.63% |
| 12:00:00 | | | 1.5 | 60.63% | 3.6375 | | | 1.5 | 5.1375 | 85.63% |
| 13:00:00 | | | 0 | 85.63% | 5.1375 | 0.015625 | 0 | -0.015625 | 5.121875 | 85.36% |
| 14:00:00 | | | 0 | 85.36% | 5.121875 | 0.015625 | 0 | -0.015625 | 5.10625 | 85.10% |
| 15:00:00 | | | 0 | 85.10% | 5.10625 | 0.015625 | 0 | -0.015625 | 5.090625 | 84.84% |
| 16:00:00 | | | 0 | 84.84% | 5.090625 | 0.015625 | 0 | -0.015625 | 5.075 | 84.58% |
| 17:00:00 | | | 0.25 | 84.58% | 5.075 | | | 0.25 | 5.325 | |
| 18:00:00 | | | 0 | 88.75% | 5.325 | 0.015625 | 0 | -0.015625 | 5.309375 | |
| 19:00:00 | | | 0 | 88.49% | 5.309375 | 0.015625 | 0 | -0.015625 | 5.29375 | |
| 20:00:00 | | | 0 | 88.23% | 5.29375 | 0.015625 | 0 | -0.015625 | 5.278125 | |
| 21:00:00 | | | 0 | 87.97% | 5.278125 | 0.015625 | 0 | -0.015625 | 5.2625 | |
| 22:00:00 | | | 0 | 87.71% | 5.2625 | 0.015625 | 0 | -0.015625 | 5.246875 | |
| 23:00:00 | | | 0 | 87.45% | 5.246875 | 0.015625 | 0 | -0.015625 | 5.23125 | |
| 24:00:00 | | | 0 | 87.19% | 5.23125 | 0.015625 | 0 | -0.015625 | 5.215625 | |
| 1:00:00 | Sat 1am storm | | 0 | 86.93% | 5.215625 | 0.015625 | 0 | -0.015625 | 5.2 | |
| 2:00:00 | | | 0 | 86.67% | 5.2 | 0.015625 | 0 | -0.015625 | 5.184375 | |
| 3:00:00 | | | 0 | 86.41% | 5.184375 | 0.015625 | 0 | -0.015625 | 5.16875 | |
| 4:00:00 | | | 0 | 86.15% | 5.16875 | 0.015625 | 0 | -0.015625 | 5.153125 | |
| 5:00:00 | | | 0 | 85.89% | 5.153125 | 0.015625 | 0 | -0.015625 | 5.1375 | |
| 6:00:00 | | | 0 | 85.63% | 5.1375 | 0.015625 | 0 | -0.015625 | 5.121875 | |
| 7:00:00 | Day 1 | 1.85 | 0 | 85.36% | 5.121875 | 0.015625 | 0 | -0.015625 | 5.10625 | 84.84% |
| 8:00:00 | | | 0 | 85.10% | 5.10625 | 0.015625 | 0 | -0.015625 | 5.090625 | 84.58% |
| 9:00:00 | | | 0 | 84.84% | 5.090625 | 0.015625 | 0 | -0.015625 | 5.075 | 84.32% |
| 10:00:00 | | | 0 | 84.58% | 5.075 | 0.015625 | 0 | -0.015625 | 5.059375 | 84.06% |
| 11:00:00 | | | 0 | 84.32% | 5.059375 | 0.015625 | 0 | -0.015625 | 5.04375 | 83.80% |
| 12:00:00 | | | 0 | 84.06% | 5.04375 | 0.015625 | 0 | -0.015625 | 5.028125 | 83.54% |
| 13:00:00 | | | 0 | 83.80% | 5.028125 | 0.015625 | 0 | -0.015625 | 5.0125 | 83.29% |
| 14:00:00 | | | 0 | 83.54% | 5.0125 | 0.015625 | 0 | -0.015625 | 4.996875 | 83.28% |
| 15:00:00 | | | 0 | 83.28% | 4.996875 | 0.015625 | 0 | -0.015625 | 4.98125 | 83.02% |

FIG. 33A

| Time | | | % | | -0.015625 | 0.015625 | | % |
|---|---|---|---|---|---|---|---|---|
| 16:00:00 | | 0 | 83.02% | 4.96125 | 0.015625 | -0.015625 | 4.965625 | 82.76% |
| 17:00:00 | | 0 | 82.76% | 4.965625 | 0.015625 | -0.015625 | 4.95 | 82.50% |
| 18:00:00 | | 0 | 82.50% | 4.95 | 0.015625 | -0.015625 | 4.934375 | 82.24% |
| 19:00:00 | | 0 | 82.24% | 4.934375 | 0.015625 | -0.015625 | 4.91875 | 81.98% |
| 20:00:00 | | 0 | 81.98% | 4.91875 | 0.015625 | -0.015625 | 4.903125 | 81.72% |
| 21:00:00 | | 0 | 81.72% | 4.903125 | 0.015625 | -0.015625 | 4.8875 | 81.46% |
| 22:00:00 | | 0 | 81.46% | 4.8875 | 0.015625 | -0.015625 | 4.871875 | 81.20% |
| 23:00:00 | | 0 | 81.20% | 4.871875 | 0.015625 | -0.015625 | 4.85625 | 80.94% |
| 24:00:00 | | 0 | 80.94% | 4.85625 | 0.015625 | -0.015625 | 4.840625 | 80.68% |
| 1:00:00 | | 0 | 80.68% | 4.840625 | 0.015625 | -0.015625 | 4.825 | 80.42% |
| 2:00:00 | | 0 | 80.42% | 4.825 | 0.015625 | -0.015625 | 4.809375 | 80.16% |
| 3:00:00 | | 0 | 80.16% | 4.809375 | 0.015625 | -0.015625 | 4.79375 | 79.90% |
| 4:00:00 | | 0 | 79.90% | 4.79375 | 0.015625 | -0.015625 | 4.778125 | 79.64% |
| 5:00:00 | | 0 | 79.64% | 4.778125 | 0.015625 | -0.015625 | 4.7625 | 79.38% |
| 6:00:00 | | 0 | 79.38% | 4.7625 | 0.015625 | -0.015625 | 4.746875 | 79.11% |
| 7:00:00 | Day 2 | 0 | 79.11% | 4.746875 | 0.015625 | -0.015625 | 4.73125 | 78.85% |
| 8:00:00 | | 0 | 78.85% | 4.73125 | 0.015625 | -0.015625 | 4.715625 | 78.59% |
| 9:00:00 | | 0 | 78.59% | 4.715625 | 0.015625 | -0.015625 | 4.7 | 78.33% |
| 10:00:00 | | 0 | 78.33% | 4.7 | 0.015625 | -0.015625 | 4.684375 | 78.07% |
| 11:00:00 | | 0 | 78.07% | 4.684375 | 0.015625 | -0.015625 | 4.66875 | 77.81% |
| 12:00:00 | | 0 | 77.81% | 4.66875 | 0.015625 | -0.015625 | 4.653125 | 77.55% |
| 13:00:00 | | 0 | 77.55% | 4.653125 | 0.015625 | -0.015625 | 4.6375 | 77.29% |
| 14:00:00 | | 0 | 77.29% | 4.6375 | 0.015625 | -0.015625 | 4.621875 | 77.03% |
| 15:00:00 | | 0 | 77.03% | 4.621875 | 0.015625 | -0.015625 | 4.60625 | 76.77% |
| 16:00:00 | Sunday 4pm | 0 | 76.77% | 4.60625 | 0.015625 | -0.015625 | 4.590625 | 76.51% |
| 17:00:00 | | 0 | 76.51% | 4.590625 | 0.015625 | -0.015625 | 4.575 | 76.25% |
| 18:00:00 | | 0 | 76.25% | 4.575 | 0.015625 | -0.015625 | 4.559375 | 75.99% |
| 19:00:00 | | 0 | 75.99% | 4.559375 | 0.015625 | -0.015625 | 4.54375 | 75.73% |
| 20:00:00 | | 0 | 75.73% | 4.54375 | 0.015625 | -0.015625 | 4.528125 | 75.47% |
| 21:00:00 | | 0 | 75.47% | 4.528125 | 0.015625 | -0.015625 | 4.5125 | 75.21% |
| 22:00:00 | | 0 | 75.21% | 4.5125 | 0.015625 | -0.015625 | 4.496875 | 74.95% |
| 23:00:00 | | 0 | 74.95% | 4.496875 | 0.015625 | -0.015625 | 4.48125 | 74.69% |
| 24:00:00 | | 0 | 74.69% | 4.48125 | 0.015625 | -0.015625 | 4.465625 | 74.43% |
| 1:00:00 | | 0 | 74.43% | 4.465625 | 0.015625 | -0.015625 | 4.45 | 74.17% |
| 2:00:00 | | 0 | 74.17% | 4.45 | 0.015625 | -0.015625 | 4.434375 | 73.91% |
| 3:00:00 | | 0 | 73.91% | 4.434375 | 0.015625 | -0.015625 | 4.41875 | 73.65% |

| Time | | | % | Value | +delta | -delta | Value | % |
|---|---|---|---|---|---|---|---|---|
| 4:00:00 | | 0 | 73.65% | 4.418875 | 0.015625 | -0.015625 | 4.403125 | 73.39% |
| 5:00:00 | | 0 | 73.39% | 4.403125 | 0.015625 | -0.015625 | 4.3875 | 73.13% |
| 6:00:00 | | 0 | 73.13% | 4.3875 | 0.015625 | -0.015625 | 4.371875 | 72.86% |
| 7:00:00 | Day 3 | 0 | 72.86% | 4.371875 | 0.015625 | -0.015625 | 4.35625 | 72.60% |
| 8:00:00 | | 0 | 72.60% | 4.35625 | 0.015625 | -0.015625 | 4.340625 | 72.34% |
| 9:00:00 | | 0 | 72.34% | 4.340625 | 0.015625 | -0.015625 | 4.325 | 72.08% |
| 10:00:00 | | 0 | 72.08% | 4.325 | 0.015625 | -0.015625 | 4.309375 | 71.82% |
| 11:00:00 | Monday 11am | 0 | 71.82% | 4.309375 | 0.015625 | -0.015625 | 4.29375 | 71.56% |
| 12:00:00 | | 0 | 71.56% | 4.29375 | 0.015625 | -0.015625 | 4.278125 | 71.30% |
| 13:00:00 | | 0 | 71.30% | 4.278125 | 0.015625 | -0.015625 | 4.2625 | 71.04% |
| 14:00:00 | | 0 | 71.04% | 4.2625 | 0.015625 | -0.015625 | 4.246875 | 70.78% |
| 15:00:00 | | 0 | 70.78% | 4.246875 | 0.015625 | -0.015625 | 4.23125 | 70.52% |
| 16:00:00 | | 0 | 70.52% | 4.23125 | 0.015625 | -0.015625 | 4.215625 | 70.26% |
| 17:00:00 | | 0 | 70.26% | 4.215625 | 0.015625 | -0.015625 | 4.2 | 70.00% |
| 18:00:00 | | 0 | 70.00% | 4.2 | 0.015625 | -0.015625 | 4.184375 | 69.74% |
| 19:00:00 | | 0 | 69.74% | 4.184375 | 0.015625 | -0.015625 | 4.16875 | 69.48% |
| 20:00:00 | | 0 | 69.48% | 4.16875 | 0.015625 | -0.015625 | 4.153125 | 69.22% |
| 21:00:00 | | 0 | 69.22% | 4.153125 | 0.015625 | -0.015625 | 4.1375 | 68.96% |
| 22:00:00 | | 0 | 68.96% | 4.1375 | 0.015625 | -0.015625 | 4.121875 | 68.70% |
| 23:00:00 | | 0 | 68.70% | 4.121875 | 0.015625 | -0.015625 | 4.10625 | 68.44% |
| 24:00:00 | | 0 | 68.44% | 4.10625 | 0.015625 | -0.015625 | 4.090625 | 68.18% |
| 1:00:00 | | 0 | 68.18% | 4.090625 | 0.015625 | -0.015625 | 4.075 | 67.92% |
| 2:00:00 | | 0 | 67.92% | 4.075 | 0.015625 | -0.015625 | 4.059375 | 67.66% |
| 3:00:00 | | 0 | 67.66% | 4.059375 | 0.015625 | -0.015625 | 4.04375 | 67.40% |
| 4:00:00 | | 0 | 67.40% | 4.04375 | 0.015625 | -0.015625 | 4.028125 | 67.14% |
| 5:00:00 | | 0 | 67.14% | 4.028125 | 0.015625 | -0.015625 | 4.0125 | 66.88% |
| 6:00:00 | Tues 6am | 0 | 66.88% | 4.0125 | 0.015625 | -0.015625 | 3.996875 | 66.61% |
| 7:00:00 | Day 4 | 0 | 66.61% | 3.996875 | 0.015625 | -0.015625 | 3.98125 | 66.35% |
| 8:00:00 | Tues 8am | 0 | 66.35% | 3.98125 | 0.015625 | -0.015625 | 3.965625 | 66.09% |
| 9:00:00 | | 0 | 66.09% | 3.965625 | 0.015625 | -0.015625 | 3.95 | 65.83% |
| 10:00:00 | | 0 | 65.83% | 3.95 | 0.015625 | -0.015625 | 3.934375 | 65.57% |
| 11:00:00 | | 0 | 65.57% | 3.934375 | 0.015625 | -0.015625 | 3.91875 | 65.31% |
| 12:00:00 | | 0 | 65.31% | 3.91875 | 0.015625 | -0.015625 | 3.903125 | 65.05% |
| 13:00:00 | | 0 | 65.05% | 3.903125 | 0.015625 | -0.015625 | 3.8875 | 64.79% |
| 14:00:00 | | 0 | 64.79% | 3.8875 | 0.015625 | -0.015625 | 3.871875 | 64.53% |
| 15:00:00 | | 0 | 64.53% | 3.871875 | 0.015625 | -0.015625 | 3.85625 | 64.27% |

| | | | | | | | |
|---|---|---|---|---|---|---|---|
| 16:00:00 | | 0 | 64.27% | | 3.858125 | 0.015625 | -0.015625 | 3.840625 | 64.01% |
| 17:00:00 | | 0 | 64.01% | | 3.840625 | 0.015625 | -0.015625 | 3.825 | 63.75% |
| 18:00:00 | Tues 6pm | 0 | 63.75% | | 3.825 | 0.015625 | -0.015625 | 3.809375 | 63.49% |
| 19:00:00 | | 0 | 63.49% | | 3.809375 | 0.015625 | -0.015625 | 3.79375 | 63.23% |
| 20:00:00 | | 0 | 63.23% | | 3.79375 | 0.015625 | -0.015625 | 3.778125 | 62.97% |
| 21:00:00 | | 0 | 62.97% | | 3.778125 | 0.015625 | -0.015625 | 3.7625 | 62.71% |
| 22:00:00 | | 0 | 62.71% | | 3.7625 | 0.015625 | -0.015625 | 3.746875 | 62.45% |
| 23:00:00 | | 0 | 62.45% | | 3.746875 | 0.015625 | -0.015625 | 3.73125 | 62.19% |
| 24:00:00 | | 0 | 62.19% | | 3.73125 | 0.015625 | -0.015625 | 3.715625 | 61.93% |
| 1:00:00 | | 0 | 61.93% | | 3.715625 | 0.015625 | -0.015625 | 3.7 | 61.67% |
| 2:00:00 | | 0 | 61.67% | | 3.7 | 0.015625 | -0.015625 | 3.684375 | 61.41% |
| 3:00:00 | | 0 | 61.41% | | 3.684375 | 0.015625 | -0.015625 | 3.66875 | 61.15% |
| 4:00:00 | | 0 | 61.15% | | 3.66875 | 0.015625 | -0.015625 | 3.653125 | 60.89% |
| 5:00:00 | | 0 | 60.89% | | 3.653125 | 0.015625 | -0.015625 | 3.6375 | 60.63% |
| 6:00:00 | | 0 | 60.63% | | 3.6375 | 0.015625 | -0.015625 | 3.621875 | 60.36% |
| 7:00:00 | Day 5 | 0 | 60.36% | | 3.621875 | 0.015625 | -0.015625 | 3.60625 | 60.10% |
| 8:00:00 | | 0 | 60.10% | | 3.60625 | 0.015625 | -0.015625 | 3.590625 | 59.84% |
| 9:00:00 | | 0 | 59.84% | | 3.590625 | 0.015625 | -0.015625 | 3.575 | 59.58% |
| 10:00:00 | | 0 | 59.58% | | 3.575 | 0.015625 | -0.015625 | 3.559375 | 59.32% |
| 11:00:00 | | 0 | 59.32% | | 3.559375 | 0.015625 | -0.015625 | 3.54375 | 59.06% |
| 12:00:00 | | 0 | 59.06% | | 3.54375 | 0.015625 | -0.015625 | 3.528125 | 58.80% |
| 13:00:00 | | 0 | 58.80% | | 3.528125 | 0.015625 | -0.015625 | 3.5125 | 58.54% |
| 14:00:00 | | 0 | 58.54% | | 3.5125 | 0.015625 | -0.015625 | 3.496875 | 58.28% |
| 15:00:00 | | 0 | 58.28% | | 3.496875 | 0.015625 | -0.015625 | 3.48125 | 58.02% |
| 16:00:00 | | 0 | 58.02% | | 3.48125 | 0.015625 | -0.015625 | 3.465625 | 57.76% |
| 17:00:00 | | 0 | 57.76% | | 3.465625 | 0.015625 | -0.015625 | 3.45 | 57.50% |
| 18:00:00 | wed 6pm | 0 | 57.50% | | 3.45 | 0.015625 | -0.015625 | 3.434375 | 57.24% |
| 19:00:00 | | 0 | 57.24% | | 3.434375 | 0.015625 | -0.015625 | 3.41875 | 56.98% |
| 20:00:00 | | 0 | 56.98% | | 3.41875 | 0.015625 | -0.015625 | 3.403125 | 56.72% |
| 21:00:00 | | 0 | 56.72% | | 3.403125 | 0.015625 | -0.015625 | 3.3875 | 56.46% |
| 22:00:00 | | 0 | 56.46% | | 3.3875 | 0.015625 | -0.015625 | 3.371875 | 56.20% |
| 23:00:00 | | 0 | 56.20% | | 3.371875 | 0.015625 | -0.015625 | 3.35625 | 55.94% |
| 24:00:00 | | 0 | 55.94% | | 3.35625 | 0.015625 | -0.015625 | 3.340625 | 55.68% |
| 1:00:00 | | 0 | 55.68% | | 3.340625 | 0.015625 | -0.015625 | 3.325 | 55.42% |
| 2:00:00 | | 0 | 55.42% | | 3.325 | 0.015625 | -0.015625 | 3.309375 | 55.16% |
| 3:00:00 | | 0 | 55.16% | | 3.309375 | | | 3.29375 | |

FIG. 33D

| Time | | | | % | | Val1 | +0.015625 | -0.015625 | Val2 |
|---|---|---|---|---|---|---|---|---|---|
| 4:00:00 | | | | 54.90% | 0 | 3.293125 | 0.015625 | -0.015625 | 3.278125 |
| 5:00:00 | | | | 54.84% | 0 | 3.278125 | 0.015625 | -0.015625 | 3.2625 |
| 6:00:00 | | | | 54.36% | 0 | 3.2625 | 0.015625 | -0.015625 | 3.246875 |
| 7:00:00 Day 6 | | | | 54.11% | 0 | 3.246875 | 0.015625 | -0.015625 | 3.23125 |
| 8:00:00 | | | | 53.85% | 0 | 3.23125 | 0.015625 | -0.015625 | 3.215625 |
| 9:00:00 | | | | 53.59% | 0 | 3.215625 | 0.015625 | -0.015625 | 3.2 |
| 10:00:00 | | | | 53.33% | 0 | 3.2 | 0.015625 | -0.015625 | 3.184375 |
| 11:00:00 | | | | 53.07% | 0 | 3.184375 | 0.015625 | -0.015625 | 3.16875 |
| 12:00:00 | | | | 52.81% | 0 | 3.16875 | 0.015625 | -0.015625 | 3.153125 |
| 13:00:00 | | | | 52.55% | 0 | 3.153125 | 0.015625 | -0.015625 | 3.1375 |
| 14:00:00 | | | | 52.29% | 0 | 3.1375 | 0.015625 | -0.015625 | 3.121875 |
| 15:00:00 | | | | 52.03% | 0 | 3.121875 | 0.015625 | -0.015625 | 3.10625 |
| 16:00:00 | | | | 51.77% | 0 | 3.10625 | 0.015625 | -0.015625 | 3.090625 |
| 17:00:00 | | | | 51.51% | 0 | 3.090625 | 0.015625 | -0.015625 | 3.075 |
| 18:00:00 litters 6pm | | | | 51.25% | 0 | 3.075 | 0.015625 | -0.015625 | 3.059375 |
| 19:00:00 | | | | 50.99% | 0 | 3.059375 | 0.015625 | -0.015625 | 3.04375 |
| 20:00:00 | | | | 50.73% | 0 | 3.04375 | 0.015625 | -0.015625 | 3.028125 |
| 21:00:00 | | | | 50.47% | 0 | 3.028125 | 0.015625 | -0.015625 | 3.0125 |
| 22:00:00 | | | | 50.21% | 0 | 3.0125 | 0.015625 | -0.015625 | 2.996875 |
| 23:00:00 | | | | 49.95% | 0 | 2.996875 | 0.015625 | -0.015625 | 2.98125 |
| 24:00:00 | | | | 49.69% | 0 | 2.98125 | 0.015625 | -0.015625 | 2.965625 |
| 1:00:00 | | | | 49.43% | 0 | 2.965625 | 0.015625 | -0.015625 | 2.95 |
| 2:00:00 | | | | 49.17% | 0 | 2.95 | 0.015625 | -0.015625 | 2.934375 |
| 3:00:00 | | | | 48.91% | 0 | 2.934375 | 0.015625 | -0.015625 | 2.91875 |
| 4:00:00 | | | | 48.65% | 0 | 2.91875 | 0.015625 | -0.015625 | 2.903125 |
| 5:00:00 | | | | 48.39% | 0 | 2.903125 | 0.015625 | -0.015625 | 2.8875 |
| 6:00:00 | | | | 48.13% | 0 | 2.8875 | 0.015625 | -0.015625 | 2.871875 |
| 7:00:00 Day 7 | | | | 47.85% | 0 | 2.871875 | 0.015625 | -0.015625 | 2.85625 |
| 8:00:00 | | | | 47.60% | 0 | 2.85625 | 0.015625 | -0.015625 | 2.840625 |
| 9:00:00 | | | | 47.34% | 0 | 2.840625 | 0.015625 | -0.015625 | 2.825 |
| 10:00:00 | | | | 47.08% | 0 | 2.825 | 0.015625 | -0.015625 | 2.809375 |
| 11:00:00 | | | | 46.82% | 0 | 2.809375 | 0.015625 | -0.015625 | 2.79375 |
| 12:00:00 | | | | 46.56% | 0 | 2.79375 | 0.015625 | -0.015625 | 2.778125 |
| 13:00:00 | | | | 46.30% | 0 | 2.778125 | 0.015625 | -0.015625 | 2.7625 |
| 14:00:00 | | | | 46.04% | 0 | 2.7625 | 0.015625 | -0.015625 | 2.746875 |
| 15:00:00 | | | | 45.78% | 0 | 2.746875 | 0.015625 | -0.015625 | 2.731125 |

FIG. 33E

| | | | | | | | |
|---|---|---|---|---|---|---|---|
| 16:00:00 | 0 | 45.52% | 2.73125 | 0.015625 | -0.015625 | 2.715625 | |
| 17:00:00 | 0 | 45.26% | 2.715625 | 0.015625 | -0.015625 | 2.7 | |
| 18:00:00 | 0 | 45.00% | 2.7 | 0.015625 | -0.015625 | 2.684375 | |
| 19:00:00 | 0 | 44.74% | 2.684375 | 0.015625 | -0.015625 | 2.66875 | |
| 20:00:00 | 0 | 44.48% | 2.66875 | 0.015625 | -0.015625 | 2.653125 | |
| 21:00:00 | 0 | 44.22% | 2.653125 | 0.015625 | -0.015625 | 2.6375 | |
| 22:00:00 | 0 | 43.96% | 2.6375 | 0.015625 | -0.015625 | 2.621875 | |
| 23:00:00 | 0 | 43.70% | 2.621875 | 0.015625 | -0.015625 | 2.60625 | |
| 24:00:00 | 0 | 43.44% | 2.60625 | 0.015625 | -0.015625 | 2.590625 | |

*FIG. 33F*

| | (%) FC RANGE | |
|---|---|---|
| Wet | 1 | 0.85 |
| Moist | 0.84 | 0.7 |
| Dry | 0.69 | 0.55 |
| Stressed | 0.54 | 0 |

FIG. 36

AGRONOMIC SYSTEMS, METHODS AND APPARATUSES

RELATED APPLICATIONS

The present application claims priority benefit of copending U.S. Provisional Patent Application No. 62/149,211, filed Apr. 17, 2015, which is incorporated by reference herein in its entirety.

FIELD OF THE INVENTION

The present disclosure relates generally to agronomics and, more particularly, to agronomic systems, methods and apparatuses.

BACKGROUND

Today, the most common farming practice includes planting identical plant variety and consistent plant population across an entire field and applying inputs, such as fertilizers, herbicides, insecticides, etc., to the entire field at a constant rate. Both of these conventional practices are performed with a belief that a uniform plant variety, uniform plant population, and/or uniform rate of input application over the entire field will maximize crop yield. Unfortunately, these conventional practices result in maximizing crop yield much less than they succeed. Many reasons exist that cause these conventional practices to fail such as, for example, inconsistent soil types and conditions, inconsistent crop conditions, inconsistent weather patterns, inconsistent soil slopes, etc. Thus, many inconsistencies exist across an entire field that impact the growth of a crop. These conventional practices may also result in wasted money, actually reduce crop yield, and potentially damage the environment through over application of inputs (e.g., fertilizers, herbicides, insecticides, or any other chemicals or inputs applied to the field).

Precision farming is a term used to describe the management of intra-field variations in soil and crop conditions, specifically tailoring soil and crop management to the conditions at discrete, usually contiguous, locations throughout a field. Typical precision farming techniques include: Varying plant varieties and plant population based on the ability of the soil to support growth of the plants; and selective application of farming inputs or products such as herbicides, insecticides, and fertilizers. Thus, precision farming may have at least three advantages over conventional practices. First, precision farming may increase crop yields by at least determining correct plant varieties and application rates of seeds, herbicides, pesticides, fertilizer and other inputs for specific fields. This advantage may also result in greater profits for the farmer. Second, precision farming may lower a farmer's expense associated with producing a crop by utilizing appropriate quantities of seeds and inputs for each particular field. That is, application rates of seeds, herbicides, pesticides, fertilizer, and other inputs are determined based on the specific characteristics of each field. Finally, precision farming may have a less harmful impact on the environment by reducing quantities of excess inputs and chemicals applied to a field, thereby reducing quantities of inputs and chemicals that may ultimately find their way into the atmosphere and water sources, such as ponds, streams, rivers, lakes, aquifers, etc.

However, precision farming practices used today fail to account for many agronomic factors required to effectively manage crops and fields, nor do these precision farming practices identify an agronomic factor that limits a yield for crops and fields. Moreover, past efforts pertaining to precision farming are time consuming and focus on a limited set of agronomic factors.

Furthermore, agronomic forecasting is dependent heavily on historic data from previous planting seasons. As is often the case, past performance is not a guarantee of future results. That is, agronomic factors differ from year to year and heavy reliance on historic data (e.g., rainfall, soil conditions, etc.) can increase the inaccuracy of forecasts.

Still further, many growers or farmers set expectations for crop yield prior to planting, then formulate forecasts on how to achieve these expectations. Forecasting in this manner sets artificial restrictions on yield and often results in inefficiencies and wasted resources.

Moreover, getting information to a farmer, equipment operator, or getting operating information to agricultural equipment in the field is limited and difficult.

SUMMARY

In one example, there is a need for one or more agronomic systems, methods and/or apparatuses that cure one or more of these problems.

In one example, there is a need for a system, method and/or apparatus that increases crop yield.

In one example, there is a need for a system, method and/or apparatus that identifies an agronomic factor that limits crop yield.

In one example, there is a need for a system, method and/or apparatus that senses soil and/or crop conditions in real-time, evaluates agronomic factors impacting a particular crop, identifies the agronomic factor that limits crop yield (i.e., the limiting factor) and informs a user/farmer of the limiting factor to enable the user/farmer to take action to decrease or eliminate the limiting factor's impact on the crop.

In one example, there is need for a system, method and/or apparatus for getting information to a farmer or equipment operator in the field, or getting operating information to agricultural equipment in the field.

In one example, an agricultural system is provided and includes a first component including a network interface for receiving an agricultural prescription over a network. The agricultural prescription is comprised of at least one agricultural characteristic and at least one agricultural action. The agricultural system also includes a second component in communication with the first component and configured to receive the agricultural prescription from the first component. The second component is configured to output the at least one agricultural action.

In one example, an agricultural system including an agricultural device and an agricultural communication device including a network interface for receiving an agricultural prescription over a network. The agricultural prescription is comprised of at least one agricultural characteristic and at least one agricultural action. The agricultural device is configured to output the agricultural action.

In one example, a method of operating an agricultural system is provided. The method includes transmitting an agricultural prescription over a network from a server and receiving the agricultural prescription with a first component of the agricultural system. The first component includes a network interface, and the agricultural prescription is comprised of at least one agricultural characteristic and at least one agricultural action. The method also includes communicating the agricultural prescription from the first component to a second component and outputting the at least one agricultural action with the second component.

In one example, a method of operating an agricultural system is provided and consists essentially of generating an agricultural prescription with a computing device. The agricultural prescription includes at least one agricultural characteristic and at least one agricultural action. The method also consists essentially of storing the agricultural prescription on a server, transmitting data from a first component of the agricultural system to the server over a network, transmitting the agricultural prescription from the server to the first component over the network upon receipt of the data by the server, receiving the agricultural prescription with the first component, communicating the agricultural prescription to a second component of the agricultural system, and outputting the agricultural action with the second component.

In one example, a method of operating an agricultural system is provided and consists essentially of generating an agricultural prescription with a computing device. The agricultural prescription includes at least one agricultural characteristic and at least one agricultural action. The method also consists essentially of storing the agricultural prescription on a server and transmitting the agricultural prescription from the server to a component of the agricultural system over a network.

In one example, a method of operating an agricultural system is provided and consists essentially of receiving an agricultural prescription over a network with a first component of the agricultural system. The agricultural prescription includes at least one agricultural characteristic and at least one agricultural action. The method also consists essentially of communicating the agricultural prescription to a second component of the agricultural system, outputting the agricultural action with the second component, and executing the agricultural action with an agricultural device.

In one aspect, an agricultural system is provided and includes an information gathering component, a first component and a second component. The information gathering component is configured to gather information pertaining to at least one agricultural characteristic and generate agricultural data associated with the gathered information. The agricultural data is transmitted over a network and used to generate an agricultural prescription. The agricultural prescription is comprised of at least one agricultural characteristic and at least one agricultural action. The first component includes a network interface for receiving the agricultural prescription over the network and the second component is in communication with the first component. The second component is configured to receive the agricultural prescription from the first component and is configured to output the at least one agricultural action.

In one aspect, the first component may be configured to receive the agricultural prescription over the network from a server, and the agricultural data may be transmitted over the network to the server.

In one aspect, the information gathering component may transmit the agricultural data over the network.

In one aspect, the information gathering component may be in communication with the first component and the first component may transmit the agricultural data over the network.

In one aspect, the agricultural data may be relied upon to generate a second agricultural prescription based on the agricultural data, and the second agricultural prescription is different than the agricultural prescription.

In one aspect, the first component may be configured to receive the second agricultural prescription over the network.

In one aspect, an electronic device may receive the transmitted agricultural data, may generate a second agricultural prescription based on the agricultural data, and may transmit the second agricultural prescription.

In one aspect, the electronic device may transmit the second agricultural prescription to a server where the second agricultural prescription is stored.

In one aspect, the first component may be configured to receive the second agricultural prescription over the network.

In one aspect, the electronic device may be a computing element.

In one aspect, the electronic device may be at least one of a personal computer, a laptop, a mobile electronic device, a tablet, a cellular enabled phone, and a smartphone.

In one aspect, the agricultural prescription may be one of a plurality of agricultural prescriptions. The plurality of agricultural prescriptions may each be associated with particular agricultural data, and the one of the agricultural prescriptions received by the first component over the network may be associated with the agricultural data transmitted over the network.

In one aspect, the agricultural data may be associated with one of water, sunlight, temperature, humidity, barometric pressure, soil characteristics, nitrogen, a pest, an undesired plant and a fungus.

In one aspect, the information gathering component may include a light emitter configured to emit light and a light detector configured to receive light.

In one aspect, the light emitter may be configured to emit light that engages an object, the light may be configured to reflect back toward the light detector after engaging the object, and the light detector may be configured to receive the reflected back light. The agricultural data may be associated with the light received by the light detector.

In one aspect, the agricultural data may be associated with at least one of a presence of a plant, an absence of a plant and a height of a plant.

In one aspect, the light emitter may be an illumination device and the light detector may be a photo detector.

In one aspect, the information gathering component may be at least one of a sensor and a camera.

In one aspect, the information gathering component may be positioned on an agricultural device.

In one aspect, the agricultural device may be one of a tractor, a harvester, a planter, a sprayer, an agricultural implement, an unmanned aerial vehicle, a manned aerial vehicle, an all-terrain vehicle, an automobile, and an irrigation device.

In one aspect, the system may further include a housing. The first component may be at least partially positioned inside the housing.

In one aspect, the second component may be at least partially positioned in the housing.

In one aspect, an agricultural system is provided and includes a first component, a second component and an information gathering component. The first component includes a network interface for receiving an agricultural prescription over a network. The agricultural prescription is comprised of at least one agricultural characteristic and at least one agricultural action. The second component is in communication with the first component and configured to receive the agricultural prescription from the first component. The second component is configured to output the at least one agricultural action. The information gathering component is configured to gather information pertaining to the at least one agricultural characteristic and generate agricultural data associated with the gathered information. The agricultural data is configured to be transmitted over a network.

In one aspect, the first component may be configured to receive the agricultural prescription over the network from a server, and the agricultural data may be transmitted over the network to the server.

In one aspect, the information gathering component may transmit the agricultural data over the network.

In one aspect, the information gathering component may be in communication with the first component and the first component may transmit the agricultural data over the network.

In one aspect, the agricultural data may be relied upon to generate a second agricultural prescription based on the agricultural data, and the second agricultural prescription is different than the agricultural prescription.

In one aspect, the first component may be configured to receive the second agricultural prescription over the network.

In one aspect, an electronic device may receive the transmitted agricultural data, may generate a second agricultural prescription based on the agricultural data, and may transmit the second agricultural prescription.

In one aspect, the electronic device may transmit the second agricultural prescription to a server where the second agricultural prescription is stored.

In one aspect, the first component may be configured to receive the second agricultural prescription over the network.

In one aspect, the electronic device may be a computing element.

In one aspect, the electronic device may be at least one of a personal computer, a laptop, a mobile electronic device, a tablet, a cellular enabled phone, and a smartphone.

In one aspect, the agricultural prescription may be one of a plurality of agricultural prescriptions. The plurality of agricultural prescriptions may each be associated with particular agricultural data, and the one of the agricultural prescriptions received by the first component over the network may be associated with the agricultural data transmitted over the network.

In one aspect, the agricultural data may be associated with one of water, sunlight, temperature, humidity, barometric pressure, soil characteristics, nitrogen, a pest, an undesired plant and a fungus.

In one aspect, the information gathering component may include a light emitter configured to emit light and a light detector configured to receive light.

In one aspect, the light emitter may be configured to emit light that engages an object, the light may be configured to reflect back toward the light detector after engaging the object, and the light detector may be configured to receive the reflected back light. The agricultural data may be associated with the light received by the light detector.

In one aspect, the agricultural data may be associated with at least one of a presence of a plant, an absence of a plant and a height of a plant.

In one aspect, the light emitter may be an illumination device and the light detector may be a photo detector.

In one aspect, the information gathering component may be at least one of a sensor and a camera.

In one aspect, the information gathering component may be positioned on an agricultural device.

In one aspect, the agricultural device may be one of a tractor, a harvester, a planter, a sprayer, an agricultural implement, an unmanned aerial vehicle, a manned aerial vehicle, an all-terrain vehicle, an automobile, and an irrigation device.

In one aspect, the system may further include a housing. The first component may be at least partially positioned inside the housing.

In one aspect, the second component may be at least partially positioned in the housing.

In one aspect, an agricultural system is provided and includes a computing element and an information gathering component. The computing element includes a processor and a memory. The computing element is configured to receive data from a source and identify a limiting agronomic characteristic from a plurality of agronomic characteristics that limits a yield of a crop. The computing element is configured to generate an agricultural prescription comprised of at least one agricultural characteristic and at least one agricultural action, and the agricultural prescription is configured to be transmitted over a network. The information gathering component is configured to gather information pertaining to the at least one agricultural characteristic and generate agricultural data associated with the gathered information. The agricultural data is configured to be transmitted over the network and be received by the computing element.

In one aspect, the agricultural system may further include an agricultural device configured to receive the agricultural prescription over the network and output the at least one agricultural action.

In one aspect, the information gathering component may be coupled to the agricultural device.

In one aspect, the agricultural system may further include a first component including a network interface for receiving the agricultural prescription over the network.

In one aspect, the agricultural system may further include a second component in communication with the first component and configured to receive the agricultural prescription from the first component. The second component may be configured to output the at least one agricultural action.

In one aspect, the computing element may be configured to generate a second agricultural prescription based on the agricultural data generated by the information gathering component. The second agricultural prescription may be configured to be transmitted over the network.

In one aspect, the agricultural system may further include an agricultural device configured to receive the agricultural prescription and the second agricultural prescription over the network.

BRIEF DESCRIPTION OF THE DRAWINGS

The disclosure can be better understood with reference to the following drawings and description. The components in the figures are not necessarily to scale, emphasis instead being placed upon illustrating principles of the disclosure.

FIGS. 20-32 are multiple views illustrating various aspects of the present disclosure.

FIGS. 33A-33F is a chart illustrating one example of a manner of determining end soil moisture.

FIG. 36 is a chart illustrating another example of a manner of determining end soil moisture.

DETAILED DESCRIPTION

Figure 1:
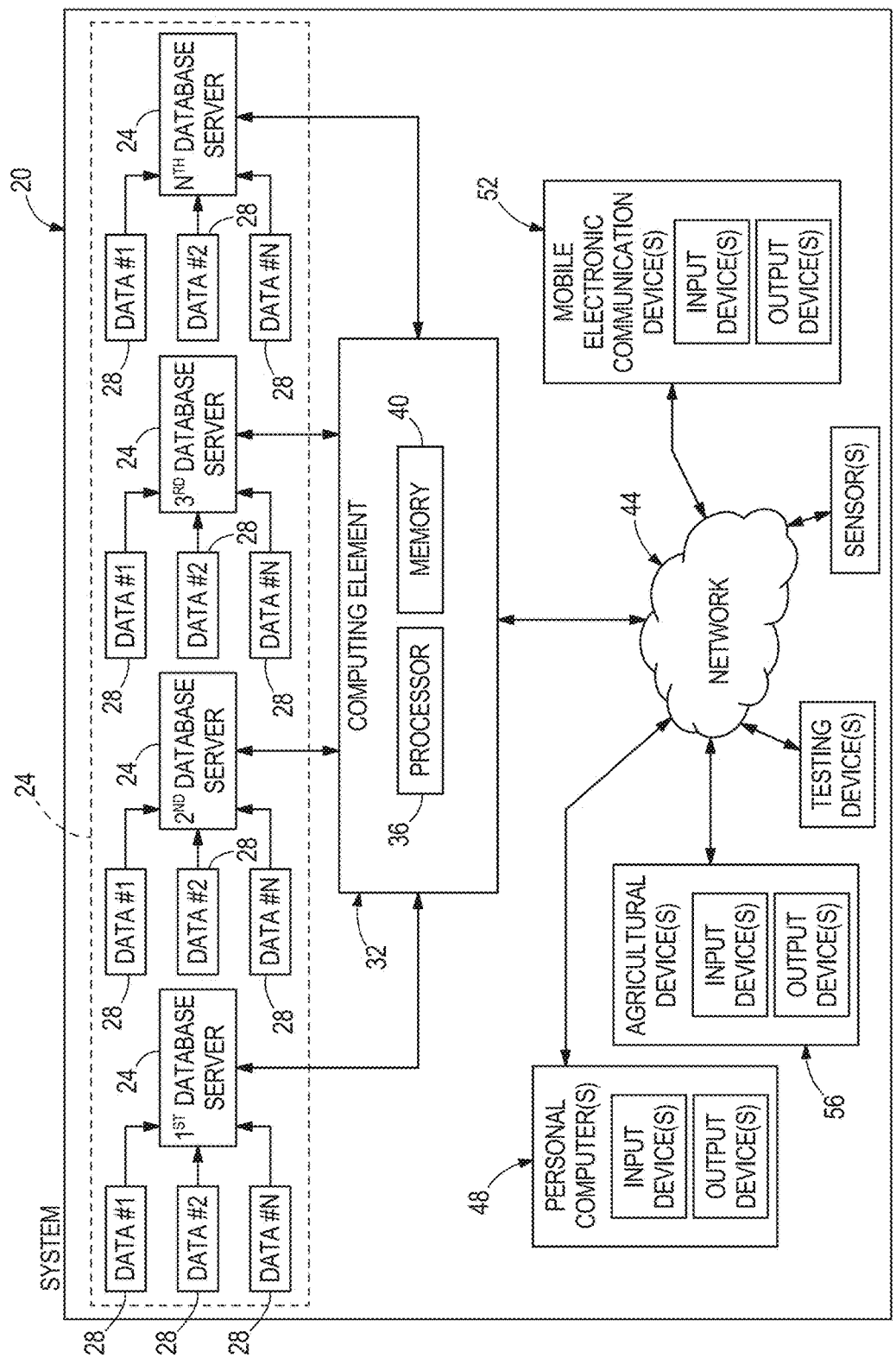
FIG. 1 is a block schematic diagram of one example of a system of the present disclosure, the system is configured to perform at least a portion of the functionality and methods of the present disclosure.

The present disclosure provides systems, methods and apparatuses for improving agronomics in one or more land areas of interest, which may be comprised of one or more fields including one or more crops. The systems, methods and apparatuses receive and/or generate large quantities of data and/or agronomic factors, analyze the data and/or factors, and provide agronomic information to users based on the received data and/or factors. The users may take appropriate action based on the information they receive or the information may be communicated directly to one or more agricultural device(s) where the agricultural device(s) may take appropriate action.

Many factors may impact and limit a crop's yield. The systems, methods and apparatuses of the present disclosure monitor, receive and/or generate agronomic data associated with the many factors that impact or limit a crop's yield and optimize a crop's yield based on the data. Agronomic data may be collected and/or generated in a variety of manners including, but not limited to, satellite, unmanned aerial vehicles, soil samples from soil sampling devices, cameras or other image capturing devices, ground sensors or sensors located anywhere or on anything relative to a crop or field, public weather data from public databases, seed characteristics, etc., and may be retrieved and/or generated by the systems, methods and apparatuses of the present disclosure. In some examples, agronomic data may also include economic data or economic related factors, indicators or variables such as, for example, seed costs, cost per seed, input costs (e.g., nitrogen, irrigation, pesticides, etc.), fuel costs, labor costs, etc. The systems, methods and apparatuses process the agronomic data to identify one or more limiting agronomic factors (i.e., the agronomic factor(s) preventing a crop from reaching a maximum yield). The systems, methods and apparatuses of the present disclosure are capable of receiving, determining, processing, analyzing, etc., a wide variety of agronomic data or factors. Examples of such data and factors include, but are not limited to: Growth cycle or growing period; sunlight; temperature; rooting; aeration; organic matter present in soil; water quantity; nutrients (NPK); water quality; salinity; sodicity; boron; chloride toxicities; pH; micronutrients; other toxicities; pests; diseases; weeds; flood; storm; wind; frost; seed variety characteristics; soil slope; corn moisture; weather patterns; economic factors; and other factors. Optimizing the limiting agronomic factor for a particular field may require multiple sets of data: 1) pre-planting information for that information, 2) an accurate map of actual plant progress, 3) harvest information and 4) post-harvest information. At least some of these agronomic factors will be described in more detail below to demonstrate exemplary principles of the present disclosure. Failure to address any particular agronomic factor with further specificity is not intended to be limiting upon the present disclosure in any manner. Rather, the present disclosure is intended to include all possible agronomic factors.

In one example, the growing cycle or growing period may be considered a period of time required for a crop to complete the states of a growth cycle. A growth cycle may include planting, establishment, growth, production of harvested part, and harvesting. Some crops are annual crops and complete their growth cycle once a year. In some examples, crops may be perennial crops and have growing cycles of more than one year. The growing period for annual crops may be the duration of the year when temperature, soil, water supply and other factors permit crop growth and development. The growing period is a major determinant of land suitability for crops and cultivars on a worldwide and continental scale. Growth cycles and growing periods differ around the World and are dependent upon the climates in those portions of the World.

Sunlight is another factor impacting growth of a crop. Sunlight may have three relevant aspects including: Day length; its influence on photosynthesis and dry matter accumulation in crops; and its effects on evapotranspiration. Sunlight levels may also be important in the drying and ripening of crops. The vegetative growth of most plants increases linearly with sunlight up to a limit beyond which no further increase occurs. As plant populations necessarily increase to keep up with increasing yield expectations, sunlight may become one of the most dominant growth-limiting factors. In one example, the systems, methods and apparatuses of the present disclosure may include one or more sensors for measuring sunlight. In another example, the systems, methods and apparatuses may retrieve data associated with sunlight from a data source such as, for example, a database, containing sunlight data.

Temperature is another factor that impacts growth of a crop. Growth of most crops ceases below a critical low temperature and crops experience adverse effects above very high temperatures (usually above 86-95 degrees Fahrenheit). Between a minimum temperature for growth and an optimum temperature for photosynthesis, the rate of growth increases more or less linearly with temperature. The growth rate may then reach a plateau within the optimum temperature range before falling off at higher temperatures. Temperature also interacts with sunlight. Growth potential for crops may be achieved with both sunlight and temperatures in optimal ranges. In one example, the systems, methods and apparatuses of the present disclosure may include one or more thermometers for measuring temperature. In another example, the systems, methods and apparatuses may retrieve data associated with temperature from a data source such as, for example, a database, containing temperature data.

Plants require water and nutrients, which are conveyed from the soil to the productive parts of the plants through roots. If root growth, or the development or function of a root system is impaired by adverse land characteristics (e.g., deficiencies of water, nutrients, inputs, etc., or excessive amounts of water, nutrients, inputs, etc.), the growth and yield of the crop may likewise be impaired. Root room is a space for root development and may be limited in a variety of manners including, but not limited to: Effective soil depth; volume percent occupied (or not occupied) by impediments; impenetrable (or penetrable) soil volume; or other manners. Root-occupied soil volume varies with time in the case of annual crops developing root systems from seedling establishment to plant maturity and this process can be slowed by mechanical impedance. Mechanical impedance relates to soil strength and, in some examples, an amount of root penetration force that roots must exert or resistance they must overcome to penetrate the soil. Root room and mechanical impedance produce differences in water, nutrient, and other input uptake by crops that affect final yields, production or quality. In one example, the systems, methods and apparatuses of the present disclosure may include one or more sensors for measuring root growth, root space, root room and/or root penetration. In another example, the systems, methods and apparatuses may retrieve data associated with root growth, root space, root room and/or root penetration from a data source such as, for example, a database, containing root growth, root space, root room and/or root penetration data. The systems, methods and apparatuses of the present disclosure may also include one or more devices for sampling root growth, root space, root room and/or root penetration.

Respiring plant roots consume large quantities of oxygen and obtain their oxygen mainly through the soil. Thus, an adequate supply of oxygen through the soil throughout the growing season is a requirement for many crops. Poor aeration may also lead to inefficient use of nitrogen applied in manures and fertilizers. Losses of nitrogen may occur from denitrification and leaching. Aeration may be addressed through permanent and/or temporary field drains. In one example, the systems, methods and apparatuses of the present disclosure may include one or more sensors for measuring oxygen content or consumption by roots. In another example, the systems, methods and apparatuses may retrieve data associated with oxygen content or consumption by roots from a data source such as, for example, a database, containing oxygen content or consumption by roots data. The systems, methods and apparatuses of the present disclosure may also include one or more devices for sampling oxygen content or consumption by roots.

Crop water requirement may be an amount of water necessary to meet maximum evapotranspiration rate of a crop when soil water is not limiting. Evapotranspiration is a rate of water loss through transpiration from vegetation, plus evaporation from the soil surface or from standing water on the soil surface. When irrigation is utilized, crop water requirements are typically calculated by determining a net irrigation water requirement and then gross irrigation water requirements. Net irrigation water requirement may be an amount of water required to meet the crop water requirement, minus contributions in the field by precipitation, run-on, groundwater and stored soil water, plus field losses due to run-off, seepage and percolation. Gross irrigation water requirement may be the net irrigation water requirement, plus conveyance losses between a source of water and a field, plus any additional water for leaching over and above percolation. In one example, the systems, methods and apparatuses of the present disclosure may include one or more sensors for measuring crop water requirements. In another example, the systems, methods and apparatuses may retrieve data associated with crop water requirements from a data source such as, for example, a database, containing crop water requirement data. The systems, methods and apparatuses of the present disclosure may also include one or more devices for sampling crop water requirements.

In some areas, crop water requirements may be partially provided by rain falling directly onto farmers' fields. In other areas, where measurable rainfall is less frequent and reliable, the crop water requirements may be provided by a combination of rainfall and/or irrigation through center pivot, drip tape or other irrigation methods. With respect to water requirements, not all the water received in a field is directly effective. Part of the water may be lost to run-off, deep percolation, or by evaporation of rain intercepted by plant foliage. Land characteristics such as slope, relief, infiltration rate, cracking, permeability and soil management may all influence crop water requirements.

Water quality becomes an issue when irrigation is utilized. Water quality criteria may be generally interpreted in the context of salinity, infiltration and toxicities and their effects on the soil. A salinity problem can occur if a total quantity of soluble salts accumulates in a crop root zone to an extent that affects yields. Excessive soluble salts in the root zone may be caused by irrigation water or indigenous salt, which may inhibit water uptake by plants. In such instances, the plants suffer from salt-induced drought. Infiltration problems occur when a rate of water infiltration into and through the soil is reduced (because of water quality) to such an extent that the crop is not adequately supplied with water, thereby resulting in reduced yield. Poor soil infiltration may also add to cropping difficulties through crusting of seed beds, waterlogging of surface soil and accompanying disease, salinity, weed, oxygen and nutritional problems. Toxicity issues usually relate to higher amounts of specific ions in the water, namely, boron, chloride and sodium. In one example, the systems, methods and apparatuses of the present disclosure may include one or more sensors for measuring water quality. In another example, the systems, methods and apparatuses may retrieve data associated with water quality from a data source such as, for example, a database, containing water quality data. The systems, methods and apparatuses of the present disclosure may also include one or more devices for sampling water quality.

Nutrients are another factor that impact crop yield. In one example, three major nutrients are commonly applied as fertilizers to a crop. These nutrients include: Nitrogen (N); Phosphorous (P); and Potassium (K). In other examples, other nutrients may be used as fertilizer. The mineral composition of plant dry matter as a measure of crop nutrient requirements necessitates regular sampling during the life of the crop to ensure accurate results. However, crop nutrient uptake may be taken as the nutrient content of the harvested crops, which may provide a guide as to the nutrients required to maintain soil fertility at about the existing level. Supplies of plant nutrients to replace those removed at harvest may come from, for example: Soil mineralization (i.e. the transformation of soil minerals or organic matter from non-available into available nutrients); manures and fertilizers; or fixation from the air. In one example, the systems, methods and apparatuses of the present disclosure may include one or more sensors for measuring nutrient levels in the soil. In another example, the systems, methods and apparatuses may retrieve data associated with nutrient levels from a data source such as, for example, a database, containing nutrient level data. The systems, methods and apparatuses of the present disclosure may also include one or more devices for sampling nutrient levels.

Of these exemplary nutrients, the availability of nitrogen may be a substantial factor affecting yields. Nitrogen fertilizers give fairly predictable yields where lack of nitrogen is a principal limiting factor. Several considerations in determining a quantity of nitrogen that should be applied to obtain a given yield are, for example: Amounts of nitrogen removed by the crop; initial nitrogen content of the soil; contribution from nitrogen fixation; and nitrogen losses due to leaching, denitrification, etc. The cost of applying fertilizer nitrogen may vary from land unit to land unit. Soils requiring high nitrogen inputs may be initially low in nitrogen, or may utilize nitrogen applications inefficiently due to leaching or other losses. In practice, however, farmers often use the same amounts of fertilizer on a given land unit, and yields from field to field may vary on account of different efficiencies of utilization.

Insufficient regard for potential pest, disease and weed problems commonly results in poor crop performance. These problems can come in the form of, for example: Wild animals; arthropods including insects and mites; parasitic nematodes; fungal pathogens; bacterial pathogens; virus diseases; among others. In reconnaissance studies these should be considered in selecting alternative land areas. Climate plays a significant role in the increased incidence of many fungal and bacterial leaf diseases. For example, humid sites may be more disease-prone since the number of hours during which the leaf surface is wet often encourages fungal and bacterial pathogens, and reduces the effectiveness of control measures. The impracticability of weed control during periods of wet weather on heavy soils restricts the range of crops that can be grown and weeds that are not a problem early in the life of a project may become so with time or vice versa. Poorly drained soils predispose certain crops to root and foot rots. Nematode problems may be more severe on sandy soils than on clay soils. In one example, the systems, methods and apparatuses of the present disclosure may include one or more sensors for measuring infestation or other crop problems. In another example, the systems, methods and apparatuses may retrieve data associated with infestations or other crop problems from a data source such as, for example, a database, containing infestation or other crop problem data. The systems, methods and apparatuses of the present disclosure may also include one or more devices for sampling infestation or other crop problems.

As one can see a variety of factors impact crop yield. It is important for the systems, methods and apparatuses of the present disclosure to consider as many factors as possible in order to optimize crop yield, reduce the cost associated with growing a crop, and reduce environmental impacts when growing crops. The following examples of systems, methods and apparatuses are provided to demonstrate principles of the present disclosure and are not intended to limit the present disclosure in any manner. Other examples and alternative systems, methods and apparatuses are possible and are intended to be within the spirit and scope of the present disclosure.

With reference to FIG. 1, one example of a system 20 of the present disclosure is illustrated. The system 20 is one example of many systems of the present disclosure and is not intended to limit the present disclosure in any manner. Rather, the exemplary system 20 is provided to demonstrate principles of the disclosure. The system 20 is capable of performing all the functionalities of the present disclosure and includes all the necessary hardware and software to achieve the functionalities of the present disclosure. While the present disclosure may describe in detail at least a portion of the hardware and software required to achieve the functionalities of the present disclosure, the present disclosure is not intended to be limited to only the hardware and software described and illustrated, but rather is intended to include any hardware and software required. If any such hardware and software may be omitted from the description and/or drawings, such hardware and/or software may be conventional items known to those skilled in the art and the omission of such items may be a result of their conventionality.

With continued reference to FIG. 1, the exemplary system 20 includes a plurality of databases 24 for storing a variety of types of data or information. The system 20 may include any number of databases 24 as represented by the three databases and an Nth Database. The databases 24 may relate to any aspect of agronomics. Each database 24 may pertain to a different characteristic of agronomics or multiple databases 24 may pertain to similar agronomic characteristics. In the illustrated example, each of the databases 24 is configured to receive and/or store any quantity of data 28 as represented by Data #1, Data #2 and Data Nth. The databases 24 may receive and/or store as few as one data input 28 or may receive and/or store any number of data inputs 28. Moreover, the data 28 received and/or stored by the databases 24 may pertain to any agronomic factor or data. In one example, the data 28 received and/or stored by each database 24 will relate to the agronomic characteristic associated with the database 24. For example, if the database 24 is a weather database, the data 28 received and/or stored by the database 24 will pertain to weather. Also, for example, if the database 24 is a soil database, the data 28 received and/or stored by the database 24 will pertain to soil.

The databases 24 are configured to store the received data 28 therein for use by a computing element 32. The computing element 32 communicates with the databases 24 to retrieve and send information or data as necessary. The computing element 32 may include any necessary hardware, software or any combination thereof to achieve the processes, methods and functionalities of the present disclosure. In one example, the computing element 32 is a web server and includes all the conventional hardware and software associated with a web server.

In one example, the computing element 32 may be comprised of one or more of software and/or hardware in any proportion. In such an example, the computing element 32 may reside on a computer-based platform such as, for example, a server or set of servers. Any such server or servers may be a physical server(s) or a virtual machine(s) executing on another hardware platform or platforms. The nature of the configuration of such server or servers is not critical to the present disclosure. Any server, or for that matter any computer-based system, systems or elements described herein, will be generally characterized by one or more processors and associated processing elements and storage devices communicatively interconnected to one another by one or more busses or other communication mechanism for communicating information or data. In one example, storage within such devices may include a main memory such as, for example, a random access memory (RAM) or other dynamic storage devices, for storing information and instructions to be executed by the processor(s) and for storing temporary variables or other intermediate information during the use of the system and computing element described herein. In one example, the system 20 and/or the computing element 32 may also include a static storage device such as, for example, read only memory (ROM), for storing static information and instructions for the processor(s). In one example, the system 20 and/or the computing element 32 may include a storage device such as, for example, a hard disk or solid state memory, for storing information and instructions. Such storing information and instructions may include, but not be limited to, instructions to compute, which may include, but not be limited to processing and analyzing agronomic data or information of all types. Such agronomic data or information may pertain to, but not be limited to, weather, soil, water, crop growth stage, infestation data, historical data, future forecast data, or any other type of agronomic data or information. In one example, the system's and/or computing element's processing and analyzing of agronomic data may pertain to processing and analyzing limiting agronomic factors obtained from externally gathered image data, and issue alerts if so required based on pre-defined acceptability parameters. RAMs, ROMs, hard disks, solid state memories, and the like, are all examples of tangible computer readable media, which may be used to store instructions which comprise processes, methods and functionalities of the present disclosure. Exemplary processes, methods and functionalities of the system 20 and/or computing element 32 may include determining a necessity for generating and presenting alerts in accordance with examples of the present disclosure. Execution of such instructions by the system 20 and/or the computing element 32 causes the various computer-based elements of the system 20 and the computing element 32 to perform the processes, methods and functionalities described herein. In some examples, the systems 20 and the computing elements 32 of the present disclosure may include hard-wired circuitry to be used in place of or in combination with, in any proportion, such computer-readable instructions to implement the disclosure.

In one example, to facilitate user interaction, collection of information, and provision of results, the systems 20 of the present disclosure may include one or more output devices such as, for example, a display device, though such a display may not be included with a server, which may communicate results to a client/manager station (via an associated user/client/manager interface) rather than presenting the same locally. User/client/manager stations may also include one or more input devices such as, for example, keyboards, touch screens, and/or mice (or similar input devices) for communicating information and command selections to the local station(s) and/or server(s).

In one example, the computing element 32 may include at least one conventional processor 36 and at least one conventional type memory 40. The memory 40 stores necessary data therein that may be retrieved by the processor 36 in order for the computing element 32 to perform the operations or functionalities of the present disclosure. The processor 36 may also store data as necessary in the memory 40 for later use. Functionalities or operations of the computing element 32 and the system 20 will be described in greater detail below.

With continued reference to FIG. 1, the computing element 32 is configured to communicate over one or more networks 44. In the illustrated example, only one network 44 is illustrated; however, the computing element 32 is capable of communicating over multiple networks 44. In examples where the computing element 32 may communicate over multiple networks 44, the computing element 32 may communicate over the networks 44 contemporaneously or independently (i.e., one at a time). The computing element 32 selectively communicates over a desired network 44 when communicating independently. The network 44 may be a wide variety of types of networks and the present disclosure contemplates using any type of network. For example, the network 44 may be one of an Internet, an intranet, a cellular network, a local area network (LAN), a wide area network (WAN), a cable network, or any other type of network that is capable of transmitting information, such as digital data, and the like. In examples where the system 20 includes multiple networks 44, the multiple networks 44 may be similar types of networks or the networks 44 may be different types of networks. For example, the system 20 may communicate over a cellular network and over the Internet.

Figure 3:
FIG. 3 is a front view of examples of devices that may be included in one or more of the systems, in this example the devices are a personal computer and a mobile electronic communication device.

The computing element 32 is configured to communicate data to a wide variety of devices over one or more networks 44 and any such devices are intended to be within the spirit and scope of the present disclosure. In the illustrated example, the computing element 32 is configured to communicate over one or more networks 44 with personal computers 48, mobile electronic communication devices 52, and agricultural devices 56. The mobile electronic communication devices 52 may be a wide variety of devices including, but not limited to, a personal desktop assistant (PDA), a portable computer, a mobile telephone, a smartphone, a netbook, a mobile vehicular computer, a tablet computer, or any other type of mobile electronic communication device. Examples of personal computers 48 and mobile electronic communication devices 52 are illustrated in FIG. 3. The agricultural devices 56 may be a wide variety of agricultural devices including, but not limited to, tractors, planters, harvesters, sprayers, any input application device, irrigation devices, soil sampling devices, agronomic sensors, etc. The computing element 32 is also configured to communicate over one or more networks 44 with a single device at a time or multiple devices contemporaneously or intermittently. For example, the computing element 32 may communicate with a user's smartphone over a cellular network. Also, for example, the computing element 32 may communicate with a tractor over a cellular network. Further, for example, the computing element 32 may communicate with a user's personal computer over the Internet and communicate with the user's smartphone over a cellular network.

The system 20 and computing element 32 are capable of performing a wide variety of functionalities or operations that improve agronomic conditions. For example, the computing element 32 receives one or more types of data from one or more databases 24, analyzes the one or more types of data and communicates data to one or more devices 48, 52, 56 over one or more networks 44 pertaining to the analyzed agronomic data. The data communicated to the one or more devices will assist with improving the agronomic conditions of a particular land area of interest that includes one or more fields and one or more crops. In one example, the communicated data may be viewed by a user, farmer, crop consultant, agronomist, etc. (collectively referred to hereafter as "user"), and the user may take action in accordance with the communicated data. In one example, the communicated data is communicated to one or more agricultural devices 56 and the one or more agricultural devices 56 may operate or be operated by a user in accordance with the communicated data. In one example, communicated data may be communicated to a device 48, 52 where a user may view the data in a visual format (see FIG. 3) and also be communicated to one or more agricultural devices 56. In this example, the user may take action based on the communicated data and the one or more agricultural devices 56 may operate in accordance with the communicated data.

Figure 2:
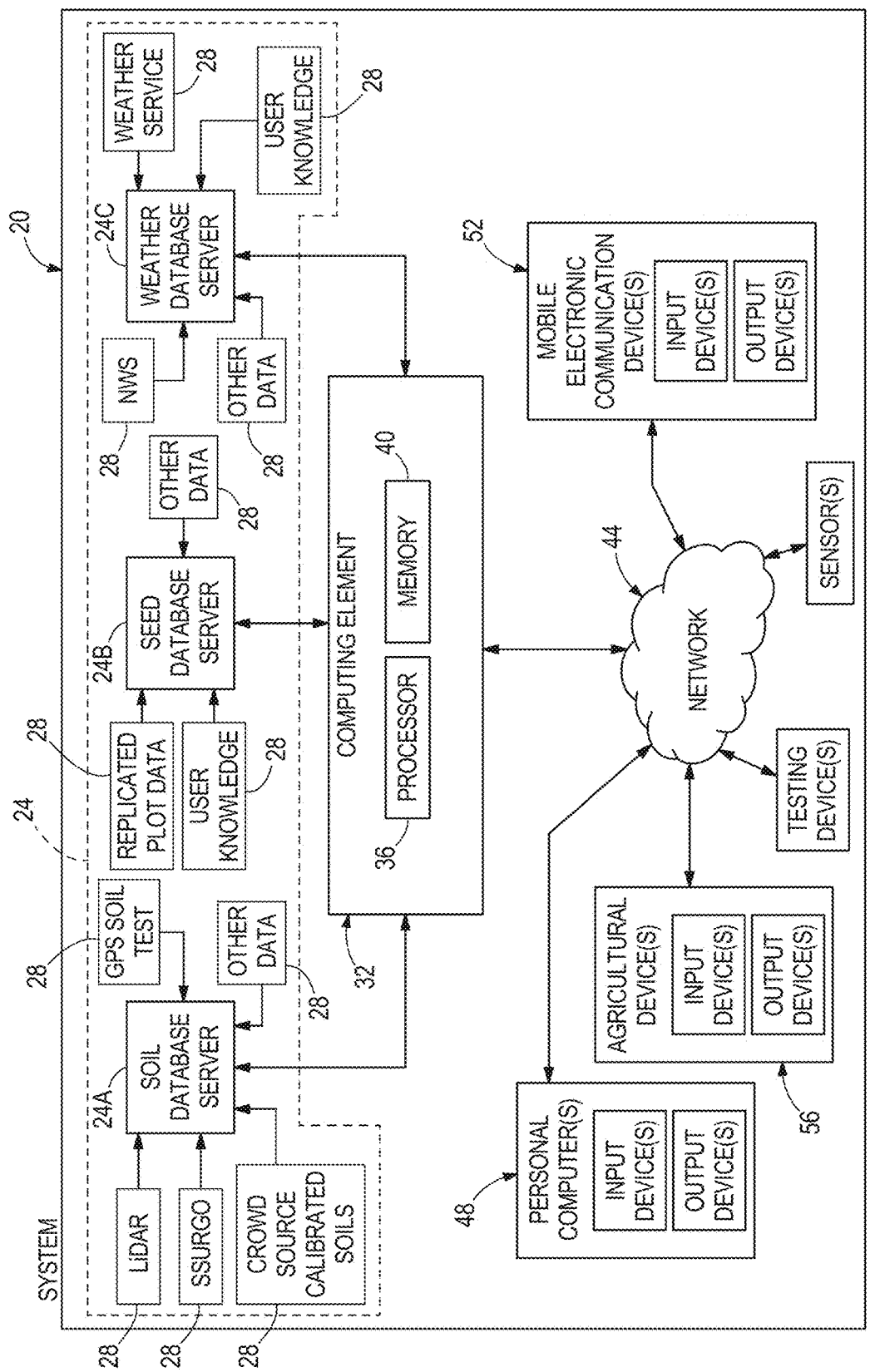
FIG. 2 is a block schematic diagram of another example of a system of the present disclosure, the system is configured to perform at least a portion of the functionality and methods of the present disclosure.

Referring now to FIG. 2, another example of a system 20 of the present disclosure is illustrated. The system 20 illustrated in FIG. 2 is one example of many possible systems of the present disclosure and is not intended to limit the present disclosure in any manner. Rather, the exemplary system 20 is provided to demonstrate principles of the disclosure. The system 20 is capable of performing all the functionalities or operations of the present disclosure and includes all the necessary hardware and software to achieve the functionalities of the present disclosure. While the present disclosure may describe in detail at least a portion of the hardware and software required to achieve the functionalities or operations of the present disclose, the present disclosure is not intended to be limited to only the hardware and software described and illustrated, but rather is intended to include any hardware and software required. If any such hardware and software may be omitted from the description and/or drawings, such hardware and/or software may be conventional items known to those skilled in the art and the omission of such items may be a result of their conventionality.

With continued reference to FIG. 2, the exemplary system 20 includes three databases 24A, 24B, 24C for storing a variety of types of data or information. The three databases include a soil database 24A, a seed database 24B and a weather database 24C. Each database 24A, 24B, 24C is configured to receive and store data 28 associated with the agronomic characteristic of the database 24A, 24B, 24C (e.g., soil, seed and weather, respectively). In this example, the soil database 24A may receive GPS soil test data, LiDar data, SSURGO data, crowd source calibrated soils data, and data from social media (e.g., FACEBOOK, TWITTER, INSTAGRAM, etc.). In one example, through the use of social media, peer users may compare soil, seed and weather information with others, including those other users who have land areas in relative proximity and therefore may be subject to similar soil, seed and weather conditions. In some examples, databases 24A, 24B, 24C may be supplemented with information provided by a social media. In this example, the system 20 is configured to allow one or more users to communicate information between one another that may be relevant to soil, seed and weather status, status updates of current crops for peer farmers, or prescriptions and strategies of peer farmers. On some occasions, the system 20 may receive data via a social network from other users and store said data in an appropriate database(s). In one example, pest problems on a nearby field operated by another farmer may be relevant to the user's fields; i.e., rootworm or aphids on a nearby field with a crop similar to a user's fields.

The seed database 24B may receive and store replicated plot data and user knowledge data. The weather database 24C may receive and store national weather service data, other weather service data (e.g., The Weather Channel data, Weather Underground data, etc.), and user knowledge data. The soil database 24A, seed database 24B and weather database 24C store this data 28 for retrieval by the computing element 32.

It should be understood that the data 28 described and illustrated in the context of this example are presented for exemplary purposes to demonstrate principles of the disclosure and are not intended to limit the present disclosure in any manner. Rather, any type of data associated with soil, seed and weather may be received and stored in the respective databases and all of such possibilities are intended to be within the spirit and scope of the present disclosure.

The databases 24A, 24B, 24C are configured to store the received data 28 therein for use by the computing element 32. The computing element 32 communicates with the databases 24A, 24B, 24C to retrieve and send data as necessary. The computing element 32 may include any necessary hardware, software and any combination thereof to achieve the functionalities of the present disclosure. In one example, the computing element 32 is a web server and may include all the conventional hardware and software associated with a web server. In one example, the computing element 32 may include at least one conventional processor 36 and at least one conventional type of memory 40. The memory 40 stores necessary data therein that may be retrieved by the processor 36 in order for the computing element 32 to achieve the functionalities or operations of the present disclosure. The processor 36 may also store data as necessary in the memory 40 for later use.

With continued reference to FIG. 2, the computing element 32 is configured to communicate over one or more networks 44. In the illustrated example, only one network 44 is illustrated; however, the computing element 32 is capable of communicating over multiple networks 44. In examples where the computing element 32 may communicate over multiple networks 44, the computing element 32 may communicate over the networks 44 contemporaneously or independently (i.e., one at a time). The computing element 32 selectively communicates over a desired network 44 when communicating independently. The network 44 may be a wide variety of types of networks and the present disclosure contemplates using any type of network. For example, the network 44 may be one of an Internet, an intranet, a cellular network, a local area network (LAN), a wide area network (WAN), a cable network, or any other type of network that is capable of transmitting information, such as digital data, and the like. In examples where the system 20 includes multiple networks 44, the multiple networks 44 may be similar types of networks or the networks 44 may be different types of networks. For example, the system 20 may communicate over a cellular network and over the Internet.

The computing element 32 is configured to communicate data to a wide variety of devices over one or more networks 44 and any such devices are intended to be within the spirit and scope of the present disclosure. In the illustrated example, the computing element 32 is configured to communicate over one or more networks 44 with personal computers 48, mobile electronic communication devices 52, and agricultural devices 56. Examples of personal computers 48 and mobile electronic devices 52 are illustrated in FIG. 3. Reference is made to the description presented above in connection with FIG. 1 pertaining to the devices with which the computing element 32 is configured to communicate, and all of such possibilities also apply to the devices associated with the system 20 illustrated and described in connection with FIG. 2.

The system 20 and computing element 32 are capable of performing a wide variety of functionalities or operations that improve agronomic conditions. For example, the computing element 32 receives one or more types of data from one or more databases 24A, 24B, 24C, analyzes the one or more types of data and communicates data to one or more devices 48, 52, 56 over one or more networks 44 pertaining to the analyzed agronomic data. The data communicated to the one or more devices 48, 52, 56 will assist with improving the agronomic conditions of a particular land area of interest that includes one or more fields and one or more crops. In one example, the communicated data may be viewed by a user and the user may take action in accordance with the communicated data or a user may operate the agricultural device in accordance with the communicated data. In one example, the communicated data is communicated to one or more agricultural devices 56 and the one or more agricultural devices 56 may operate in accordance with the communicated data. In one example, communicated data may be communicated to a device 48, 52 where a user may view the data in a visual format (see, e.g., FIG. 3) and also be communicated to one or more agricultural devices 56. In this example, the user may take action based on the communicated data and the one or more agricultural devices 56 may operate in accordance with the communicated data.

More specifically, for example, the computing element 32 may receive data from the soil database 24A, analyze the data 28 relating to soil and communicate data to one or more devices 48, 52, 56 over one or more networks 44 pertaining to the analyzed soil data 28. The soil data communicated to the one or more devices 48, 52, 56 may assist with improving agronomic conditions of a land area of interest, field or crop as they relate to soil. Also, for example, the computing element 32 may receive data from the seed database 24B, analyze the data 28 relating to seed and communicate data to one or more devices 48, 52, 56 over one or more networks 44 pertaining to the analyzed seed data 28. The seed data communicated to the one or more devices 48, 52, 56 may assist with improving agronomic conditions of a particular land area of interest, field or crop as they relate to seed. Further, for example, the computing element 32 may receive data from the weather database 24C, analyze the data 28 relating to weather and communicate data to one or more devices 48, 52, 56 over one or more networks 44 pertaining to the analyzed weather data 28. The weather data communicated to the one or more devices 48, 52, 56 may assist with improving agronomic conditions of a particular land area of interest, field or crop as they relate to weather. The computing element 32 may retrieve only one of soil, seed or weather data 28 at a time and analyze only the one retrieved data 28, or the computing element 32 may retrieve any number and combination of soil, seed and weather data 28. In examples where only one type of data is retrieved and analyzed, only that single criteria is contemplated to improve the agronomic conditions of a particular land area of interest, field and/or crop. In examples where more than one type of data is retrieved and analyzed, the multiple data may be contemplated in unison and their combined effect on agronomic conditions of a particular land area of interest, field and/or crop may be considered to improve the agronomic conditions.

In one example, the communicated soil, seed and/or weather data 28 may be viewed by a user and the user may take action in accordance with the communicated soil, seed and/or weather data 28. In one example, the communicated soil, seed and/or weather data 28 is communicated to one or more agricultural devices 56 and the one or more agricultural devices 56 may operate in accordance with the communicated soil, seed and/or weather data 28 or the user may operate the agricultural device 56 in accordance with the communicated soil, seed and/or weather data 28. In one example, communicated soil, seed and/or weather data 28 may be communicated to a device 48, 52 where a user may view the soil, seed and/or weather data 28 and also be communicated to one or more agricultural devices 56. In this example, both the user may take action based on the communicated soil, seed and/or weather data 28 and the one or more agricultural devices 56 may operate in accordance with the communicated soil, seed and/or weather data 28.

The system 20 and computing element 32 may be utilized in a variety of manners. In one example, the system 20 and computing element 32 may be used to perform pre-season crop planning. In another example, the system 20 and computing element 32 may be used to perform in-season monitoring and adjustment. The system 20 and computing element 32 may analyze and output or communicate data in a similar manner in both pre-season and in-season examples, but a difference between pre-season and in-season examples may occur depending on how the communicated data is utilized. For example, in pre-season crop planning, a user may input or retrieve various combinations of data for the computing element 32 to analyze and the outputted or communicated data may simply be viewed by the user and/or stored for later viewing or use, without actually taking action on a crop or with an agricultural device. For in-season scenarios, for example, actual data occurring in real time may be input into the computing element 32, the computing element 32 analyzes the data, outputs data to be viewed by a user, and the user may take action based on the outputted data or the outputted data may be communicated to an agricultural device to control operation of the agricultural device.

The data communicated to the user by the computing element 32 may have several benefits and assist the user in many ways whether the computing element 32 is used for pre-season crop planning or in-season adjustment. For example, the computing element 32 may analyze seed types or varieties to determine appropriateness of the user specified seed type or variety, determine the most appropriate planting date, determine the most appropriate seed rate (e.g., how many seeds to plant per acre), determine the most appropriate amounts of inputs to apply to a crop, determine which inputs to apply to a crop, determine most appropriate time to harvest the crop, improve crop yields by performing the preceding aspects, improves the efficiency of the planting process and reduces a user's cost by performing the preceding aspects, decreasing the impact on the environment from the planting process by performing the preceding aspects, among others.

In one example of pre-season and/or in-season crop planning, with reference to FIGS. 20-32, the system 20 and the computing element 32 may analyze all possible iterations of pre-season crop planning data, to solve for the ideal pre-season crop planning data, e.g., the highest possible crop yield or highest possible crop yield with lowest plant population. In another example, the system 20 and computing element 32 does not analyze all of the possible iterations but selects random combinations of pre-season crop planning data, establishes upper and lower limits for yield loss, and continues iterating until the dataset has been narrowed down to only a handful of combinations showing the highest possible crop yield at the lowest possible plant population.

In one example of in-season adjustments, the system 20 and the computing element 32 may analyze all possible iterations of agronomic factors, to solve for the limiting agronomic factor. In another example, the system 20 and computing element 32 do not analyze all of the possible iterations but select random combinations of agronomic factors, establish upper and lower limits for yield loss, and continue iterating until the dataset has been narrowed down to only a handful of combinations from which the user can identify the limiting agronomic factor.

As indicated above, the system 20 and computing element 32 of the present disclosure have a variety of features and functionalities. The following features and functionalities are not intended to be limiting upon the present disclosure, but rather are provided as examples to demonstrate principles of the present disclosure. Other features and functionalities are possible and are intended to be within the spirit and scope of the present disclosure.

In one example, a system 20 provides the ability for a user to upload data or information pertaining to a land area of interest. This land area of interest may be a single field, a plurality of fields, or other land area of interest. For purposes of this description and for simplifying the description, the phrase land area of interest will be referred to and can account for any size of land and any number of fields, including one field or a portion of a field.

In one example, to begin use of the system 20, data associated with the land area of interest must be introduced or uploaded into the system 20. The land data may be uploaded into the system 20 in a variety of manners. In one example, the user may input (via, e.g., a keyboard, mouse, touch screen, storage medium such as, for example, memory stick, or any other type of input device) data associated with the land such as, for example, a name of the farmer/grower, name of the farm, name of the land or field. Then the user may select a land area of interest (e.g., a common land unit) from a farm service agency (FSA) including field maps with the system 20. If the land area of interest includes more than one field, the user may select multiple land areas of interest from the FSA and such land areas of interest may be grouped together and associated with the data input by the user.

Figure 4:
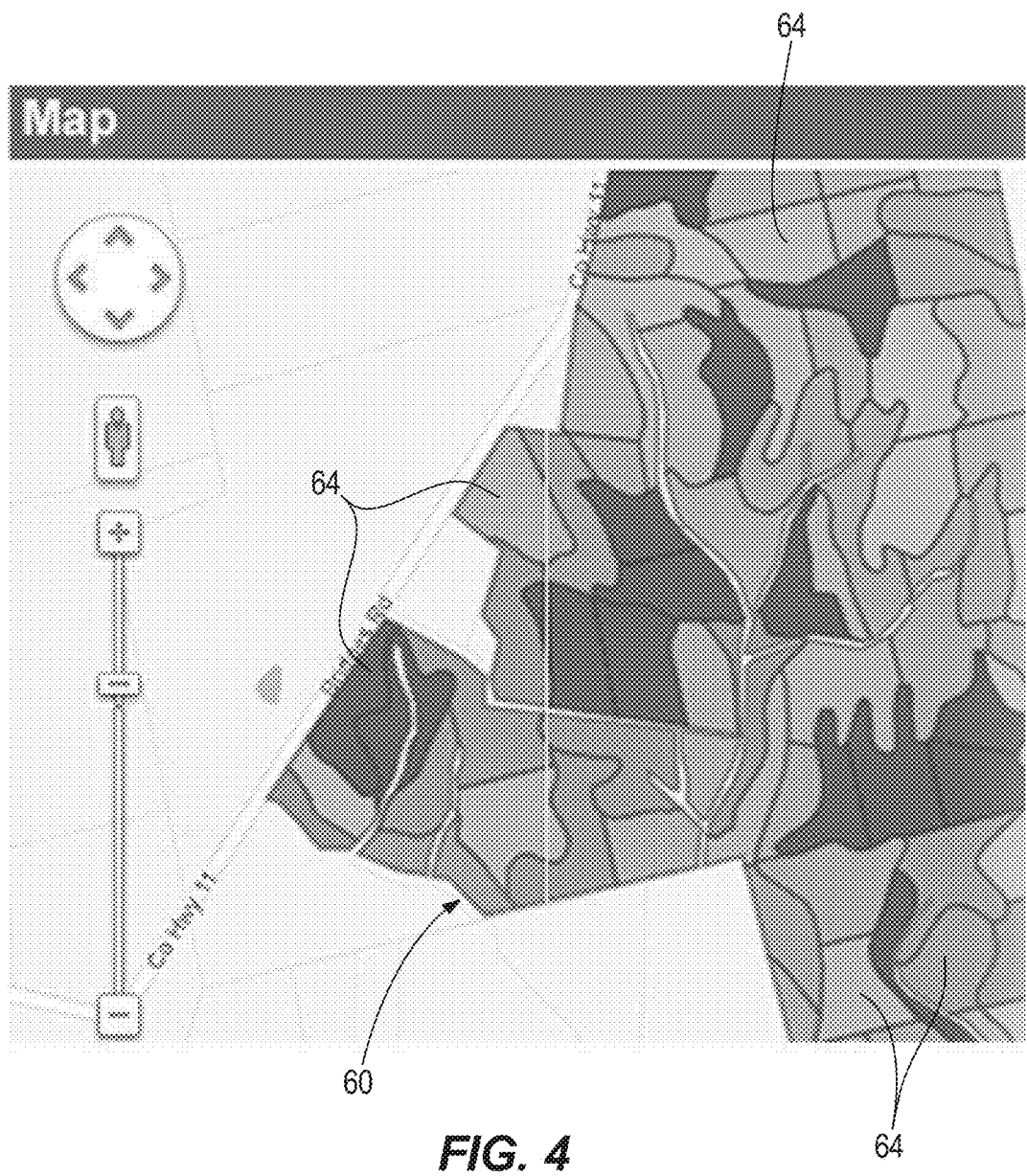
FIG. 4 is one example of a visual format of data communicated by one or more of the systems, in this example the visual format is a map including a plurality of zones color coded based on soil characteristics.

With reference to FIG. 4, one example of a land area of interest 60 is illustrated. In this example, the land area of interest 60 includes a plurality of zones 64. The different shading in the zones 64 may represent different characteristics between zones 64. The different characteristics may be a wide variety of characteristics and all of such possibilities are intended to be within the spirit and scope of the present disclosure. For example, the different characteristics may relate to, but are not limited to, differences in soil characteristics, plant population, etc. Such soil differences may pertain to, but are not limited to, quantity of organic matter present in soil, pH, phosphorous content, nitrogen content, potassium content, cation exchange capacity, slope, etc.

In another example, the land data may be uploaded into the system 20 in one or more bulk files such as, for example, one or more binary spatial coverage files. Such a bulk file includes all the necessary information associated with the land area of interest. In this example, the land data is exported to a binary spatial coverage file. Such exported information may include, but is not limited to, soil type layer or customized management zone with MUSYM (map unit symbol) attribute. Once such data is uploaded to the system 20, Geographic Information Systems (GIS) software may name each file within the bulk file by field name. GIS software may obtain desired land data and may include all the necessary land data for the land area of interest. When the land data is uploaded in bulk, the system 20 uses the file name to assign the field name by default. Names may be subsequently edited. If too many files are uploaded, the unwanted files may be subsequently deleted. The system 20 provides the ability to export all files, upload all files, then provides a preview where a user may select and delete unwanted files. Once the land files are uploaded, the system 20 links standard practices and weather forecasts, and determines land or field centroids for establishing virtual rain gauges with the uploaded land files. Field centroids are determined, in one example, by geographic midpoint. In one example, the system 20 may calculate the geographic midpoint by finding a center of gravity for the land area of interest. The system 20 may convert the latitude and longitude for each land area of interest into Cartesian (x,y,z) coordinates. The system 20 may multiply the x, y, and z coordinates by a weighting factor and added together. A line can be drawn from a center of the earth out to this new x, y, z coordinate, and the point where the line intersects the surface of the earth is the geographic midpoint. The system 20 converts this surface point into latitude and longitude for the midpoint. This is one example of the system 20 determining the centroid of a land area of interest. The system 20 may determine the field centroid in a variety of other manners including, but not limited to, triangle centroids, plumb line method, integral formula, balancing method, finite set of points, geometric decomposition, bounded regions, L-shaped, polygon, cone, pyramid, or other manners. The system 20 determining the field centroid allows a user to upload large quantities of files associated with a large number of fields or land area(s) of interest and identifying each of the fields or land area(s) of interest using the associated centroid(s) without the use of a land/field identifier (typically a 12 digit field code).

Standard practices may be farming practices complied over a period of time for a given area. Such practices may include planting dates, planting rates (e.g., seed rates), input applications such as, for example, nitrogen, average bushels per acre (e.g., 5 year average) or any other practices. The system 20 may generate the map illustrated in FIG. 4 by uploading data.

In a further example, the system 20 may communicate with a Geographic Information Systems (GIS) software to obtain desired land data. GIS software may include all the necessary land data for the land area of interest. The system 20 may generate the map illustrated in FIG. 4 by communication with and data received by GIS software.

In still another example, the system 20 may obtain land data from SSURGO, which includes digital soils data produced and distributed by the Natural Resources Conservation Service—National Cartography and Geospatial Center, and the user may customize the information with their own data. For example, customized data may include soil test data. In one example, the system 20 may include a soil testing device that can be used by a user to test the soil in order to determine soil characteristics. Soil test data may be uploaded to the system 20 in a binary spatial coverage file polygon format with an appropriate MUSYM for the land area of interest. The soil layer(s) associated with SSURGO may be swapped out with the customized uploaded soil test data. The system 20 may also generate the map illustrated in FIG. 4 by communication with and data received by a combination of SSURGO and customized data.

It should be understood that these examples of introducing land data into the system 20 are not intended to be limiting upon the present disclosure and, instead, the present disclosure is intended to include other manners of uploading land data into the system 20. It should also be understood that the system 20 may receive land data from a combination of these land data sources, in any combination, and all of such possibilities are intended to be within the spirit and scope of the present disclosure. It should further be understood that the system 20 may include one or more devices configured to generate or obtain data itself.

The system 20 and computing element 32 are configured to facilitate customization of a variety of features. The following examples of customizable features are provided to demonstrate principles of the present disclosure and are not intended to be limiting upon the present disclosure. Rather, other features may be customizable and all of such possibilities are intended to be within the spirit and scope of the present disclosure.

Customization of attributes or characteristics associated with the land area of interest provides more accuracy to the system 20. In some cases, land data obtained from one or more sources (e.g., GIS, SSURGO, etc.) may not be as accurate as possible for the land area of interest. The land area of interest may have different land characteristics from year to year or may have different characteristics compared to the neighboring land or other land grouped together in the one or more sources. Thus, it is desirable for the system 20 to provide as much customization as possible to reflect, as close as possible, the reality of the land area of interest.

Figure 5:
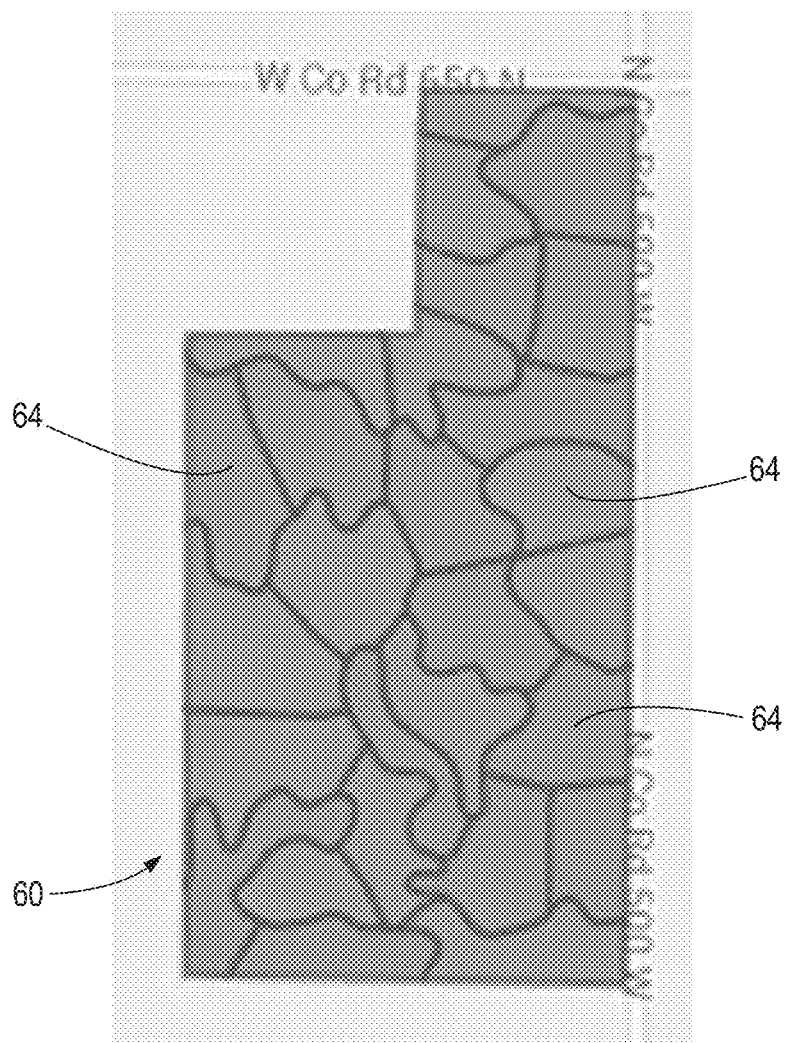
FIG. 5 is one example of a visual format of data communicated by one or more of the systems, in this example the visual format is a map including a plurality of zones color coded based on seed characteristics.
Figure 6:
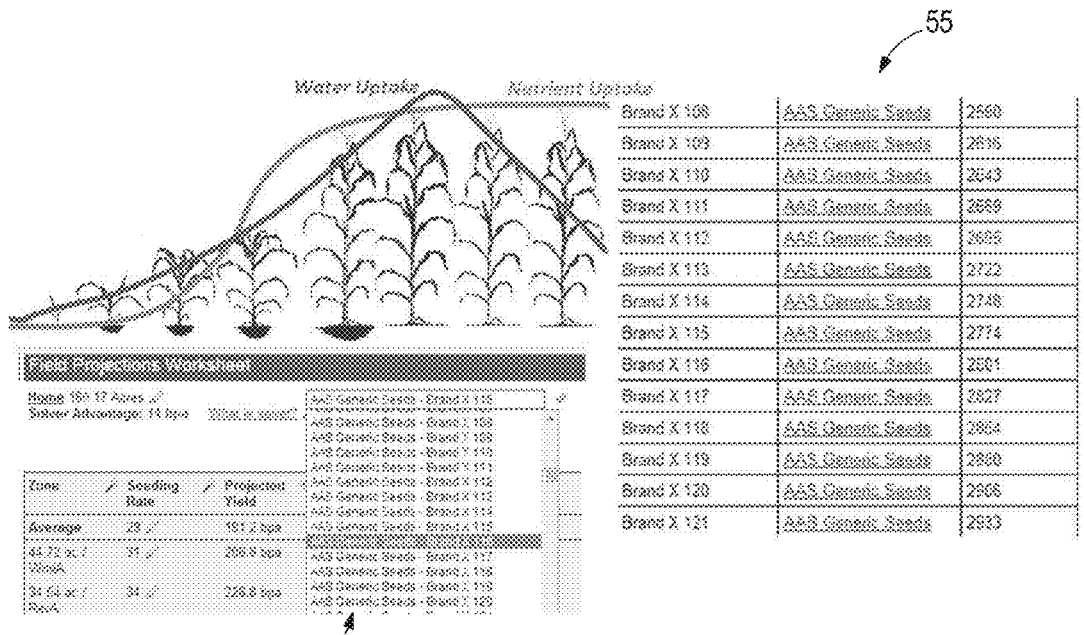
FIG. 6 is one example of a visual format of data communicated by one or more of the systems, in this example the visual format is a chart illustrating the impact of water, nutrient, uptake and seed varieties on projected yields.

In one example, the system 20 allows customization of a seed variety or seed type. With reference to FIG. 6, the system 20 displays a large quantity of seed varieties for a user to select from. The illustrated examples are only some of the many types of seed varieties and are not intended to be limiting upon the present disclosure. Rather, these examples of seed varieties are shown to demonstrate principles of the present disclosure. Each seed variety may include a seed profile, which may be comprised of a vast quantity of characteristics associated with that particular seed variety. Examples of seed profile characteristics include, but are not limited to, growing degree days, water demands, nutrient demands, relative maturity, days to maturity, projected yield, genetic information (e.g., resistance to Roundup—glyphosate, etc.), and others. Furthermore, seed profile characteristics themselves may be customizable based on the knowledge of the user. The user may alter any of the seed profile characteristics associated with a seed variety via the system 20 and altering of any such characteristic is intended to be within the spirit and scope of the present disclosure. With reference to FIG. 5, one example of a land area of interest is shown and is color coded based on the selected seed variety. The system 20 may color the land area of interest differently based on the variety of seed planted in the land area of interest. In the illustrated example, the same seed variety is planted over the entire land area of interest. In other examples, multiple seed varieties may be planted over a land area of interest and, in such examples, the land area of interest will include multiple colored zones to represent multiple seed varieties.

In one example, the system 20 allows customization of the growing degree days for seed variety. In one example, growing degree days is a heuristic tool useful in determining when a plant will reach various growth stages and expected water and nutrient usage. Growing degree days accounts for aspects of local weather and predict (and even control) a plant's pace towards maturity. Unless stressed by other agronomic factors, like moisture, the development rate from emergence to maturity for many plants depends upon the daily air temperature. Growing degree days is defined as the number of temperature degrees above a certain threshold base temperature, which varies among plant species. The base temperature is the temperature below which plant growth is zero or almost zero. The system 20 can calculate growing degrees each day as a maximum temperature plus the minimum temperature divided by 2 (or the mean temperature), minus the base temperature. The system 20 may accumulate growing degree days by adding each day's growing degrees contribution as the season progresses. Alternatively, the system 20 may utilize an hourly calculation instead of a daily (24 hour) calculation to allow for greater resolution. In an hourly calculation, such a calculation may include a weighted average calculated hourly and summed for the day. Further, the system 20 will account for the accumulation of growing degree days during the vegetative states and reproductive states of the crop. For example, the system 20 may consider the vegetative state of corn—planting, V2, V4, V6, V8, V10, V12, V14, V16—through the reproductive states—silks emerging, kernels in blister stage, dough state, denting, dented—until physiological maturity. The system 20 and the computing element 32 further utilize growing degree days in calculating the water requirements for a crop and whether water (or weather) is a limiting factor.

In one example, the system 20 allows customization of a seeding rate or amount of seed planted per a particular size land area (e.g., number of seeds planted per acre). The seeding rate may be altered at any level of land area of interest. For example, a user may alter, via the system 20, a seeding rate for the entire land area of interest, which may be comprised of numerous fields. Also, for example, a user may alter a seeding rate for each field within the overall land area of interest. Further, for example, a user may alter the seeding rate within a single field. That is, different portions or zones of the same field may have different quantities of seeds planted. As indicated above, the system 20 and the computing element 32 provide a user with the ability to select amongst a large variety of seeds.

In one example, the system 20 allows customization of a planting date. Altering planting dates for a crop may have a major impact on crop maturity and stress tolerance at different times throughout the growing season. Selecting an appropriate planting date may be dependent upon one or more growth conditions such as, for example, actual and/or historical weather, weather forecasts, seed variety, etc. In pre-season scenarios, a user may wish to try different planting dates to determine the impact on crop yield. Trying different planting dates will provide windows for best crop yields based on temperature forecasts, rainfall estimates, seed variety, seeding rate, etc., and will help forecast crop maturity and harvesting dates. For both pre-season and in-season scenarios, a user can input the actual planting date and forecast when the crop will reach full maturity and when the crop will be ready for harvesting.

In one example, the system 20 allows customization of irrigation. Some land areas allow for irrigation by having an irrigation system, whereas other land areas do not. Many types of irrigation systems may be utilized with the system 20. For example, irrigation systems may be above grade (e.g., center pivot systems) or below grade (e.g., drip tape systems or tiling systems). Tiling systems may be installed several feet below the ground surface and assists with draining the soil. Tiling systems may also be gated to allow a user to selectively open or close portions of the tiling system. The user may close the tiling system (or a portion or portions thereof) when dry conditions exist to help maintain water in the soil and the user may open the tiling system when wet conditions exist to help drain water from the soil. For those areas that allow for irrigation, the system 20 may be altered to account for rainfall and/or water added to the land area. For example, in dry years, it is desirable to add an amount of water to coordinate with the water demands of the seed variety planted in the land area. A user may input an amount of water added to the land area into the system 20 in a variety of manners. In pre-season scenarios, a user may tryout various levels of irrigation in the system 20 to determine the impact on the crop yield and select the best results for the upcoming season. These pre-season scenarios may also assist a user with making in-season adjustments as water quantities in the actual field may alter from the forecasted amounts. From the pre-season trials, the user will already know how the various levels of water impacted the crop and will be ready to make the in-season adjustment that results in a better crop yield. Additionally, for in-season scenarios, the user may input real-time water quantities into the system 20 to see the impact of such water quantities on the future crop yield. The user will then be able to make the appropriate changes in the field.

The system 20 and computing element 32 may be used in conjunction with various irrigation systems and allow for in-season adjustments. In one example, the system 20 and computing element 32 predict how a user irrigated a field. The system 20 analyzes actual weather data, historical weather data, standard farming practices for the area, seed variety, and planting date—also considering the growth cycle—to project how many inches of water a user would add on any given day.

Figure 7:
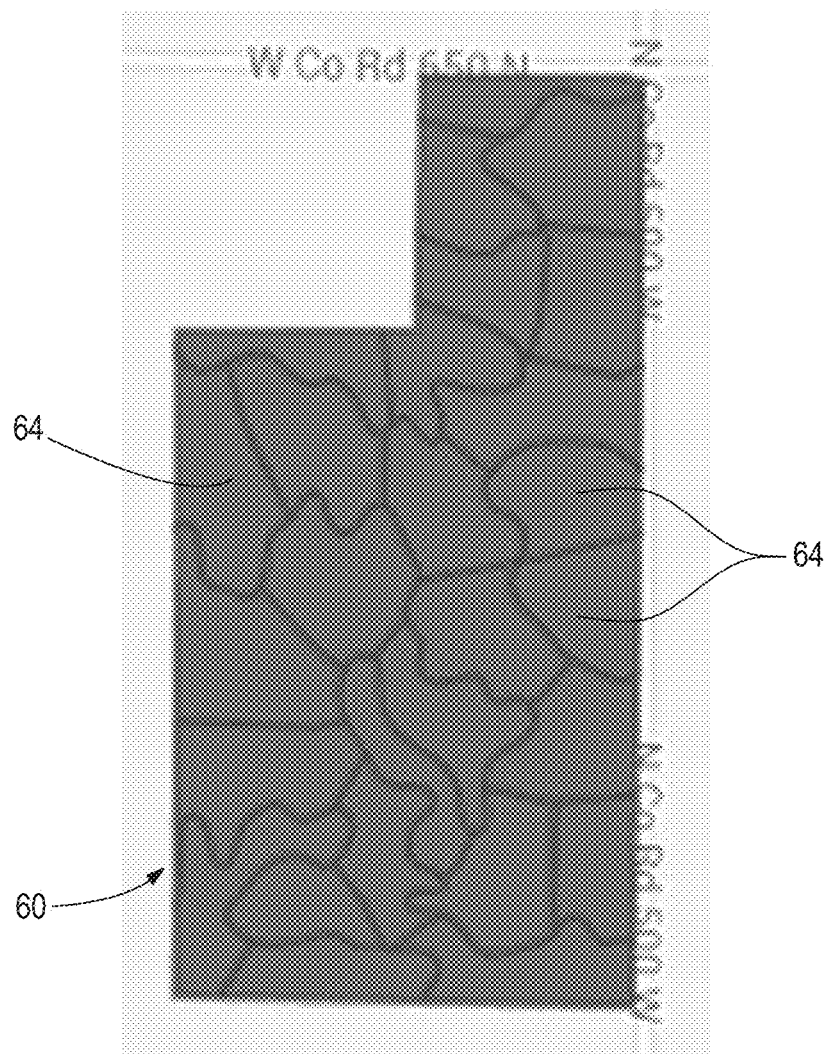
FIG. 7 is one example of a visual format of data communicated by one or more of the systems, in this example the visual format is a map including a plurality of zones color coded based on nitrogen characteristics.

In one example, the system 20 allows customization of a nitrogen rate or amount of nitrogen required for the land area of interest. In pre-season scenarios, a user may try different permutations of crop characteristics in the system 20 (e.g., soil, seed and weather) and the system 20 will provide an estimate of how much nitrogen to apply and when to apply the nitrogen. For in-season scenarios, the amount and time to apply nitrogen may change as other crop characteristics change (e.g., weather, water, temperature, etc.). The system 20 will adapt based on these changes and provide an updated amount and time to apply nitrogen, accounting for any previous applications of nitrogen in the pre-season, at the time of planting or at one or more growth stages. A user may also input the amount and time of applying nitrogen into the system 20 and the system 20 will determine the effect of such nitrogen application on the crop. With reference to FIG. 7, one example of a land area of interest is illustrated and is color coded by the system 20 based on a nitrogen rate. The system 20 colors the land area of interest differently based on the nitrogen rate in the land area of interest. In the illustrated example, the entire land area of interest has the same nitrogen rate (which is why the system 20 colors the entire land area of interest with a single color). In other examples, the land area of interest may have zones with different nitrogen rates and, in such examples, the system 20 will color the land area of interest with multiple colored zones to represent multiple nitrogen rates.

In one example, the system 20 allows customization of any input associated with growing a crop. In pre-season scenarios, the user may tryout any permutation of any input within the system 20 and the system 20 will determine the effects of the various permutations of inputs on the crop yield. The user may then use this information to make appropriate decisions for the upcoming growing season. For in-season scenarios, the user may customize and introduce into the system 20 any input associated with growing a crop with real-time data to closely reflect reality in the land area of interest. As indicated above, reality often times differs from forecasts and this customization provides the system 20 with the ability to correspond as close as possible with reality.

In one example, the system 20 allows customization of the soil type. Soil type may be customized via the system 20 if the soil types received from a $3^{rd}$ party source (e.g., SSURGO) are not accurate or are not sufficiently accurate to the soil type of the land area of interest. Soil type information of the land area of interest may be supplemented by performing a soil test to receive soil test data. The system 20 may include a soil testing device configured to test the soil and generate soil test data. Soil test data may pertain to various characteristics associated with soil including, but not limited to, pH, organic matter, phosphorous, nitrogen, potassium, cation exchange capacity (CEC), moisture holding capacity (inches moisture deficiency at planting, inches moisture holding capacity at root zone, 50% moisture holding capacity), etc. In one example, the system 20 analyzes the soil test data and replaces prior soil data with the soil test data to customize the soil type. In another example, the system 20 analyzes the soil test data, supplements the prior soil data with the soil test data to customize the soil type, and considers both the prior soil test data and the new soil test data in combination. In such an example, the new soil test data may supplement the prior soil test data in any manner such as, for example, replace the prior data in-part, replace the prior data in-whole, or not replace any prior data. The system 20 may customize soil type at any level with respect to land areas of interest. For example, the system 20 may customize at a zone by zone level, a field level, or a group level comprising a plurality of fields. Referring again to FIG. 4, in this example, a user may customize the soil type of each zone via the system 20 as desired.

Figure 8:
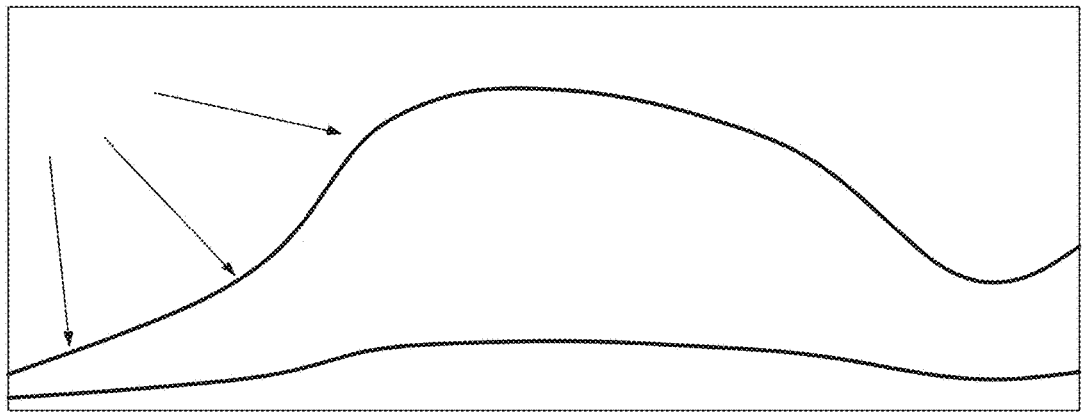
FIG. 8 is an exemplary chart demonstrating that land areas of interest have varying slopes.
Figure 9:
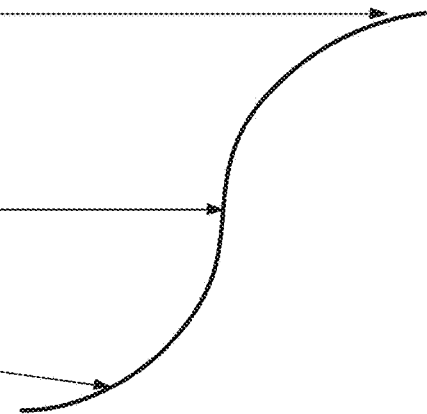
FIG. 9 is another exemplary chart demonstrating that land areas of interest have varying slopes and illustrated properties associated with the different slopes in this example, the properties determine whether the land is shedding water or collecting water and rates at which the land is doing so.

In one example, the system 20 allows customization of slope, which is the position, e.g., elevation, for a point in a land area relative to neighboring points in that same land area. Land is seldom flat or consistent across a land area of interest or field (see FIGS. 8 and 9). Thus, water and other inputs introduced onto or into the land area of interest may accumulate or shed differently based on the slope of the land area in particular zones. Water and other inputs are more likely to collect on flat zones and valleys, whereas water and inputs are more likely to run-off or shed from steep or inclined zones and hilltops. Thus, the slope is an important characteristic of the land area that impacts the performance of the crop. The system 20 may obtain and/or retrieve elevation information in a wide variety of manners and from a wide variety of sources. For example, the system 20 may obtain or retrieve elevation information from: databases containing LIDAR data maintained by the United States Geological Survey (USGS); IFSAR data; active sensors including SRTM; complex linear interpolation from contours (often including hydrography—LT4X); photogrammetrically complied mass points and break lines; digital camera correlation (usually from line camera such as Leica ADS40); polynomial interpolation from contours, mass points and break lines (ANUDEM); simple linear interpolation from contours (DLG2DEM and DCASS); manual profiling via a mechanical or analytical stero-plotter; gestalt photomapper II (electronic image correlation); topobathy merged data; among other manners and sources. In one example, the system 20 may include one or more devices that measure and/or determine slope itself/themselves.

In another example, the system 20 may calculate slope using the position of a given point relative to a set of points around that point within a land area to model water movement. In one example, the system 20 uses a raster data with a single elevation point and eight neighboring elevation data points, calculates the slope of each data point and then the maximum slope of each combination of two points. The relative position of the maximum slope is established and then determined to be negative or positive. A positive maximum slope means that the single elevation point is higher than a neighboring point; while a negative maximum slope means that the single elevation point is lower than a neighboring point. This relative position of the maximum slope is then stored and retrieved to create a high-resolution raster file. The high-resolution raster file is used to group relative positions into smoothed polygons; resulting in an appropriate resolution for controllers on agricultural devices, e.g., a rate controller for a sprayer. After the system 20 and computing element 32 determine the slope for a land area or land areas, the land areas may be divided or grouped into different zones and those zones collectively may differ from one another in slope. The slopes within a land area though may be differing or similar. In one example, the slope within a land zone is relatively uniform and similar. For example, the zone may be flat while another zone may be steep.

The system 20 may determine and utilize slope in other manners. In one example, a user may initiate (e.g., opt in) the process. The process may be hosted in a virtual server environment (e.g., a Rackspace, etc.) and the user may provide data to the system 20. The user may provide data to the system 20 in a variety of manners. In one example, the user provides one or more binary spatial coverage files (e.g., shape files, etc.) indicating boundary and map coverage (e.g., SSURGO) from a source (e.g., Surety, a GIS system, etc.). The system 20 may locate and extract elevation data based on the user's provided data once the user provided data is received by the system 20. The system 20 may receive the elevation data from a variety of sources (as indicated above). The system 20 and computing element 32 calculate or determine the slope as a percent slope (e.g., rise/run×100%). The sign of the slope indicates a curvature condition of the soil. For example, a positive (+) slope coordinates with a hilltop, which indicates increased slope rate downhill, and a negative (−) slope coordinates with a valley, which indicates decreased slope rate downhill. Slopes may be segmented, categorized or classified into any number of ranges, categories, classes or groups. For example, ranges may be established and any slope falling between thresholds of a particular range would be associated with that range, category, class or group. In other examples, each slope may be its own category, class or group, thereby providing as many classes, categories or groups as the number of determined slopes.

The following example is presented to demonstrate principles of the present disclosure and is not intended to be limiting. In this example, the system 20 utilizes the following classes, categories or groups, which are defined by the following ranges:

| | |
|---|---|
| −18% | slope <= −18 |
| −16% | −18 < slope <= −14 |
| −10% | −14 < slope <= −7 |
| −4% | −7 < slope <= −2 |
| 0% | −2 < slope <= 2 |
| 4% | 2 < slope <= 7 |
| 10% | 7 < slope <= 14 |
| 16% | 14 < slope <= 18 |
| 18% | 18 < slope |

Slopes associated with the −4%, −10%, −16% and −18% classifications are characterized as valleys and are configured to catch or collect water, whereas slopes with the 4%, 10%, 16% and 18% classification are characterized as hilltops and are configured to allow water to runoff or otherwise lose water. Slopes in the 0% classification are characterized as flat and water is neither running-off nor collecting due to these slopes.

In one example, once the system 20 determines and categorizes the slopes, the system 20 generates a binary spatial coverage file using the slope data and sends the binary spatial coverage file to a specified location within the virtual server environment. In another example, a KML file may also be exported or sent from a GRASS (Geographic Resources Analysis Support System) VM. In a further example, binary data may be passed to or received by the system 20. The system 20 may then send ASCII data (e.g., KML, JSON, WFS, WMS, etc.) to a web server. The system 20 may then output a polygon binary spatial coverage file coverage similar to a SSURGO map to a web server with the additional calculated slope data. The slope data (e.g., on the server side) may be leveraged while performing final calculations in the system 20. Now that the slope has been calculated, the system 20 may determine a virtual rain gauge that accurately determines how much water is in the soil after accounting for water run-off or collecting. The virtual rain gauge will have a higher water value (e.g., rainfall value) than the actual amount of rainfall for soil having negative slopes (due to collecting) and the virtual rain gauge will have a lower water value (e.g., rainfall value) than the actual amount of rainfall for soil having positive slopes (due to run-off). The water value of the virtual rain gauge may be equal to the actual amount of rainfall for soil having a slope in the 0% category since the soil is substantially flat, thereby eliminating any run-off or collecting. Once the system 20 determines the water value associated with the virtual rain gauge, the system 20 may perform other steps in the disclosed processes using the water value (e.g., determining projecting yield, limiting factor, seed rate, nitrogen rate, etc.). Thus, the system 20 is capable of providing more accurate results due to the consideration of soil slope and its impact on water distribution.

The following is another example of the system 20 determining a slope and coordinating the slope with a user's desired zone(s), field(s), or with any land area of interest. The system 20 receives, from a user, a spatial map of their land area of interest as a set of soil zone polygons that are clipped to a boundary as a binary spatial coverage file. The binary spatial coverage file may have a variety of forms. In one example, the binary spatial coverage file is in WGS-84 spherical coordinates (i.e., latitude and longitude coordinates). The system 20 imports soil zone data from one of a variety of sources (as described elsewhere herein) into a GIS environment of the system 20. The system 20 projects the soil zone data into a planar map projection (i.e., a soil layer) in distance units and checks and cleans the geometry topology. The system 20 defines a buffer layer based on the soil layer to clip elevation data from a U.S. national elevation dataset (NED). In some examples, the buffer layer may be larger than the user's inputted zone(s), field(s) or land area of interest. The system 20 calculates a slope-signed raster layer from an elevation layer. In this step, the system 20 may determine whether the slope is positive, negative or zero (flat). The system 20 may vectorize the raster slope data. In this step, the system 20 may apply a predetermined set of rules (e.g., categorization, grouping or classification of slopes). The system 20 may clean up and smooth resulting zone polygons. Clean up may pertain to areas within a zone that are irregularities or errors as compared to surrounding areas within the zone. Smoothing of the zone polygons may be performed for aesthetic purposes to increase user understanding and experience. Such clean up and smoothing may also be performed to improve performance of a monitor on which the resulting data and associated image may be displayed. The system 20 overlays the slope zone polygons on the soil zones inputted by the user to create new zones that are subdivisions of the inputted soil zones. That is, the lower quantity of inputted soil zones are further divided to provide multiple new zones within each soil zone based on slope of the soil. The system 20 projects the new soil zones as spherical coordinates (e.g., latitude and longitude coordinates), cleans-up the geometry of the projection, and writes the file to a binary spatial coverage file. Some monitors only work with latitudinal and longitudinal coordinates so the system may convert the outputted file to latitudinal and longitudinal coordinates.

In general, the slope of any land area of interest or zone impacts water distribution throughout the zone. The system 20 may determine the slope's impact on water distribution in a wide variety of manners and all of such manners are intended to be within the spirit and scope of the present disclosure. Some exemplary manners of slope's impact on water distribution are described above. The following are additional manners of slope's impact on water distribution.

In one example, the system 20 utilizes at least one process, such as, for example, an algorithmic function, to determine an influence of slope on water distribution and determine soil moisture for a given point. In another example, the system 20 utilizes a variety of processes, such as, for example, algorithmic functions, to determine an influence of slope on water distribution and determine soil moisture for a given point. In one example, the system 20 may determine the soil moisture at a given point by considering the slope and an amount of rainfall at the given point. If the slope at that point is positive, which indicates an increased slope rate downhill, the system 20 uses a first process, such as, for example, a first algorithmic function, to determine water distribution. If the slope at that point is negative, which indicates a decreased slope rate downhill, the system 20 uses a second process, such as, for example, a second algorithmic function, to determine water distribution. The system 20 may use any number of process, such as, for example, algorithmic functions, to determine slope's impact on water distribution. The system may also consider other factors or variables in determining slope's impact on water distribution such as, for example, soil type, crop age, seed variety, duration of weather events, etc.

The system determines soil moisture at a variety of points by considering water distribution at those points and may utilize the soil moisture of those points in a variety of manners. The system may determine soil moisture for any number of points within a zone (including only one point), a plurality of zones, a field, a land area of interest, etc. In one example, the system utilizes the soil moisture of the point(s) to determine an agronomic limiting factor. The limiting factor may be determined for a single point, a zone, a plurality of zones, a field, a land area of interest, etc. Determining the limiting factor utilizing an accurate soil moisture that considers soil slope will assist a user in a variety of manners such as, for example, producing a higher or highest possible crop yield, a highest crop yield with a lowest seed or plant population, a highest yield at a lowest cost, etc. In one example, the system may determine a quantity of water required to move the seed population higher to achieve higher projected crop yields. In another example, the system may determine how many inches of rainfall (or water from another source) is required to move the seed population higher or lower in any desired increments (e.g., 1000 seeds) to achieve higher projected crop yields. For example, the system may decrease a total planting population from 34,000 seeds per acre to 33,000 seeds per acre based on soil moisture and provide recalculated projections on crop yield.

Figure 10:
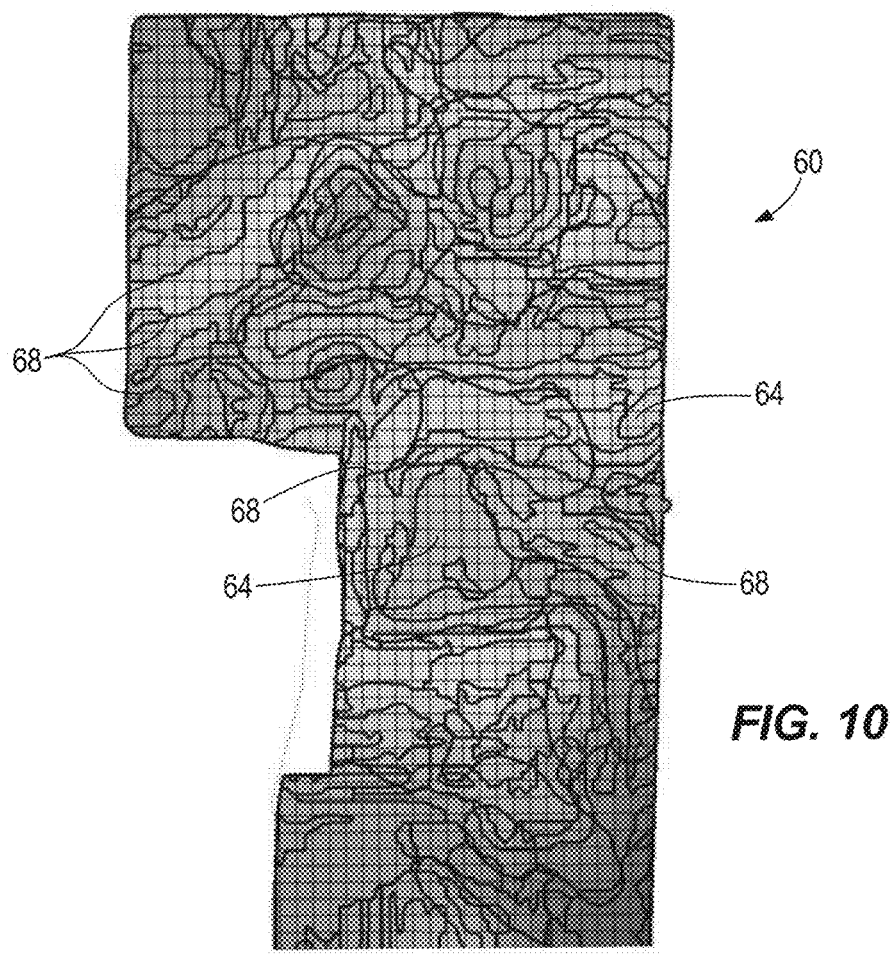
FIG. 10 is one example of a visual format of data communicated by one or more of the systems, in this example the visual format is a map including a plurality of zones color coded based on soil characteristics and contour lines for illustrating different slopes.
Figure 11:
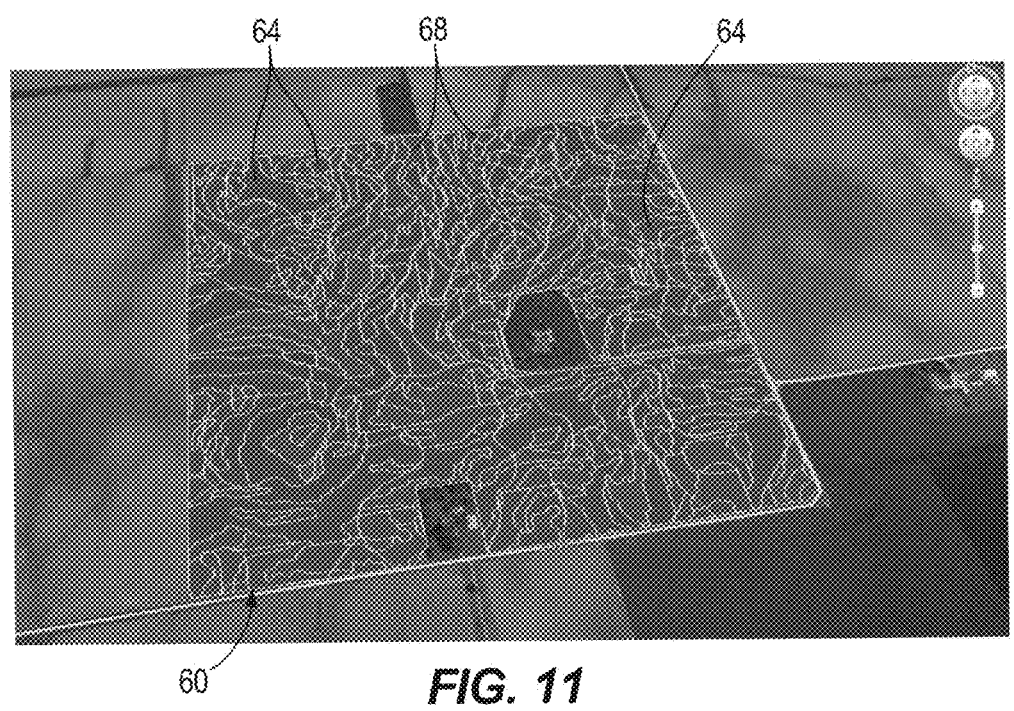
FIG. 11 is one example of a visual format of data communicated by one or more of the systems, in this example the visual format is a map including a plurality of zones color coded based on soil characteristics and contour lines for illustrating different slopes.
Figure 12:
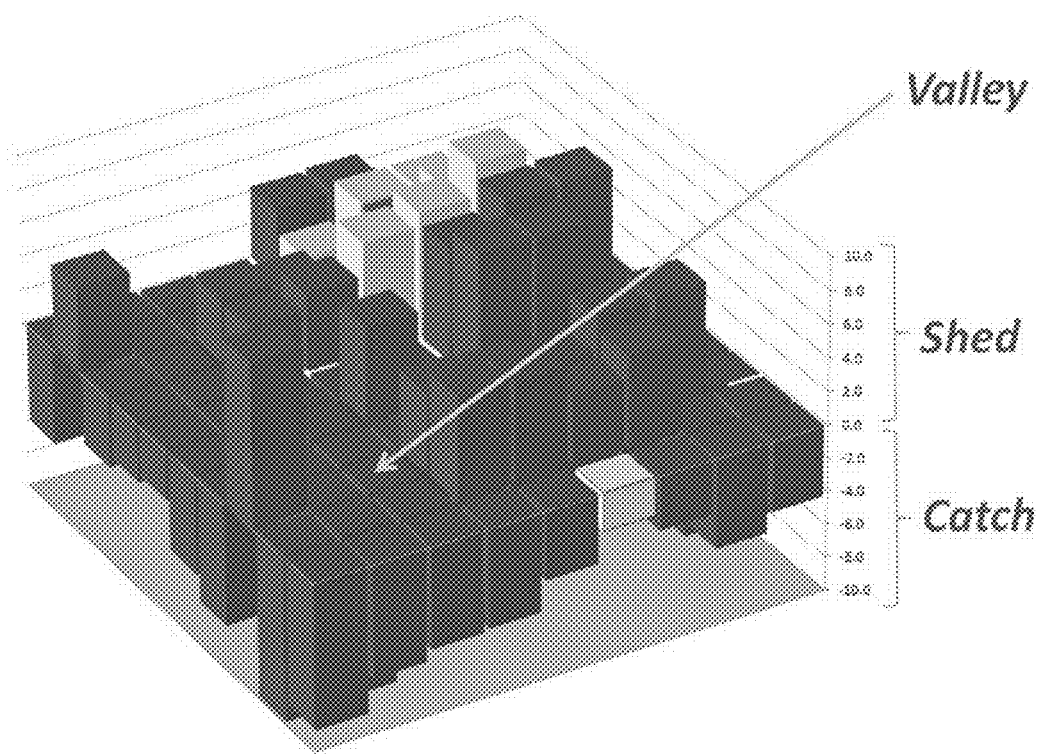
FIG. 12 is one example of a visual format of data communicated by one or more of the systems, in this example the visual format is a bar graph including a plurality of bars of varying heights for illustrating different slopes.
Figure 13:
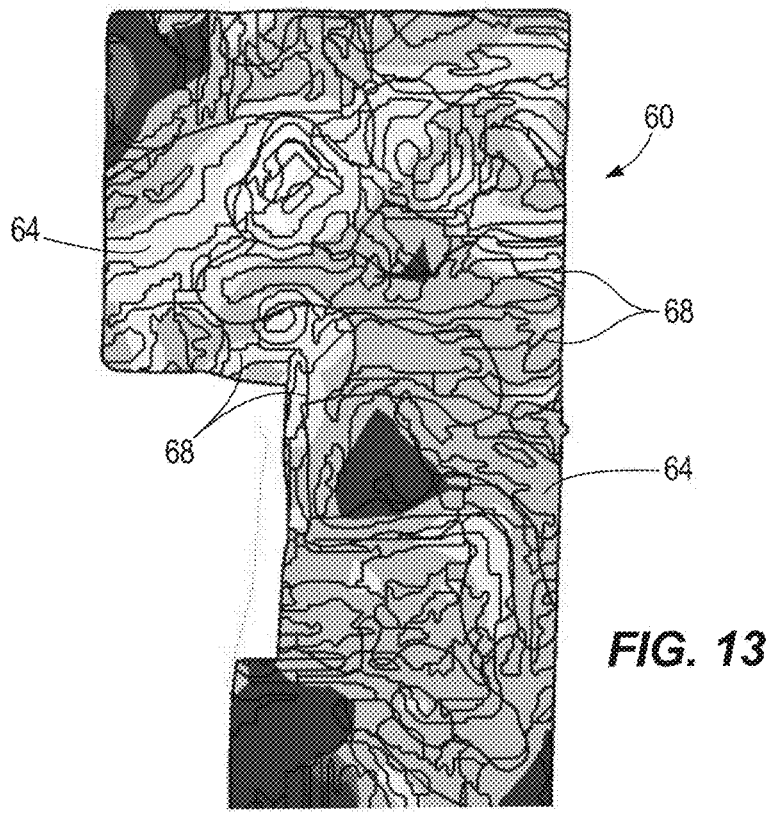
FIG. 13 is one example of a visual format of data communicated by one or more of the systems, in this example the visual format is a map including contour lines for illustrating different slopes and a plurality of zones color coded based on water flow of the land area of interest.

The system 20 and the computing element 32 may generate maps or illustrations of land areas of interest and incorporate slope into the land areas of interest. For example, with reference to FIGS. 10 and 11, these exemplary maps include zones, associated soil properties, and slope of the land. The soil properties are identified by various greyscale colors and the slope is identified by the dark lines overlaying the greyscale coloring. The system 20 may represent slope in a variety of manners, but, in these illustrated examples, the system 20 represents slope using contour lines 68 in topographical maps. Alternatively, with reference to FIG. 12, the system 20 may represent slope in other manners such as, for example, a 3D-bar graph. All of these land characteristic are important to the analysis performed by the system 20 and the computing element 32. Actual land slopes present in the land area of interest may differ from the slopes retrieved from other sources. Thus, the system 20 allows a user to customize the land slope by inputting actual land slopes of the land area of interest. The system 20 allows alteration of slopes at a variety of levels including, but not limited to, a field-by-field level, a zone-by-zone level, or the user may alter slopes, via the system 20, within a single zone and as a result create new zones with different slopes within a single zone or a single zone with similar slopes within that zone. With reference again to FIG. 10, the slopes in this exemplary map may be altered at any level (e.g., at the field level, at the zone level, or even within a single zone). With reference to FIG. 13, the land slope impacts water flow on a land area of interest. The various greyscale colors included in FIG. 13 demonstrate the areas where water accumulates and where water sheds. In one example, darker colors may represent areas where more water accumulates and lighter or white colors may represent where water sheds.

In one example, the system 20 allows customization of the weather. In the pre-season, the system 20 may run a variety of scenarios based on historical weather patterns and/or on weather forecasts for the upcoming year. A user may alter the weather in the system 20 to determine how various weather conditions impact crop performance. The system 20 allows alteration of many weather characteristics which include, but are not limited to, rainfall, temperature, humidity, pressure, sunlight, wind, or any other weather characteristic. For in-season scenarios, a user may alter the weather characteristics within the system 20 to reflect real-time weather data that corresponds more closely to reality rather than forecasts. Furthermore, the system 20 and the computing element 32 provide the ability to customize the weather to reflect weather conditions associated with an El Niño year or a La Niña year. El Niño and La Nina years have different weather patterns and weather characteristics. These differences can greatly affect a crop's growth. Thus, a user may customize the weather of the system 20 and the computing element 32 by selecting either an El Niño year or a La Nina year. The system 20 and the computing element 32 will perform their functionalities or operations with consideration of the selected weather characteristics.

Figure 14:
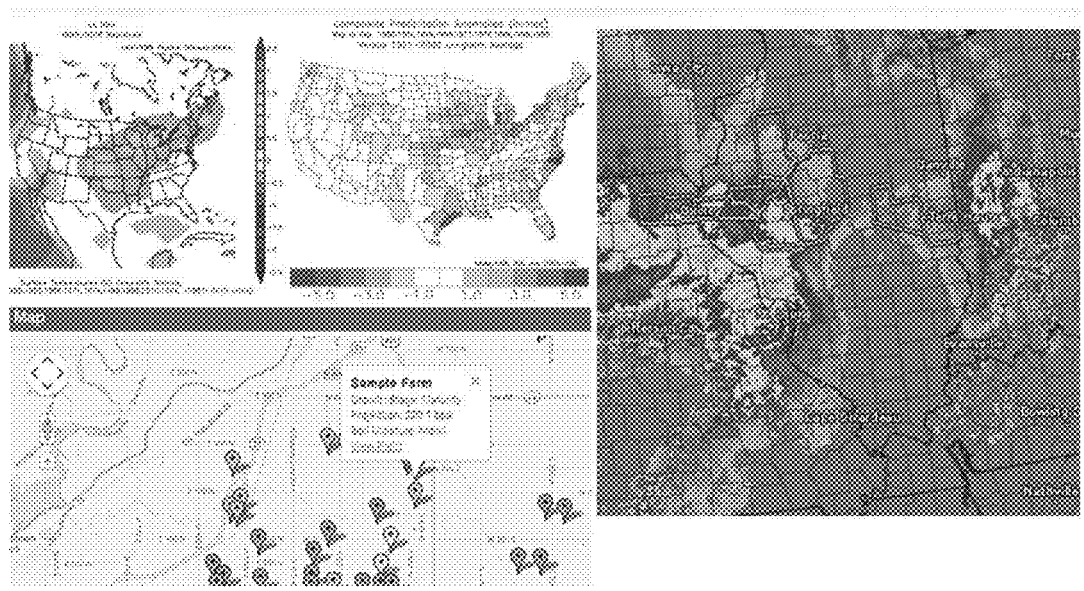
FIG. 14 is one example of a visual format of data communicated by one or more of the systems, in this example the visual format includes a plurality of maps illustrating weather data.

With reference to FIG. 14, a plurality of exemplary weather maps are illustrated and may be relied upon by the system 20 and the computing element 32 to perform the desired functionalities or operations of the system 20 and the computing element 32. These examples of weather maps illustrate various types of weather maps that the system 20 and the computing element 32 may utilize and they contain various types and quantities of weather information. Additionally, these exemplary weather maps may either be historical weather maps or future weather forecasts. The system 20 and the computing element 32 use this weather information to determine and/or project crop yields (see bottom left map in FIG. 14) for one or a plurality of land areas of interest.

The system 20 may facilitate customization of any number of the above characteristics in any combination and all of such possibilities are intended to be within the spirit and scope of the present disclosure. For pre-season crop planning, customizing the various characteristics in different permutations provides the user with the ability to forecast and select the proper crop to plant in the upcoming season.

Selecting the proper crop is much more difficult than just planting the same crop that was planted last year, which is the case for many farmers. Many seed varieties exist that have various demands (e.g., water demands, sunlight demands, nutrient demands, etc.). Since soil characteristics and weather patterns differ from year to year, the system 20 provides a user with the ability to consider these changes and select the proper seed variety, amount and type of inputs, etc., for the upcoming year. For in-season crop management, growing conditions alter along the way such as, for example, nutrient requirements, temperature, rainfall, other weather conditions, water demands, etc., and the system 20 provides the user with the ability to update a wide variety of growing conditions in order to modify the forecasted crop performance to reflect reality. This enables a user to make adjustments in the field (e.g., irrigation, nutrient increase or decrease, other input increase or decrease, harvest sooner or later, etc.) based on the real conditions in the field.

In addition to the above, in one example, the system 20 allows for customized slope and weather data to provide a soil moisture. Soil moisture may be determined at any time increment such as, for example, by the minute, hour, day, week, or any other increment of time. In the illustrated and described example, soil moisture will be determined on an hourly basis and will be referred to as hourly soil moisture. It should be understood that the present example is provided to demonstrate principles of the present disclosure and is not intended to be limiting.

The hourly soil moisture may be established for every zone or by specific zone. Such zones may be established in a variety of manners. In one example, a zone may be an entire field. In another example, a zone may be defined by soil type and a field may include a variety of zones. In a further example, a zone may be defined by slope and a field may include a variety of zones. In still another example, a zone may be defined by considering both soil type and slope, and a field may include a variety of zones (e.g., would provide further breakdown of a field to increase detail and accuracy of the system). In a still further example, a zone may be defined by any combination of any characteristics disclosed herein or other agronomic characteristics.

Hourly soil moisture may take into account moisture capacity of the soil, weighted average field capacity, dryout values of the soil, and other variables and characteristics. In one example, a weighted average of hourly soil moisture on all of the zones may be performed. In another example, an hourly soil moisture may be determined for each zone. In a further example, a weighted average of hourly soil moisture on all of the zones may be determined and then integrated with slope to distribute a virtual rain gauge value across all the zones. In still another example, an hourly soil moisture may be determined for each zone and then integrated with the slope of each zone to provide a virtual rain gauge for each zone. The virtual rain gauge may utilize weather data, e.g., hourly or daily, to determine how much rain has been received for a land area or point within a land area (e.g., a field, zones within a field, or numerous points within a zone). In one example, the weather data is an hourly binary spatial coverage file or stream from National Oceanic and Atmospheric Administration or Next-Generation Radar (NEXRAD).

Hourly soil moisture for a zone or zones may be determined in a variety of manners. In one example, hourly soil moisture may be determined as follows:

$$\text{Initial Soil Water Volume} + \text{Soil Moisture Change} = \text{End Soil Water Volume} \quad (1)$$

Initial soil water volume is the water volume of the soil at onset of the calculation or determination period. The initial soil water volume may be determined in a variety of manners. In one example, the initial soil water volume may be determined by an initial test of the soil using a moisture probe, sensor, or the like. In other examples, initial soil moisture may be assumed to be a certain value below saturation such as, for example, about 0.5 inches below saturation. In further examples, initial soil moisture may be downloaded from a database or received from a 3rd party. In still other examples, initial soil moisture may be calculated based on historical rainfall, irrigation, combination thereof, or other moisture data. Initial soil water volume may be represented with a variety of different units of measure or may be represented as a percentage.

Soil moisture change may be a positive value if rain, irrigation or some other manner of adding water to the soil occurs. Soil moisture change may be a negative value if water is not added to the soil. In one example, if water is added to soil and the moisture value is positive, the soil moisture change value may be equal to the amount of water added (e.g., in inches or some other unit of measure). For example, if it rains 0.5 inches, then the soil moisture change value would be 0.5 inches. In one example, if water is not added to the soil and the soil moisture change is negative, the soil moisture change may be referred to as a dryout value because the soil is drying out when water is not being added. For example, if water is not added to the soil, the dryout value may be −0.015626 inches. In instances where hourly soil moisture is desired, the unit of measure for the soil moisture change value would be per hour. Referring again to the above examples, if it rains 0.5 inches in one hour, the soil moisture change value would be 0.5 inches/hour, and if it doesn't rain in an hour, the soil moisture change value would be −0.015626 inches/hour.

In scenarios when the soil moisture change value is positive and water is being added to the soil, soil moisture change is relatively straight forward and may equal the amount of water added to the soil. Determination of soil moisture value when water is not being added and the soil moisture change value or dryout value is negative, determination of the dryout value may be determined in a wide variety of manners and may be dependent on a variety of different characteristics. In one example, the soil moisture change or soil dryout may be dependent upon the temperature. In this example, soil moisture change or soil dryout may be a first value/rate when the temperature is low, a second value/rate when the temperature is moderate, and a third value/rate when the temperature is high. Typically, the soil dryout value will be more negative (i.e., soil will dryout at a quicker rate) when the temperature is higher. In examples where temperature is utilized to determine dryout value, the dryout value may be different for any increment of temperature. For example, the dryout value may vary for every degree of temperature change, may vary on any increment of a degree of temperature change, a range of temperatures, or any other increment or range.

Once the end soil water volume is determined, end soil moisture may be determined. End soil moisture may be determined in a variety of manners. In one example, end soil moisture may be determined as follows:

$$\text{End soil moisture} = \text{End soil water volume} \div \text{Soil water holding capacity} \quad (2)$$

Soil water holding capacity may be determined based on a wide variety of different characteristics. In one example, soil water holding capacity may be determined based on one or more of soil type, slope, seed variety planted in soil, etc.

Generally, soil water holding capacity may represent the maximum amount of water that can be held by the soil. End soil moisture may also be represented as a percentage. In such a case the end soil moisture determined from formula (2) above would be multiplied by 100% to arrive at an end soil moisture percentage.

The system 20 may display an hourly soil moisture map for each zone or zones. Such a map may include an indicator associated with the end soil moisture. The indicator may take a variety of forms. For example, the indicator may be text, numbers, a percentage, a color coded scheme, or any other manner of representing and differentiating between various end soil moistures. In one example, a color coded scheme may include a plurality of different colored pins or indicators that have colors associated with different end soil moistures. The pins may be a first color if the end soil moisture is a first value or within a first range of values, a second color if the end soil moisture is a second value or within a second range of values, a third color if the end soil moisture is a third value or within a third range of values and so on. The color coded scheme may include any number of different colored indicators.

End soil moisture may be utilized to calculate or determine a wide variety of other agronomic characteristics including, but not limited to projected yield, solve for limiting factor, etc. The system 20 can also use hourly soil moisture in pre-season crop planning or making in-season adjustments. For example, the system 20 can use hourly soil moisture when solving for the ideal combination of pre-season crop planning data, e.g., the highest possible crop yield or highest possible crop yield with lowest plant population.

Figures 34, 35:
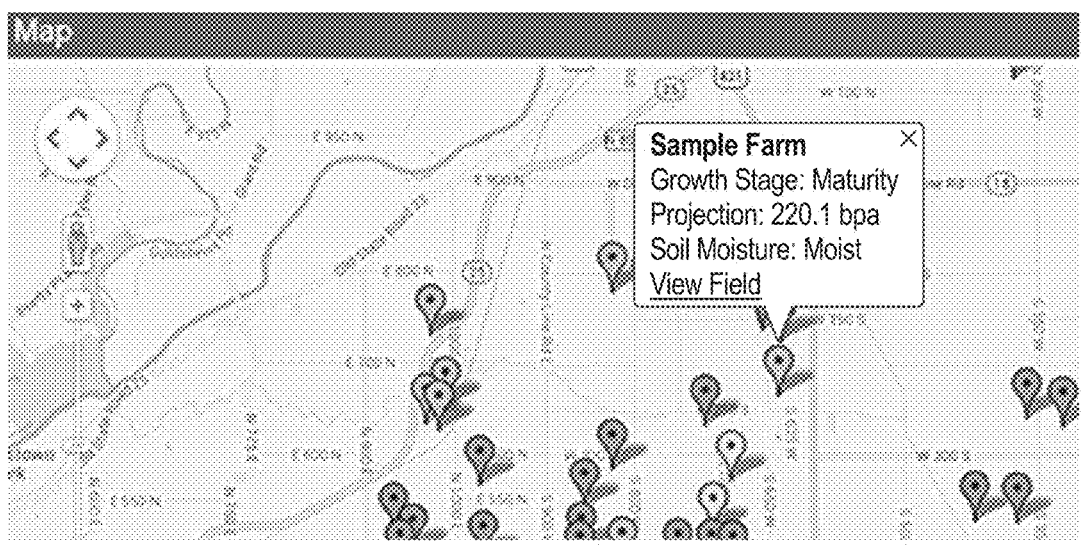
FIG. 34 is a chart illustrating one example of end soil moisture ranges or categories.
FIG. 35 is one example of a manner of demonstrating various end soil moistures across various zones, this example includes an exemplary map including one example of indicators for demonstrating end soil moistures in various zones.
Figure 37:
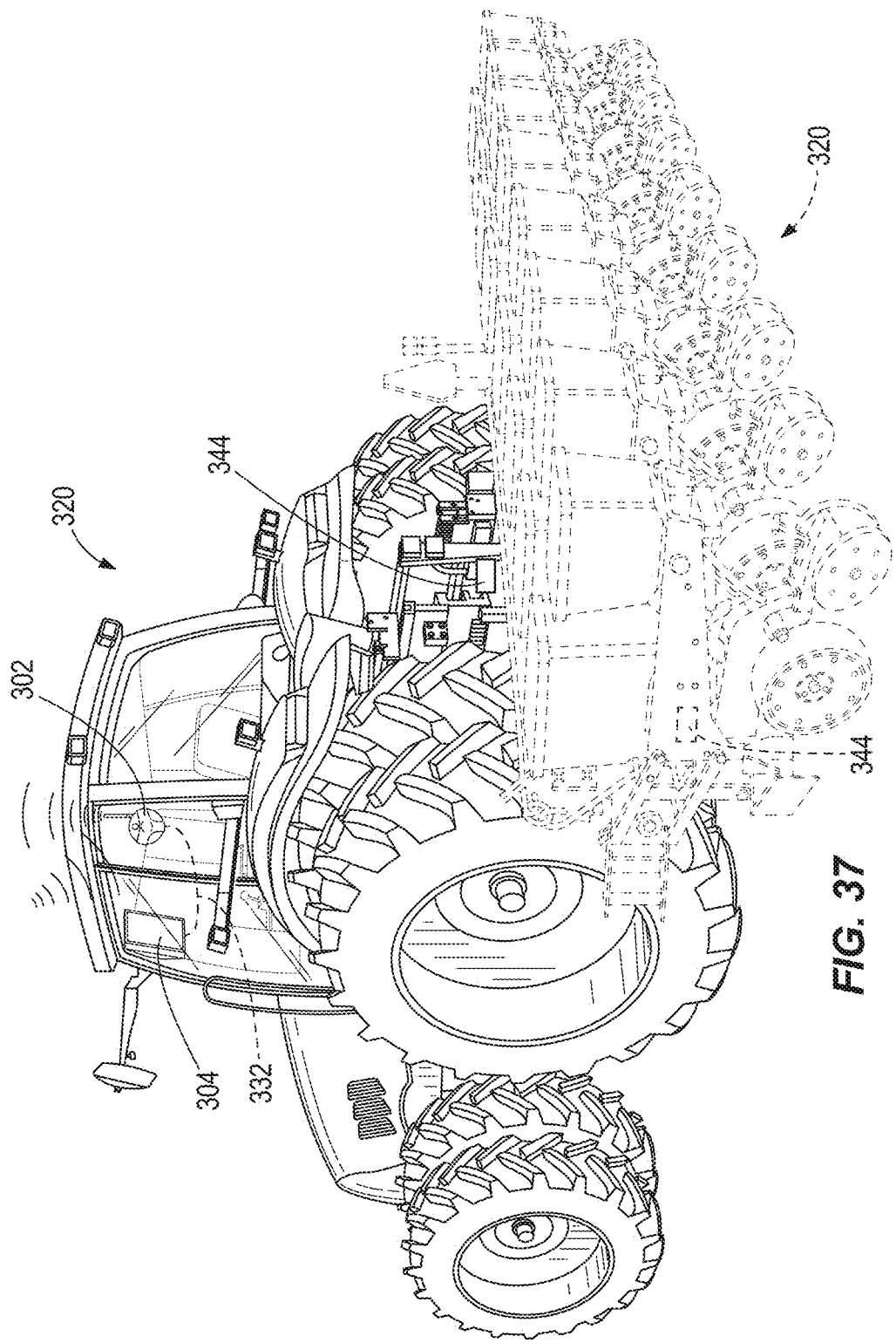
FIG. 37 is one example of at least a portion of an agricultural system of the present disclosure, the at least a portion of the agricultural system includes agricultural devices, such as, for example, a tractor and a planter, and also includes a first component and a second component.
Figure 38:
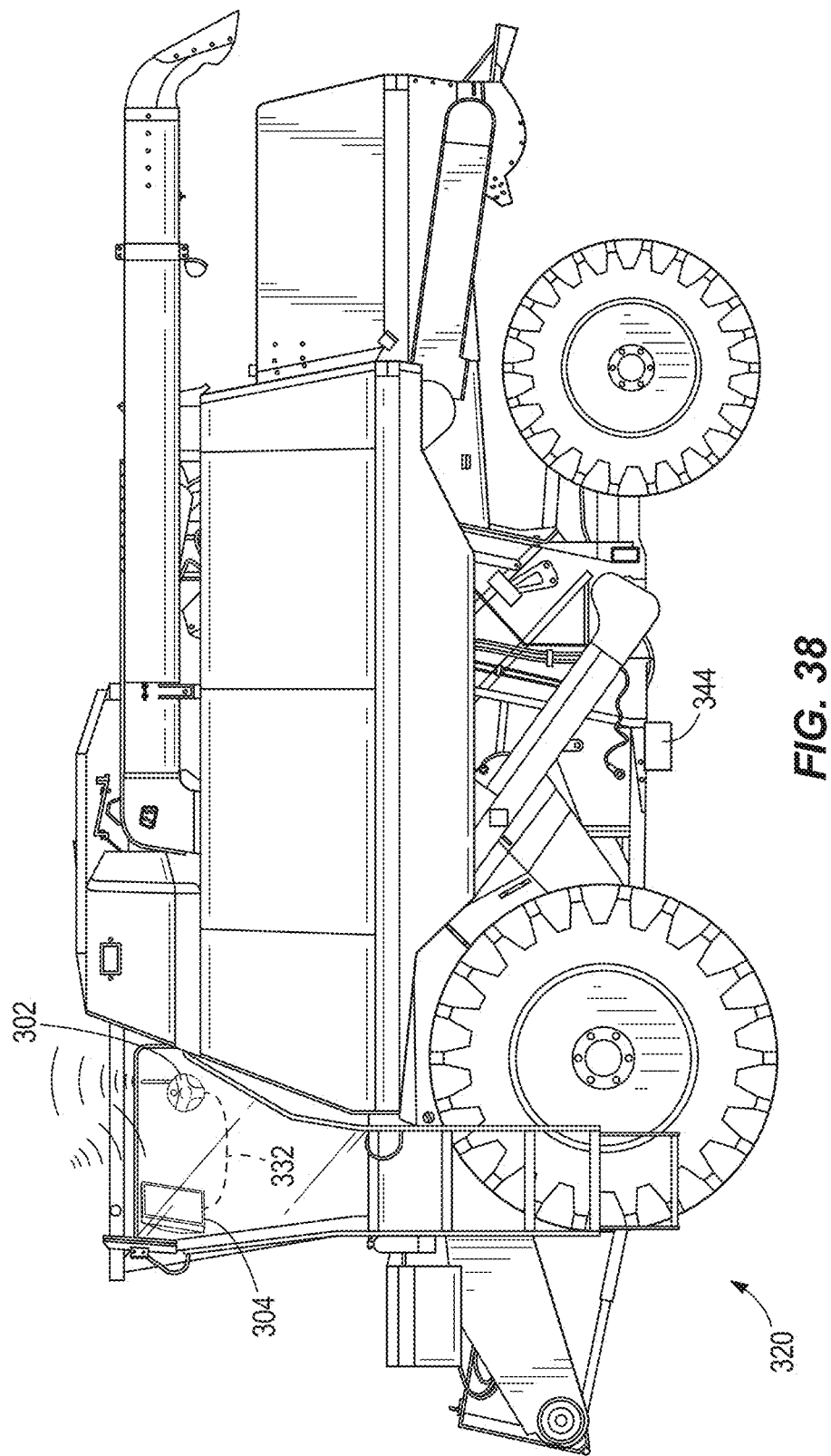
FIG. 38 is another example of at least a portion of an agricultural system of the present disclosure, the at least a portion of the agricultural system includes an agricultural device, such as, for example, a combine, and also includes a first component and a second component.
Figure 39:
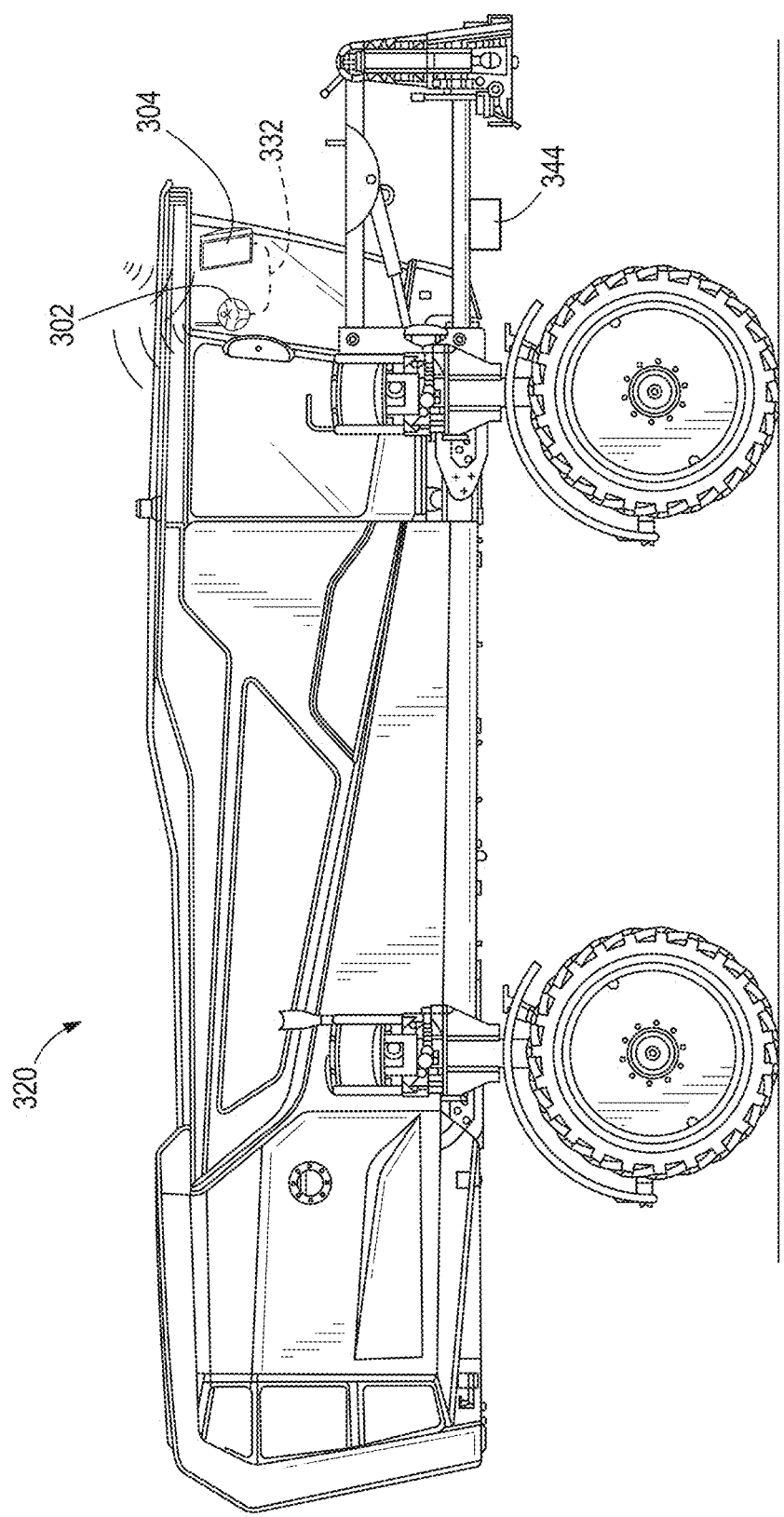
FIG. 39 is a further example of at least a portion of an agricultural system of the present disclosure, the at least a portion of the agricultural system includes an agricultural device, such as, for example, a sprayer, and also includes a first component and a second component.
Figure 40:
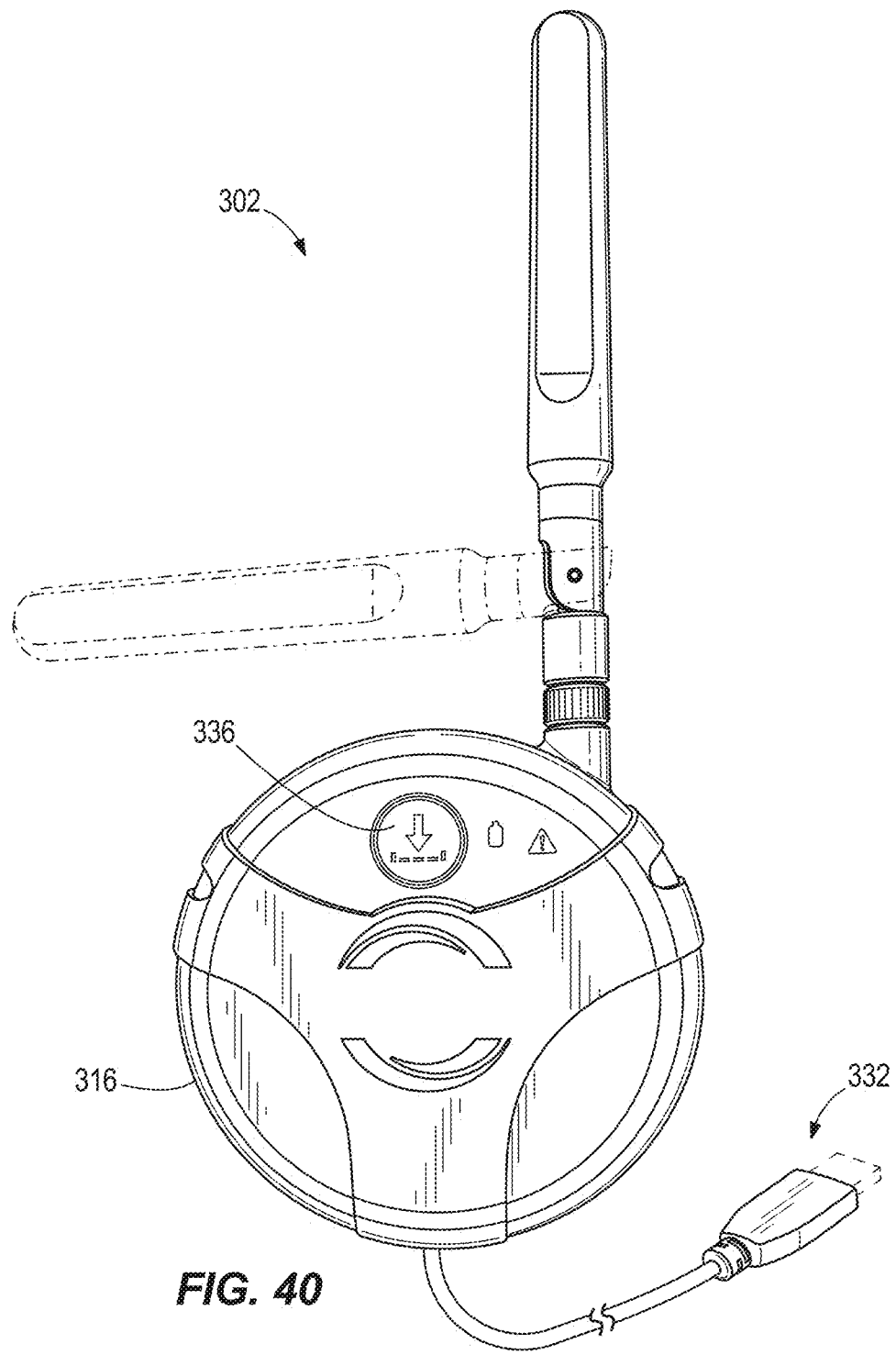
FIG. 40 is a front view of one example of a component of the agricultural system.

With reference to FIGS. 33-35, exemplary manners of the system 20 determining end soil moistures and visually demonstrating various end soil moistures to users are illustrated. These examples are not intended to be limiting upon the present disclosure. Rather, these examples are provided to demonstrate principles of the present disclosure and many other examples and manners are possible, all of which are intended to be within the spirit and scope of the present disclosure. Additionally, these examples include various values and assumptions. However, such values and assumptions are purely for exemplary purposes to demonstrate principles of the present disclosure, and should not limit the present disclosure. Other values and assumptions are certainly possible and are intended to be within the spirit and scope of the present disclosure.

Referring now to FIGS. 33A-33F, this chart illustrates one example of calculating soil moisture on an hourly basis over multiple days. In this example, the beginning soil moisture is 60%, the beginning soil water volume is 3.6, the temperature utilized for the calculations is 66° F., and the soil moisture capacity is 6 inches. Soil moisture capacity may be dependent on the type of soil. Many different types of soil exist (e.g., about 20,000 different types of soil) and, therefore, the soil moisture capacity may be a variety of different values. The soil moisture capacity represented in the figures is one example of many possible soil moisture capacity, is provided to demonstrate principles of the present disclosure, and is not intended to limit the present disclosure. Additionally, soil dryout rate is determined as follows:

If temperature<50° F., soil dryout rate=0.25 inches/day

If 50° F.<temperature<80° F., soil dryout rate=0.375 inches/day

If temperature>80° F., soil dryout rate=0.5 inches/day.

With continued reference to FIGS. 33A-33F, a first column represents the hour of the day since this example is an hourly soil moisture, a second column is a notes column, a third column is a daily rain (or irrigation) value comprised of a sum of the hourly rain over the day, a fourth column is a hourly rain value, a fifth column is a beginning soil moisture, a sixth column is a beginning soil water volume, a seventh column is a soil dryout value/rate, an eighth column is a crop uptake value (not used in this example), a ninth column is a soil moisture change, a tenth column is an end soil water volume, and an eleventh column is an end soil moisture.

In the chart, a first row represents 7:00 AM on Friday, May 31. During the 7:00 AM hour, it rained 0.1 inches, which results in a soil moisture change of 0.1. Formula (1) is utilized to calculate or determine the end soil water volume for the 7:00 AM hour on May 31. The beginning soil water volume is 3.6 inches and the soil moisture change of 0.1 inches is added to 3.6 to obtain an end soil water volume of 3.7. Formula (2) is utilized to calculate the end soil moisture for the 7:00 AM hour on May 31. The end soil water volume is 3.7 inches, which is divided by the soil water holding capacity of 6 inches to arrive at 0.6167. To change this calculation to a percentage, the end soil moisture is multiplied by 100% to arrive at 61.67%. The end soil moisture and the end soil water volume for the 7:00 AM hour on May 31 respectively become the beginning soil moisture and beginning soil water volume for the 8:00 AM hour on May 31. This repeats for each hour on the chart. For the 8:00 AM hour on May 31, it did not rain. Thus, the soil moisture change will be negative. Since the temperature is 66° F. in this example, the dryout rate is −0.375 inches/day, which is −0.015625 inches/hour (0.375/24=0.015625). Utilizing Formula (1) for the 8:00 AM hour on May 31, the end soil water volume is 3.684375 inches (3.7 inches−0.015625 inches). Utilizing Formula (2) for the 8:00 AM hour on May 31, the end soil moisture is 61.41% ((3.684375 inches÷6 inches)×100%). These two formulas can be used for every hour on the chart.

As indicated above, the end soil moisture may be divided into as many categories as desired and demonstrated to users in a variety of manners. With reference to FIG. 34, in this example the end soil moisture is separated into four categories and a color coding scheme is associated with the four categories to demonstrate variance in end soil moistures. The four exemplary categories include wet, moist, dry and stressed and each category includes a range of end soil moistures. The end soil moisture values in the associated column in the chart illustrated in FIGS. 33A-33F when compared to the exemplary category ranges illustrated in FIG. 34 determine the category for each hour of the day. The ends of the ranges defining the various categories may be any value to define any possible ranges. In the illustrated example, the value of 0.54 defining the beginning of the "stressed" range is an important value because a plant at this level of soil moisture does not have sufficient moisture to maintain crop yield potential, whereas at a soil moisture value of 0.55 a plant may be dry, but has sufficient soil moisture to maintain yield potential. Additionally, in the illustrated example, the value of 0.85 defining the beginning of the "wet" range is an important value because a field at this level of soil moisture is too wet to be navigated by equipment such as a harvester, sprayer, etc. Navigating a field that is too wet may damage the crop and/or equipment may get stuck in the saturated soil. Conversely, a field having a soil moisture of 0.84 may not be too wet and equipment may be able to navigate the field without damaging the crop or becoming stuck in the soil.

With reference to FIG. 35, one exemplary manner of demonstrating variance in soil moisture is illustrated. This example includes a map including a variety of zones and a color coded indicator for each zone. The color coded indicator is associated with the end soil moisture for that zone at that particular time. Since soil moisture is calculated on an hourly basis in the chart illustrated in FIGS. 33A-33F, the map illustrated in FIG. 35 may be updated on an hourly basis to reflect the soil moisture for that particular hour.

As indicated above, hourly soil moisture may be determined in a variety of manners utilizing a variety of variables and agronomic characteristics. For example, with reference to FIG. 36, hourly soil moisture may take into account temperature, rainfall, slope of the soil, moisture capacity of the soil, weighted average field capacity, dryout values of the soil, crop moisture uptake, and other variables and characteristics.

With specific reference to FIG. 36, another example of determining hourly soil moisture will be described. The first column is a time column. Since hourly soil moisture is being calculated, the time column includes time in hourly increments. The system 20 monitors time in the chosen time increment (hours in the illustrated examples). The system 20 may utilize other increments of time when calculating soil moisture at different time increments and, in such instances, the system 20 would include other increments in the time column. The next column is a notes column. The third column is a temperature column and the system 20 takes temperature readings at the time increments in the time column. The system 20 may include a thermometer that takes temperature readings at the associated time increments, and then populates the temperature column with the temperature. As indicated above in the example illustrated in FIGS. 33-35, temperature can impact the soil moisture change. Higher temperatures may dryout or decrease the soil moisture at a faster rate than lower temperatures. Dryout values may be determined based on any increment of temperatures. For example, ranges of temperatures may be used to determine a dryout rate, dryout rates may be determined on an individual degree basis, or the dryout rate may change at increments smaller than a single degree.

Figure 36:
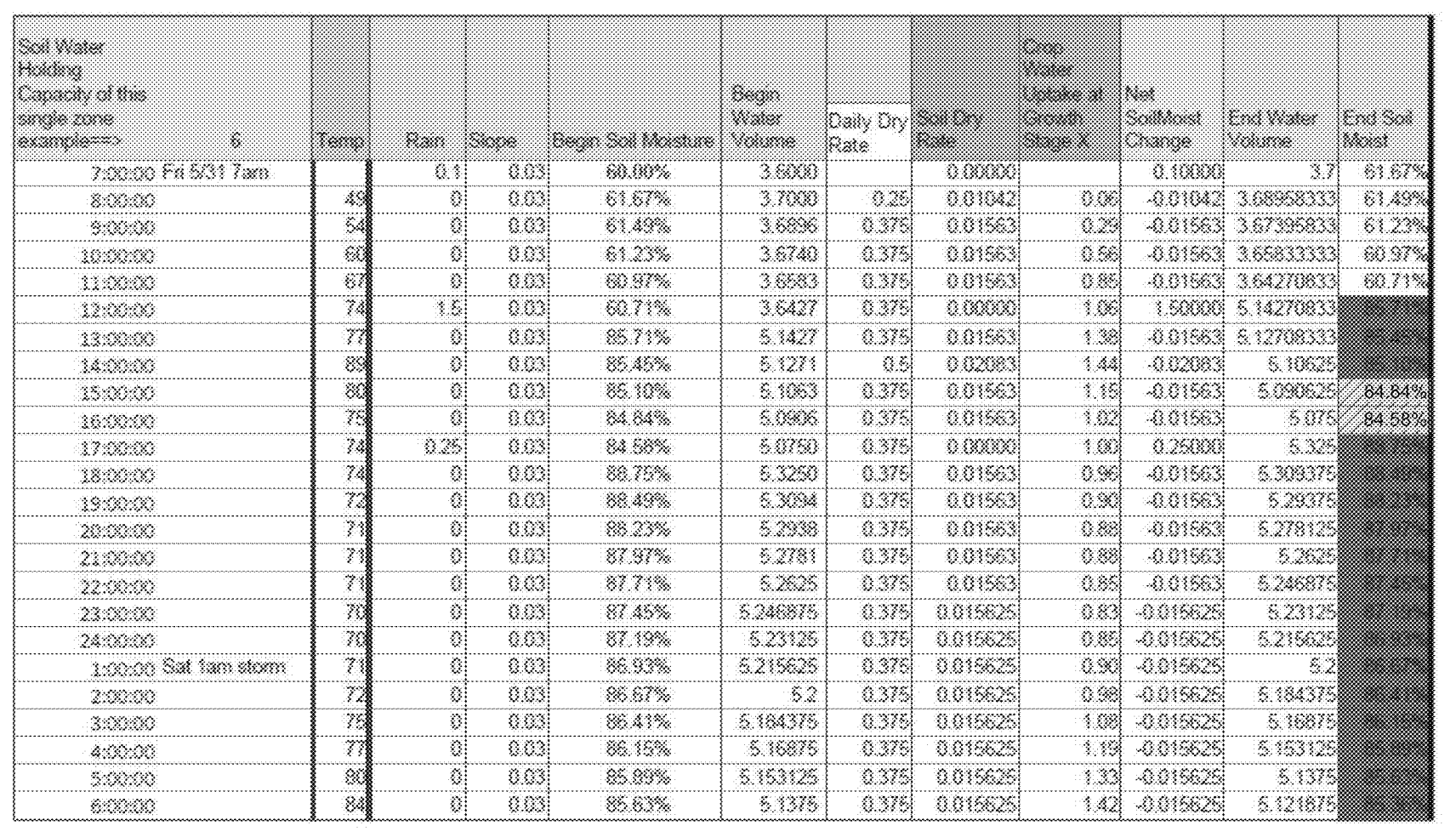

With respect to the fifth column of FIG. 36, the system 20 utilizes the slope of the soil, which may impact the soil moisture. For example, if the soil is relatively flat, then moisture is more likely to settle or remain on the flat soil. If the soil is steeply sloped then moisture will run-off or otherwise depart the steeply sloped soil. Additionally, if the soil is a valley or location that collects moisture, then the soil is likely to have a higher moisture. Further, if the soil is a peak or hill top, then soil is likely to run-off or otherwise depart the peak or hill top location. The slope value may vary depending on the slope of the soil and, therefore, the impact of the slope on the soil moisture may change as the slope varies. In the illustrated example, the slope value is the same for all time increments. However, in other examples, the slope value may vary.

The system 20 introduces beginning soil moisture in the next column and is represented as a percentage. In the next column, the system 20 represents the beginning soil moisture or water volume in inches. In the next column, the system 20 includes a daily dry rate, which the system 20 bases on the temperature included in the temperature column. The second row, which represents the 8:00 AM hour on May 31, has a temperature of 49 degrees. The daily dry rate associated with a temperature of 49 degrees is 0.25. The third row, which represents the 9:00 AM hour on May 31, has a temperature of 54 degrees. The daily dry rate associated with a temperature of 54 degrees is 0.375. The eighth row, which represents the 2:00 PM hour on May 31, has a temperature of 89 degrees. The daily dry rate associated with a temperature of 89 degrees is 0.5. It should be understood that the daily dry rates may be any value and the illustrated examples are provided to demonstrate principles of the present disclosure. To arrive at the hourly rate, which is represented in the column to the right of the daily dry rate, the system 20 divides the daily dry rate by 24 (24 hours in a day).

The type of crop and the growth stage of the crop also affect the soil moisture. The system 20 represents crop moisture uptake in the next column and may have various values based on the crop type and growth stage of the crop. The illustrated values associated with the crop uptake may be a variety of different values, are provided to demonstrate principles of the present disclosure and should not be limiting upon the present disclosure.

The system 20 represents the net soil moisture in the next column and is the summation of all variables that affect the change in soil moisture. The net soil moisture may be represented by inches. For example, the net soil moisture may be equal to the impacts of crop uptake, crop dryout, slope and other possible variables and/or agronomic characteristics. The system 20 calculates the net soil moisture by subtracting from or adding to (depending on the final value) the beginning water volume to arrive at the end water volume. Similarly to the example illustrated in FIGS. 33-35, the system 20 executes Formula (2) to arrive at the end soil moisture and converted to a percentage by multiplying by 100%. The system 20 represents the end soil moisture as a percentage in the last column in FIG. 36. The system 20 may represent the end soil moisture to a user in any of the manners described above, alternatives thereof, or equivalents thereof.

The above examples illustrated in FIGS. 33-36 illustrate and describe rainfall as the water source affecting soil moisture. However, it should be understood that irrigation, tile systems, and/or any other water related systems may also affect soil moisture and may be considered in lieu of or in combination with rainfall when determining soil moistures.

It should be understood that the customization disclosed herein may be performed by a user, by a $3^{rd}$ party data source, by the system 20 itself, or any combination thereof.

The system 20 and computing element 32 determine projections based on a variety of data or information. Such data and information may be a wide variety of data, such as the various types of data and information described herein, or other types of data. The system 20 and computing element 32 may determine such projections based on quantity of data, combination of data and any permutation of data. The following examples of the system 20 and the computing element 32 determining projections are only examples of the many possible projections and manners of projecting that the system 20 and the computing element 32 are capable of performing. The system 20 and computing element 32 are also capable of providing the projections in a variety of manners. The following examples of the system 20 and the computing element 32 providing projections are only examples of the many possible manners of providing projections. These examples are not intended to be limiting upon the present disclosure, but rather are provided to demonstrate at least some of the principles of the present disclosure.

As indicated above, the system 20 and the computing element 32 are capable of performing pre-season projections and in-season projections. Examples of types of projections include, but are not limited to, limiting growth factor, crop yield, moisture content of a crop, etc.

Figure 15:
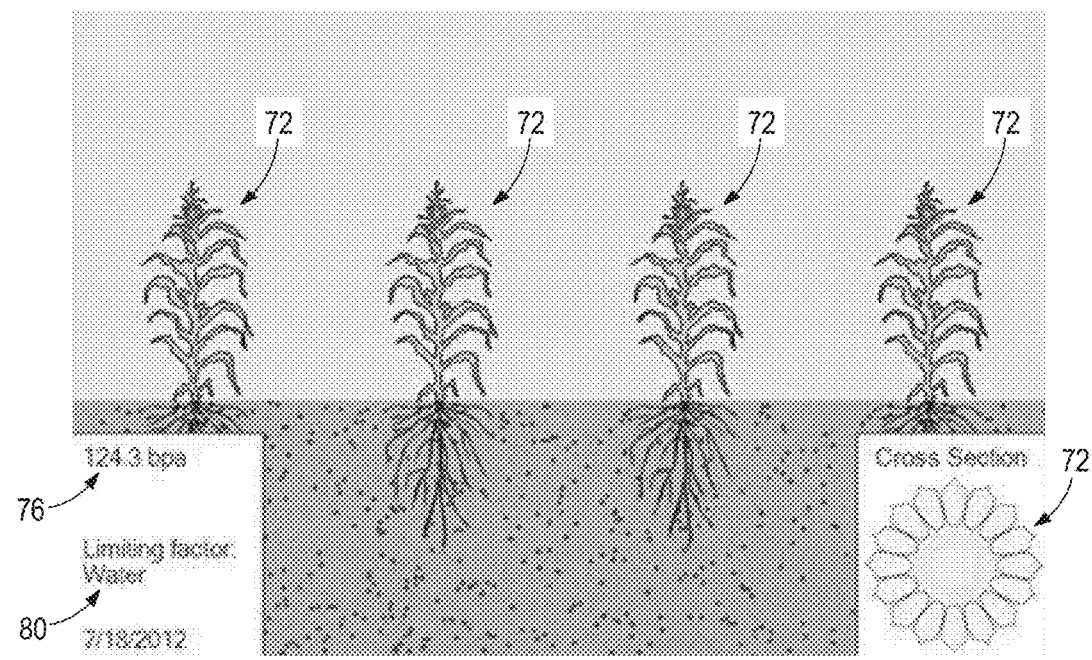
FIG. 15 is one example of a visual format of data communicated by one or more of the systems, in this example the visual format is an image of at least one exemplary plant in a crop illustrating a growth state, projected yield of the crop, and a cross-sectional representation of an ear of corn at a particular date.
Figure 16:
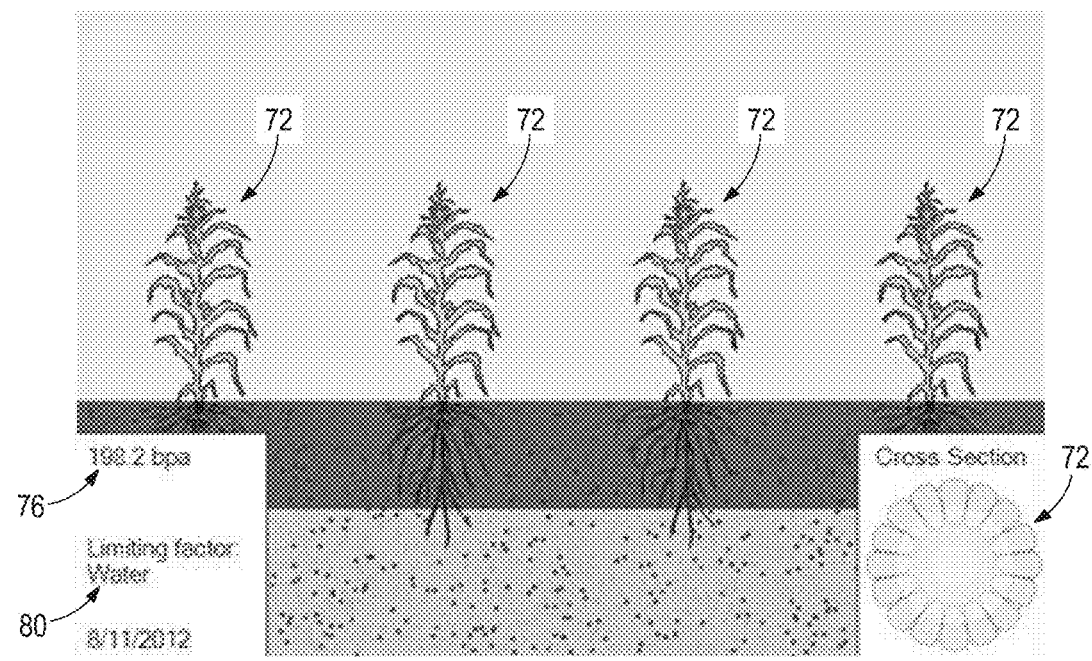
FIG. 16 is one example of a visual format of data communicated by one or more of the systems, in this example the visual format is an image of at least one exemplary plant in a crop illustrating a growth state, projected yield of a crop, and a cross-sectional representation of an ear of corn at a particular date.

The system 20 and the computing element 32 may provide the projections and other data in a variety of manners. The system 20 and the computing element 32 may communicate the projections and data over one or more networks 44 to one or more devices. In one example, the system 20 and computing element 32 may communicate the projections and/or other data over one or more networks 44 to a device where a user may view the data (see FIG. 3) and/or hear the data. Examples of devices include, but are not limited to, personal computers, mobile electronic communication devices, etc. The system 20 and computing element 32 may communicate projections and/or other data to the devices in a variety of manners including, but not limited to, email, text, automated telephone call, telephone call from a person, a link to a website, etc. In such examples, the system 20 and computing element 32 may display or audibly produce the projections and/or other data in a variety of manners. For example, the projections and/or communicated data may be in a text format comprised purely of letters, words, and/or sentences. Also, for example, the projections and/or other data may be in a visual or illustrative format. The visual or illustrative format may take on many forms and display a wide variety of types of information. In one example, the visual format may display projections of crop growth at various stages of growth (see FIGS. 15 and 16). In such examples, a plant or plants 72 included in the crop may be shown at the selected growth stage. In the illustrated example, corn 72 is the illustrated crop. In FIG. 15, the corn is illustrated in the form it will likely take on Jul. 18, 2012. Note that the cross-section of the corn on Jul. 18, 2012 is underdeveloped. Then, in FIG. 16, the corn is illustrated again in the form it will likely take on Aug. 11, 2012. In FIG. 16, the cross-section of the corn shows that the corn is much more developed on Aug. 11, 2012. Also note that the projected crop yield 76 is also much higher on Aug. 11, 2012 than it was earlier on Jul. 18, 2012.

It should be understood that corn is shown only as an example and the system 20 may display any type of crop and any such possibility is intended to be within the spirit and scope of the present disclosure. For example, other possibilities for crops include, but are not limited to, soybeans, potatoes, wheat, barley, sorghum, etc.

Figure 17:
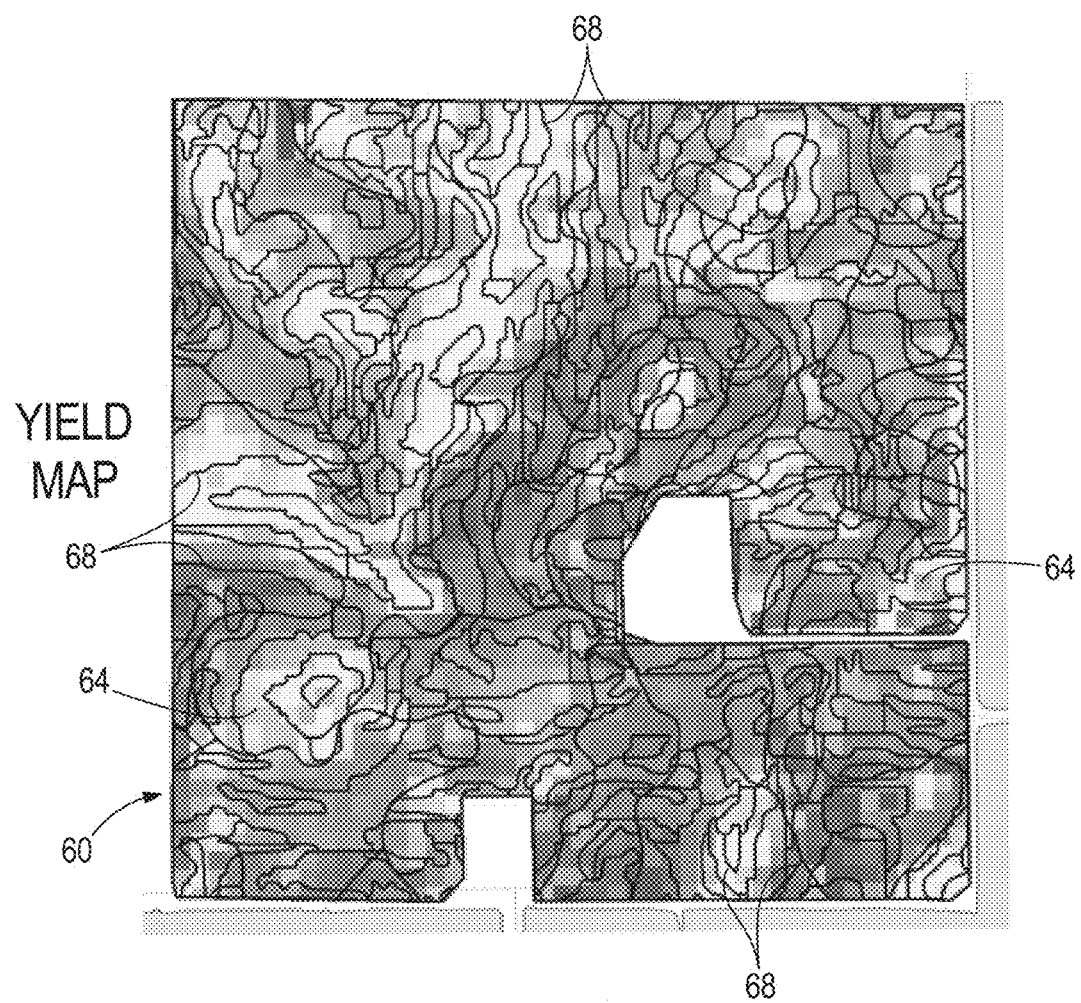
FIG. 17 is one example of a visual format of data communicated by one or more of the systems, in this example the visual format is a map including contour lines for illustrating different slopes and a plurality of zones color coded based on projected crop yield of the land area of interest.

Further, for example, the system 20 and computing element 32 may communicate the projections and/or other data in a combination of text and visual formats. For example, with reference to FIGS. 15 and 16, both text and visual formats are shown. Examples of the text and illustrations shown include, but are not limited to, the date at which the projection is desired, multiple appearances of the plant(s) at the projection date (e.g., profile and cross-section), crop yield of the selected land area of interest and a limiting factor 80. Additionally, for example, the system 20 and computing element 32 may communicate the projections with visual formats only. For example, with reference to FIG. 17, estimated or projected crop yield are determined by the system 20 and the computing element 32, and the system 20 and computing element 32 illustrate the crop yield in a map format. The varying greyscale colors represent different crop yields over a land area of interest. In one example, darker colors may represent higher crop yields and lighter or white colors may represent lower crop yields.

In one example, a user may view projections and/or other data at a land area of interest level, which may be comprised of a single zone, a single field including a plurality of zones, a group of fields associated with one another, or any other land area size.

In one example, a user may select via the system 20 a group including a plurality of fields. The system 20 and the computing element 32 will provide (in any of the manners described above or alternatives thereof, all of which are intended to be within the sprit and scope of the present disclosure) the projections and/or other data associated with group. If a group is selected, the projection may include a weighted average sum of the crop yield for all of the crops included in this group of fields. This projection provided at this level by the system 20 may be beneficial to a user who manages a large quantity of fields and desires to know their overall crop yield. As data inputted into the system 20 and the computing element 32 changes (e.g., weather, inputs, etc.), the crop yield may change. The system 20 and the computing element 32 may communicate this change to one or more devices over one or more networks 44. This communication may also be referred to as an alert. The amount of change necessary to initiate an alert may be any size. In one example, the amount of change may be a unit of measure associated with crop yield such as, for example, bushels per acre (bpa).

In another example, the data communicated by the system 20 and computing element 32 with respect to the group of fields may be a limiting factor, which is a factor or characteristic that limits the crop yield. A wide variety of factors may limit the crop yield and at least some of the limiting factors are described above. The communicated limiting factor may be the limiting factor for the entire group. Providing the limiting factor via the system 20 at the group level may be beneficial to a user who manages a large quantity of fields and desires to know the limiting factor that is having the largest impact on their entire group of fields. As data inputted into the system 20 and the computing element 32 changes (e.g., weather, inputs, etc.), the limiting factor may change. The system 20 and the computing element 32 may communicate this change to one or more devices over one or more networks 44. This communication may also be referred to as an alert. An alert may be communicated anytime the limiting factor changes. The user may then take appropriate action to account for the limiting factor.

In one example, a user may select a field including a plurality of zones. The system 20 and the computing element 32 will provide (in any of the manners described above or alternatives thereof, all of which are intended to be within the spirit and scope of the present disclosure) the projections and/or other data associated with field and its zones. If a field is selected, the projection may include a crop yield for the single field and its zones. This projection provided at this level by the system 20 and the computing element 32 may be beneficial to a user who only has a single field or wants to drill down to a more detailed level where individual fields can be analyzed. As data inputted into the system 20 and the computing element 32 change (e.g., weather, inputs, etc.), the crop yield may change. The system 20 and the computing element 32 may communicate this change to one or more devices over one or more networks 44. This communication may also be referred to as an alert. The amount of change necessary to initiate an alert may be any size. In one example, the amount of change may be a unit of measure associated with crop yield such as, for example, bushels per acre (bpa).

In another example, the data communicated by the system 20 and the computing element 32 with respect to the single field and its zones may be a limiting factor, which is a factor or characteristic that limits the crop yield of the field. A wide variety of factors may limit the crop yield and at least some of the limiting factors are described above. The limiting factor communicated by the system 20 and the computing element 32 may be the limiting factor for the entire field. Providing the limiting factor with the system 20 and computing element 32 at the field level may be beneficial to a user who has only a single field or has a field with many zones and wishes to understand the limiting factor of the entire field. As data inputted into the system 20 and the computing element 32 changes (e.g., weather, inputs, etc.), the limiting factor may change. The system 20 and the computing element 32 may communicate this change to one or more devices over one or more networks 44. This communication may also be referred to as an alert. An alert may be communicated anytime the limiting factor changes. The user may then take appropriate action to account for the limiting factor.

In one example, a user may select, via the system 20, a particular zone of a field or fields comprised of a plurality of zones. The system 20 and the computing element 32 will provide (in any of the manners described above or alternatives thereof, all of which are intended to be within the spirit and scope of the present disclosure) the projections and/or other data associated with the single zone. If a zone is selected, the projection may include a crop yield for the single zone within the field. This projection provided at this level may be beneficial to a user that desires to know how each zone is performing. As data inputted into the system 20 and the computing element 32 changes (e.g., weather, inputs, etc.), the crop yield for a zone may change. The system 20 and the computing element 32 may communicate this change to one or more devices over one or more networks 44. This communication may also be referred to as an alert. The amount of change necessary to initiate an alert may be any size. In one example, the amount of change may be a unit of measure associated with crop yield such as, for example, bushels per acre (bpa).

In another example, the data communicated by the system 20 and computing element 32 with respect to a zone within one or more fields may be a limiting factor, which is a factor or characteristic that limits the crop yield. A wide variety of factors may limit the crop yield and at least some of the limiting factors are described above. The communicated limiting factor may be the limiting factor for just that zone. Other zones in the field or fields may have other limiting factors. Providing the limiting factor, via the system 20 and computing element 32, at the zone level may be beneficial because it provides the ability to drill down to a very specific level and allow understanding and crop planning for the specific zone. Rather than treat an entire field the same way, each zone within a field may be treated differently (e.g., irrigation, input, nutrients, etc.) to optimize crop yield in each zone, thereby optimizing crop yield over the entire land area of interest. As data inputted into the system 20 and the computing element 32 changes (e.g., weather, inputs, etc.), the limiting factor may change. The system 20 and the computing element 32 may communicate this change to one or more devices over one or more networks 44. This communication may also be referred to as an alert. An alert may be communicated anytime the limiting factor changes. The user may then take appropriate action to account for the limiting factor.

In one example, a plurality of projections and/or other data may be provided by the system 20 and computing element 32 for a plurality of zones or a plurality of fields. The system 20 and computing element 32 may provide such projections and/or other data in a list or multiple visual elements. This provides the ability to easily identify those zones or fields that may be underperforming or at least performing at a lower level than other zones or fields. A user may then address, via the system 20 and computing element 32, the underperforming zone(s)/field(s), determine a cause for low or lower performance, and determine a remedy.

In one example, the system 20 and the computing element 32 may communicate the projections and/or other data to one or more agricultural devices to assist with controlling the one or more agricultural devices in accordance with the communicated data.

As indicated above, the projections and/or other data may be used to plan or take appropriate action to improve the agronomics of a land area of interest. In one example, the projections and/or other data may be used to determine the best seed variety of a given land area of interest. A user may evaluate seed varieties, typically recommended by a user's agronomist or seed salesman, and a date of planting and the system 20 and the computing element 32 will analyze this inputted information along with other inputted information and determine a maximum crop yield and lowest input rate for each zone within the land area of interest. Once a desired result has been achieved, the result may be used for crop planning. In one example, a user takes action in accordance with the desired result. In another example, data associated with the desired result may be downloaded and communicated, via the system 20 and computing element 32, to one or more agricultural devices where the one or more agricultural devices may operate in accordance with the data. This feature may be valuable for crop planning purposes and provides users to tryout different seed varieties on different zone properties (e.g., soil, etc.) given a user's tolerance to risk and diversity. Growth conditions may change in-season and running many pre-season scenarios with the system 20 can prepare users for any potential changes.

In one example, the system 20 and computing element 32 may use the projections and/or other data to determine when nitrogen should be applied and how much nitrogen to apply. Crops have various growth stages and require different attention at the various growth stages. The system 20 and the computing element 32 may be used to determine at what growth stage to apply nitrogen and how much nitrogen to apply. A user may select, via the system 20, a growth stage associated with the seed variety planted and/or select, via the system 20, a date at which the user intends to apply nitrogen. The system 20 analyzes this information along with other inputted data such as, for example, soil data, seed data, weather data, etc. Growth characteristics change as the growth season progresses (e.g., soil condition, water levels, weather, etc.), which impacts the amount of nitrogen required by the crop. Examples of growth conditions that can affect nitrogen demand include, but are not limited to, large rain events, favorable soil mineralization, etc. This feature of the system 20 provides users with the ability to tryout different growth conditions and determine how these variances in growth conditions affect the crop's nitrogen demand so that the user will be ready to foresee and/or resolve nitrogen deficiencies before they occur or immediately after they occur during the growing season. In this example, the system 20 and the computing element 32 may communicate an alert to a user and/or an agricultural device (in any of the manners described herein) indicating that a nitrogen deficiency is about to occur or has just occurred. The user and/or the agricultural device can then take appropriate action to resolve the nitrogen deficiency.

In one example, the system 20 and computing element 32 may use the projections and/or other data to determine moisture content of a crop. In the past, farmers guessed the moisture content of the crop and determined a harvest date based on that guess. Also, in the past, farmers may have used a handheld moisture tester. In one example, the system 20 and the computing element 32 allow a user to determine the moisture content of the crop without guessing and without performing tests in the actual field or land area of interest. The system 20 and the computing element 32 receive and analyze various inputted data and determine the moisture content of the crop based on the inputted data. In one example, the inputted data relied upon by the system 20 and the computing element 32 to determine moisture content of the crop includes, but is not limited to, weather data, planting date and seed profile of the seed variety planted in the land area of interest. By having the system 20 and the computing element 32 calculate the moisture content of the crop, the user saves time and money by not having to perform tests in the field. An accurate moisture content informs the user about when the crop should be harvested. Certain crops require certain levels of moisture before they are ready for use, storage, sale, etc. If a user harvests a crop prior to the crop reaching the desired moisture content, the user must dry the crop the remaining amount. This drying process can be expensive and lengthy. Thus, the system 20 and the computing element 32 provide the necessary information with respect to crop moisture content to allow the user to make an educated decision of when to harvest a crop and how much drying will be required. It's up to the user to then perform a cost benefit analysis of harvesting versus letting the crop stand longer for additional drying.

Figure 18:
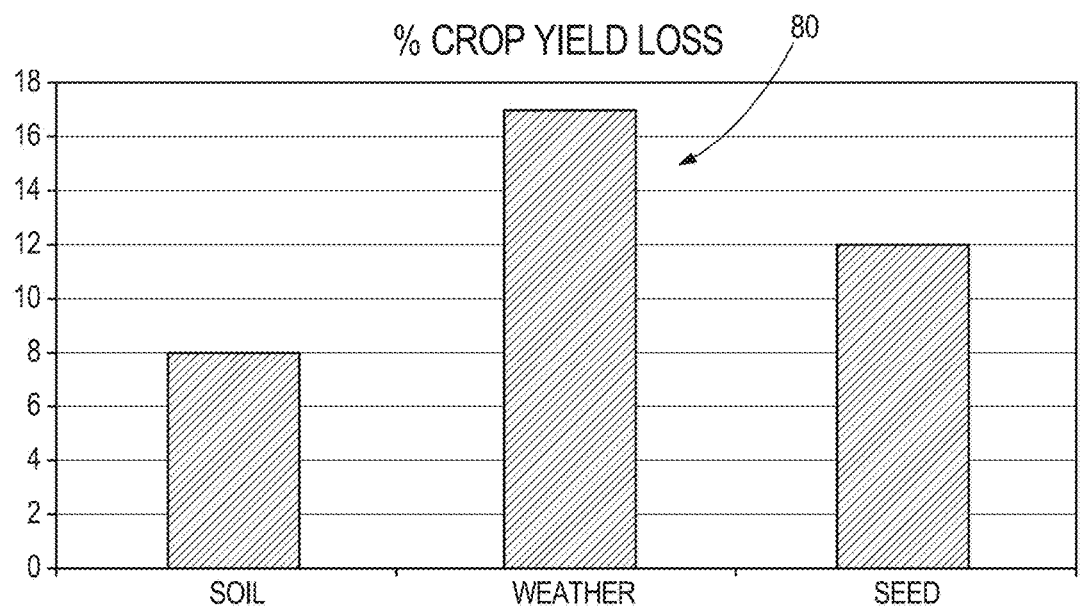
FIG. 18 is one example of a visual format of data communicated by one or more of the systems, in this example the visual format is a bar graph for illustrating percentage yield losses as they relate to three agronomic factors, in this example the agronomic factors are soil, seed and weather and the agronomic factor that has a highest percentage yield loss (weather in this example) is a limiting factor.
Figure 19:
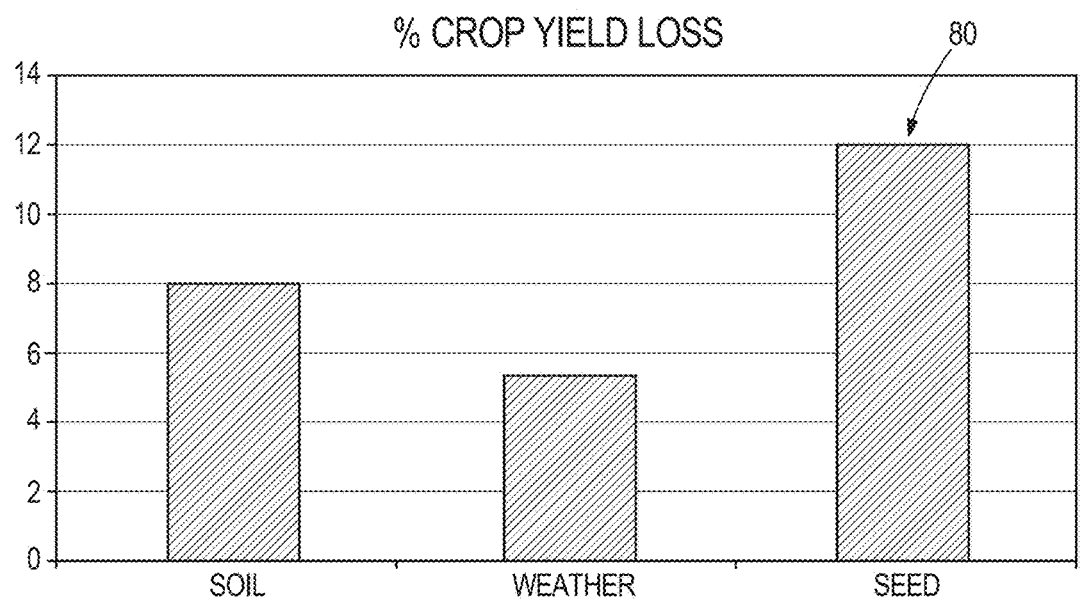
FIG. 19 is one example of a visual format of data communicated by one or more of the systems, in this example the visual format is a bar graph for illustrating percentage yield losses as they relate to three agronomic factors, in this example the agronomic factors are soil, seed and weather and the agronomic factor that has a highest percentage yield loss (seed in this example) is a limiting factor.
Figure 26:
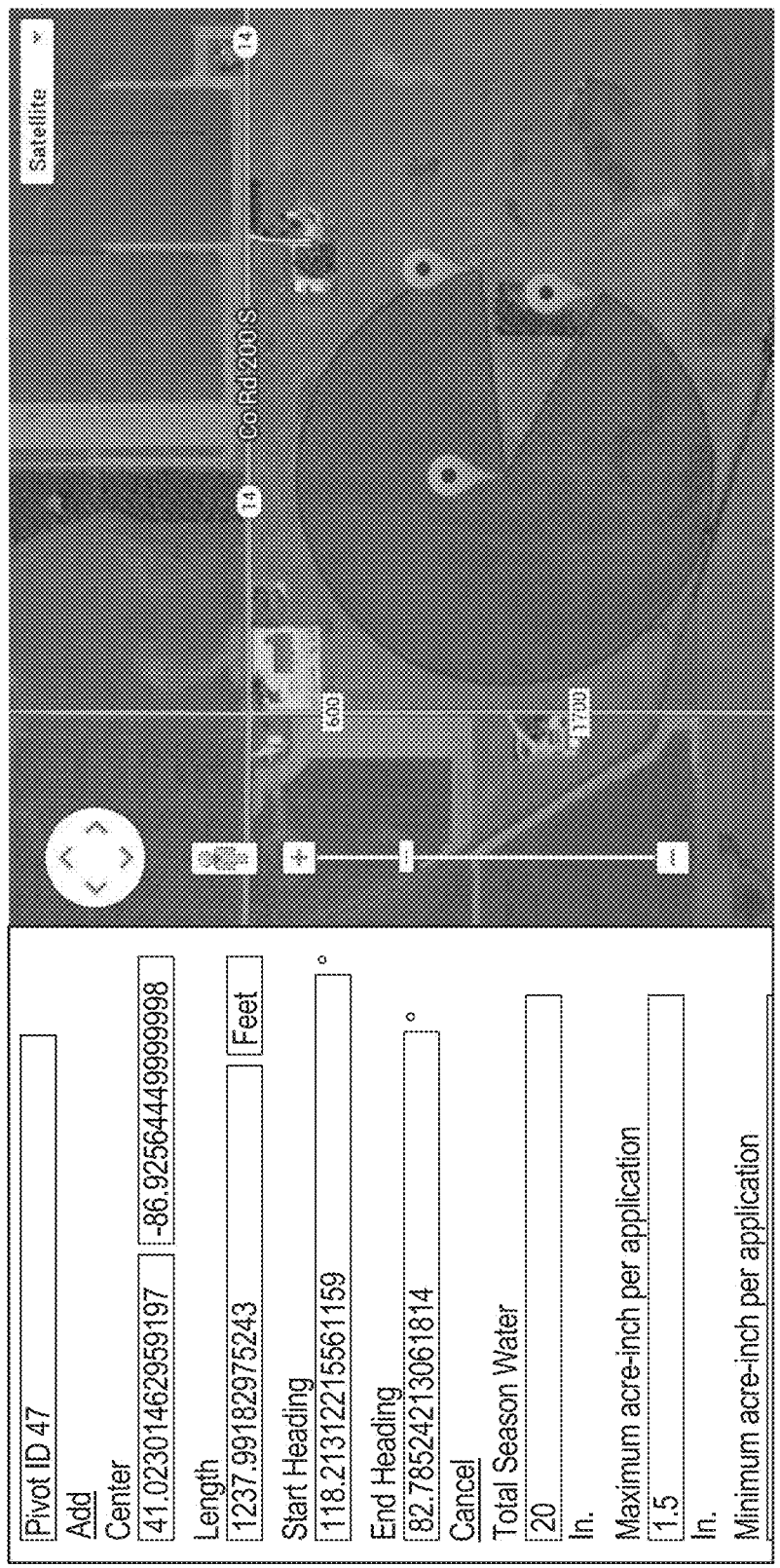
Figure 29:
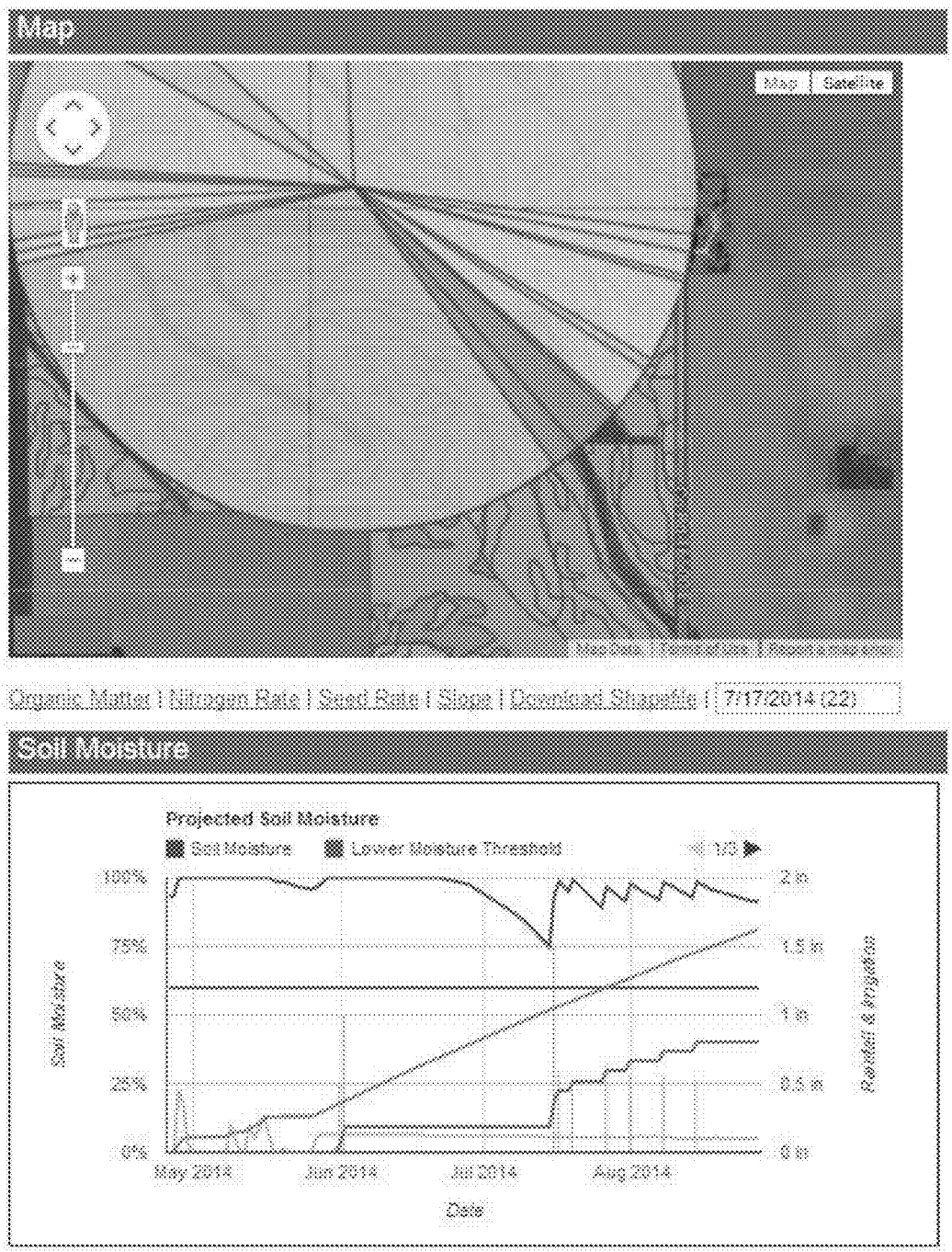
Figure 30:
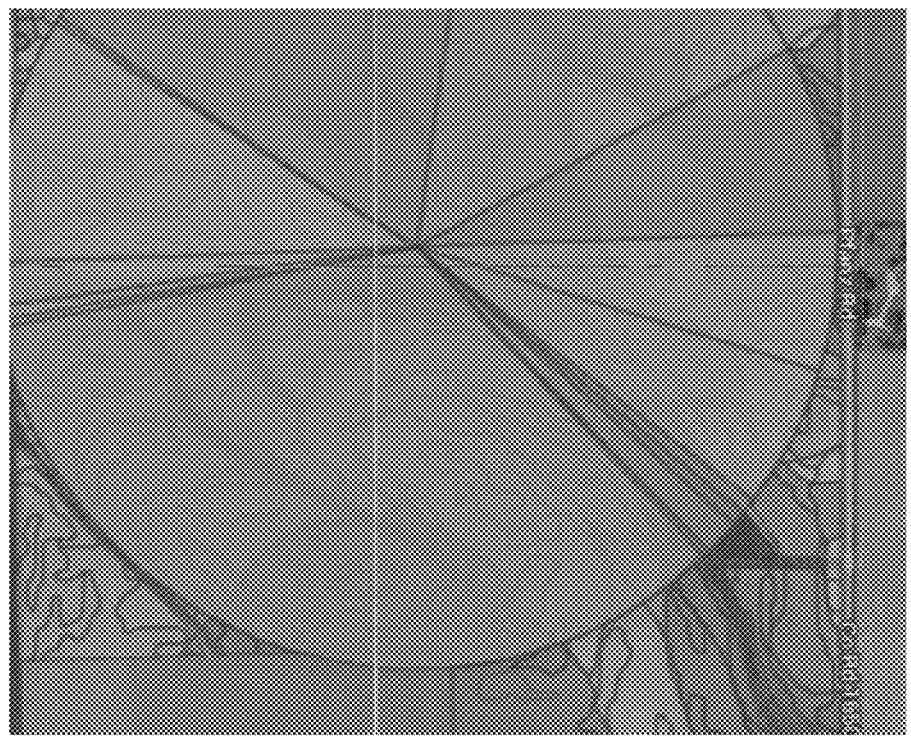
Figure 31:
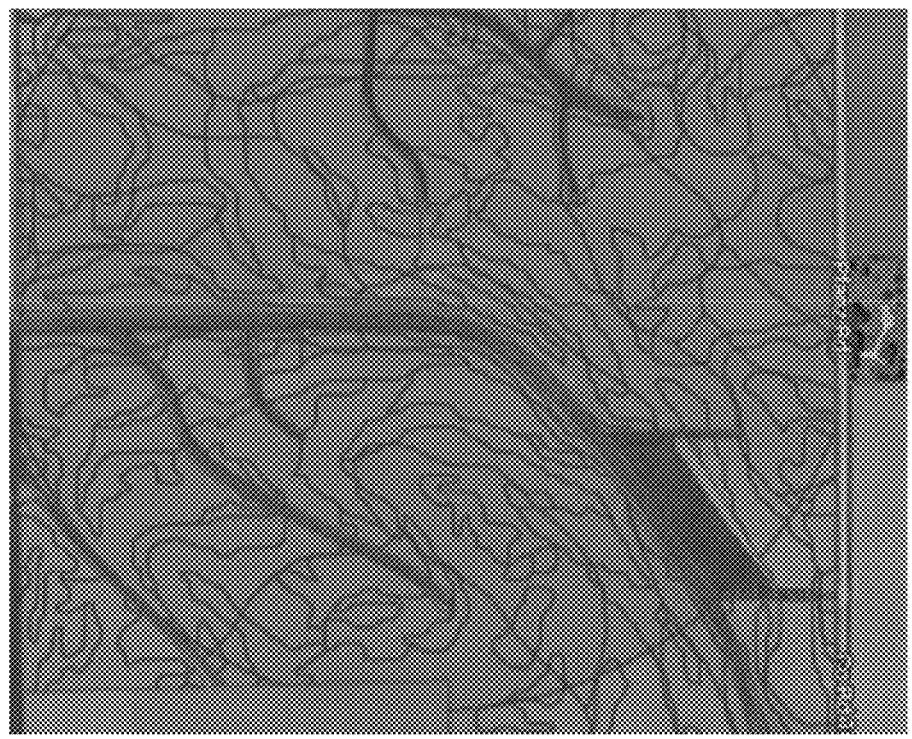
Figure 32:

Referring now to FIGS. 18 and 19, one example of the system 20 and the computing element 32 determining a limiting factor 80 is illustrated and described. This example is provided to demonstrate principles of the present disclosure and is not intended to be limiting upon the present disclosure. Rather, the system 20 and the computing element 32 are capable of determining a limiting factor in a variety of other manners and all such manners are intended to be within the spirit and scope of the present disclosure.

In this example, the system 20 and the computing element 32 initially determine a percentage crop yield loss and then use the yield loss to determine the limiting factor. However, it is not necessary for the system 20 and computing element 32 to utilize only percentage crop yield loss in determining the limiting factor for in-season adjustments or pre-season crop planting. For example, the system 20 and computing element 32 may consider changes in yield loss/day, bushels per acre, bushels per seed, bushels per thousand seeds, bushels per inch of rain, bushels per pound of nitrogen, or frost risk in determining the limiting factor. In this sense, the limiting factor is the agronomic factor that impacts the yield loss the most or has the largest yield loss relative to other agronomic factors. While the system 20 and the computing element 32 can determine a percentage crop yield loss for any number of agronomic factors, this example considers three agronomic factors. The three agronomic factors are soil, seed and weather. Thus, the system 20 and the computing element 32 determine which one of these three agronomic factors results in the largest yield loss. The one of soil, seed and weather that results in the largest yield loss is determined to be the limiting factor.

Each of the three agronomic factors has subcategories or sub-factors that impact the system's and the computing element's calculation of the yield loss. For example, with respect to the soil agronomic factor, the system 20 and the computing element 32 receive and analyze data associated with nitrogen rates, water holding capacity, soil type, soil pH, organic matter in the soil, CEC, percent of field capacity, mineralization, etc. Nitrogen rates may be calculated by evaluating soil pH, organic matter, and CEC. CEC and pH may affect availability of nitrogen. The system 20 and the computing element 32 may retrieve organic matter data from a $3^{rd}$ party source, from a soil test performed by a soil testing device, or a combination of the two. Field capacity is important in establishing the ideal nitrogen rate. A field may be completely saturated (i.e., 100 percent field capacity) or dry (e.g., about 50 percent field capacity). When the field is dry or has a low percent field capacity, no or very little mineralization is occurring. Mineralization is generally a conversion of organic nitrogen to ammonia. Between the saturated and dry boundaries, nitrogen will be mineralized at different rates. For example, more nitrogen will mineralize on hotter days compared to less mineralization on cooler days. Also, for example with respect to the seed agronomic factor, the system 20 and the computing element 32 receive and analyze data associated with seed rate and seed variety (includes seed profile data). The system 20 and the computing element 32 can extrapolate projected yields for different varieties of seeds having different relative maturity dates. Further, for example with respect to the weather agronomic factor, the system 20 and the computing element 32 receive and analyze data associated with actual weather, historical weather, irrigation, growing degree days (GDD).

The system 20 and the computing element 32 receive and analyze all the sub-categories of the three main agronomic factors and determine the percentage crop yield loss for each of the soil agronomic factor, the seed agronomic factor and the weather agronomic factor. In one example, the system 20 and the computing element 32 analyze all possible iterations of agronomic factors, to solve for the limiting agronomic factor. In another example, the system 20 and computing element 32 does not analyze all of the possible iterations but picks random combinations of agronomic factors, establishes upper and lower limits for yield loss, and continues iterating until the dataset has been narrowed down to only a handful of combinations from which the user can identify the limiting agronomic factor.

For illustrative purposes and to demonstrate principles of the disclosure, these three exemplary agronomic factors and their yield losses may be presented in a graphical form. This exemplary representation is not intended to be limiting upon the present disclosure. Rather, the agronomic factors and their yield loss may be represented in a variety of manners and all of such possibilities are intended to be within the spirit and scope of the present disclosure.

With particular reference to FIG. 18, an example of possible yield losses for the three agronomic factors is illustrated. In this example, the system 20 and computing element 32 determine that weather (e.g., water or other resultant of weather) has the highest percentage crop yield loss compared to seed and soil. Thus, in this example, the system 20 and computing element 32 determine that weather is the limiting factor. As a result of this determination, the system 20 and the computing element 32 communicate the limiting factor to one or more devices over one or more networks 44 as described elsewhere in the present disclosure. The user then may store the information for later use (e.g., document for crop planning purposes and use at a later time when planting crops), the user may take action, and/or the system 20 and computing element 32 communicate the limiting factor to one or more agricultural devices where the one or more agricultural devices may operate in accordance with limiting factor data.

In this illustrated example, weather is the limiting factor. The system 20 and the computing element 32 may communicate to a user that weather is the limiting factor. In one example, if water is the weather condition that contributes to weather being the limiting factor, the user may activate the irrigation system associated with the land area of interest to increase the water supply, thereby decreasing the percentage crop yield loss associated with weather. In some examples, activation of the irrigation system may include activating an above grade irrigation system or a below grade irrigation system. With respect to an above grade example such as a center pivot, the center pivot irrigation system may be activated to turn on the water supply or may be activated to turn off the water depending on how the water is limiting the crop yield (e.g., too much water or too little water). With respect to a below grade example such as a tiling system, the tiling irrigation system may be closed to maintain water in the soil or may be opened to allow water to run out of the soil depending on how the water is limiting the crop yield (e.g., too little water or too much water). In any of the above examples, the activation may either be performed manually by a user or by the system 20 and the computing element 32. When the yield loss associated with weather decreases below a percentage crop yield loss for another agronomic factor, then the other agronomic factor becomes the limiting factor. In FIG. 19, the yield loss for weather has dropped below the yield loss for seed, which now has the highest yield loss. Thus, the system 20 and computing element 32 determine that seed is now the limiting factor (see FIG. 19). The system 20 and the computing element 32 communicate data (e.g., an alert) associated with the new or change in limiting factor (e.g., see as illustrated in FIG. 19) to one or more devices over one or more networks 44. The system 20 and the computing element 32 continually analyze inputted data to determine the limiting factor and communicate any changes in limiting factor so appropriate action can be taken.

It should be understood that the system 20 and/or computing element 32 may create zones of a land area of interest based on any agronomic factor, soil characteristic, seed characteristic, and/or weather characteristic either individually or in combination in any quantities and in any proportions, and all of such possibilities are intended to be within the spirit and scope of the present disclosure.

The system 20 of the present disclosure may also determine a limiting factor based on different variables or characteristics. In one example, the system 20 determines a limiting factor by relying on economic indicators or variables, either in part or in whole. For example, the system 20 determines a limiting factor for providing a highest crop yield at a lowest cost. In this example, the system 20 determines costs associated with a wide variety of factors, variables, steps during the growth process, analyzes the costs, and considers the costs to determine a limiting factor. Some of the possible costs associated with the growth process include, but are not limited to: input costs from, for example, seeds, nitrogen, irrigation, pesticides, etc.; fuel charges; labor costs; etc. Additionally, the system 20 may determine and rely on other economic factors such as, for example, cost per seed (e.g., may be different at different planting rates—bulk discount or efficiency goes up as more seeds are planted resulting in lower cost per seed); break even cost; various cost breakdowns of inputs (e.g., nitrogen cost per pass in zone/field, cost of a unit of measure of nitrogen (e.g., pound, etc.), fuel efficiency, etc.); or a wide variety of other factors. In this manner, the system 20 would be able to provide optimal results of both agriculture and economics.

With reference to FIGS. 37-44, further examples of systems, methods and apparatuses of the present disclosure are provided. These examples assist with getting information to an area of interest or on-site. For example, a farmer, equipment operator or agricultural equipment may receive information while at an area of interest (e.g., a field). The information received by the farmer, equipment operator or agricultural equipment may be associated with precision farming and may assist with performing agricultural actions that improve a crop's yield. In examples where a farmer or equipment operator receive the information, the farmer or equipment operator may operate agricultural equipment in accordance with the received information to perform one or more agricultural actions. In examples where agricultural equipment receives the information, the agricultural equipment may perform one or more agricultural actions with or without interaction by a user or farmer.

The following examples of systems, methods and apparatuses are not intended to limit the present disclosure. Rather, the following examples are intended to demonstrate at least some of the principles of the present disclosure. Alternatives exist to these examples and are intended to be within the intended spirit and scope of the present disclosure. Additionally, the following examples are not intended to only include the features, structures and functionalities described and illustrated specifically therewith. Rather, features, structures and functionalities of any of the examples may be combined in any manner with any of the features, structures and functionalities of any of the other examples, and all of such possible combinations are intended to be within the spirit and scope of the present disclosure.

In one example, with reference to, for example, FIGS. 37-39 and 41, an agricultural system 300 includes a first component 302, a second component 304 and a network 306. The first component 302 includes a network interface 308 (see, e.g., 41) for receiving an agricultural prescription 310 over the network 306 and the agricultural prescription 310 is comprised of at least one agricultural characteristic 312 and at least one agricultural action 314 (see, e.g., 42). The second component 304 is in communication with the first component 302 and is configured to receive the agricultural prescription 310 from the first component 302. Additionally, the second component 304 is configured to output the at least one agricultural action 314. In one example, the agricultural prescription 310 may be comprised of more than one agricultural characteristic 312 and/or more than one agricultural action 314 (see, e.g., FIG. 43). In one example, more than one agricultural prescription 310 may be transmitted or communicated over the network 306 from the server 334 to the first component 302.

In one example, the at least one agricultural characteristic 312 may be associated with at least one of water, nitrogen, seed variety, seed rate, a pest, an undesired plant and a fungus, and the at least one agricultural action 314 may be associated with at least one of planting, irrigating, fertilizing, tilling, harvesting, spraying, fumigating and fertigating. The agricultural characteristic 312 and agricultural action 314 are not intended to be limited to these possibilities, but, rather, are capable of including many other characteristics and actions, and all of such possibilities are intended to be within the spirit and scope of the present disclosure.

In one example, the at least one agricultural characteristic 312 and the at least one agricultural action 314 correspond to each other. For example, the at least one agricultural characteristic 312 may be associated with water and the at least one agricultural action 314 may be associated with irrigating. In such an example, water may be applied before planting or growing season, at any time during the growing season up to harvest with the crop at any growth stage, or after the harvest. Also, for example, the at least one agricultural characteristic 312 may be associated with nitrogen and the at least one agricultural action 314 may be associated with fertilizing. In such an example, nitrogen may be applied before planting or growing season, at any time during the growing season up to harvest with the crop at any growth stage, or after the harvest. Also, in such an example, nitrogen may be applied multiple times throughout the year and application of the nitrogen may be split into two or more applications to correspond, respectively, with two or more growth stages of the crop. Further, for example, the at least one agricultural characteristic 312 may be associated with a seed characteristic and the at least one agricultural action 314 may be associated with at least one of planting, irrigating, fertilizing, tilling, harvesting, spraying, fumigating and fertigating. In such an example, the seed characteristic may be associated with at least one of seed variety or seed rate.

Figure 43:
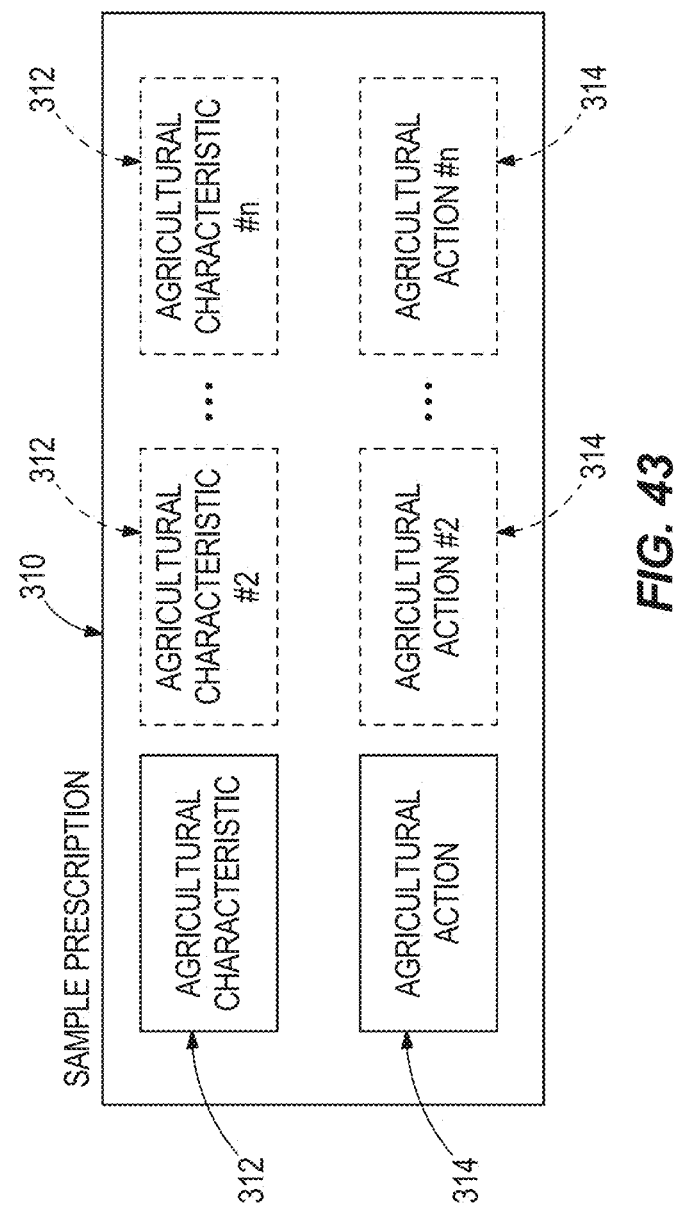
FIG. 43 is a block schematic diagram of one example of an agricultural prescription of the agricultural system of the present disclosure.

In one example, with reference to, for example, FIG. 43, the agricultural prescription 310 is comprised of a plurality of agricultural characteristics 312. In such an example, the plurality of agricultural characteristics 312 may be associated with at least two of water, nitrogen, seed variety, seed rate, a pest, an undesired plant and a fungus, or any other agricultural characteristic.

Figure 42:
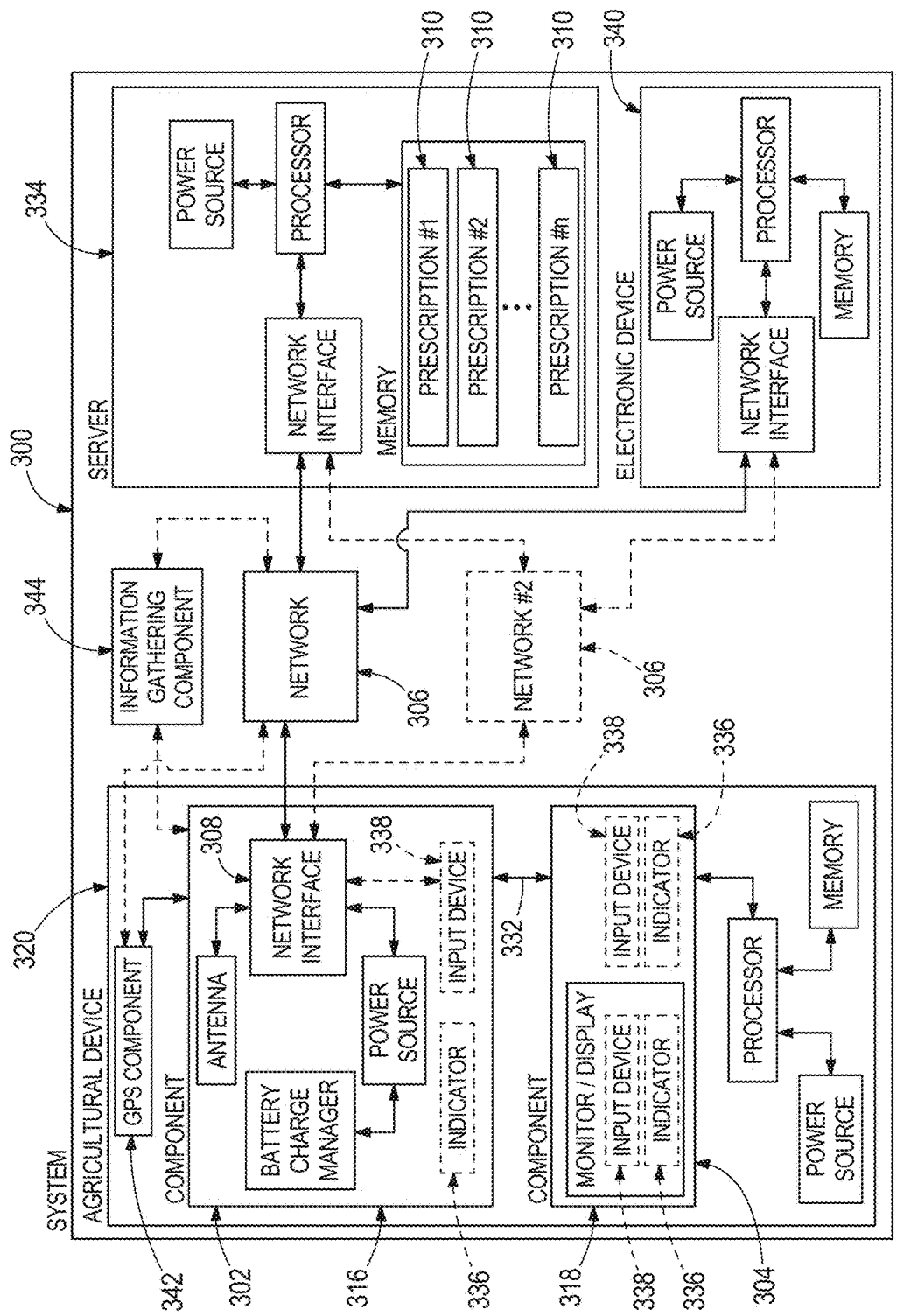
FIG. 42 is a block schematic diagram of one example of an agricultural system of the present disclosure, the agricultural system is configured to perform at least a portion of the functionality and methods of the present disclosure.

In one example, with reference to, for example, FIG. 42, the agricultural system 300 includes one network 306. The network 306 may be a wide variety of types of networks including, but not limited to, a cellular network, a WI-FI network, an Internet, a local network, and a wide-area-network, and the network interface 308 may be complementary to the network 306 in order to facilitate at least one of transmitting data over and receiving data from the network 306. In one example, the network 306 is a cellular network and the network interface 308 is a cellular interface.

In one example, with reference to, for example, FIG. 42, the agricultural system 300 includes a plurality of networks 306. These networks 306 may be a wide variety of types of networks including, but not limited to, a cellular network, a WI-FI network, an Internet, a local network, and a wide-area-network. The plurality of networks 306 may be the same type of network or may be different types of networks. In such an example, the first component 302 may be configured to receive the agricultural prescription 310 over the plurality of networks 306. Also, in such an example, the network interface 308 may be the sole network interface 308 of the first component 302 and may be configured to receive the agricultural prescription 310 over either only one network 306 or over the plurality of networks 306. Further, in such an example, the first component 302 may alternatively include a plurality of network interfaces 308 and the plurality of network interfaces 308 may be configured to receive the agricultural prescription 310 over the plurality of networks 306.

In one example, with reference to, for example, FIGS. 37-42, the first component 302 may include a first housing 316 and the second component 304 may include a second housing 318 independent from the first housing 316.

In another example, the first component 302 and the second component 304 are within a single housing.

The first component 302 may be coupled to an agricultural device 320 in a variety of manners. The agricultural device may be any type of agricultural device and may pertain to large machines including, but not limited to, tractors, combines, sprayers, planters, irrigation systems, or any other type of large machine associated with agriculture, or smaller machines including, but not limited to, motors, pumps, valves, seed meters, rate controllers, sprinkler heads, pneumatic devices, hydraulic devices, actuators, or any other type of machine associated with agriculture. While words like large and small may have been used to distinguish between different types of agricultural devices, use of these words is not intended to be limiting. Rather, it is intended that the agricultural devices of the systems disclosed herein may be any type, size, shape, apparatus associated with agriculture.

In one example, the first component 302 may be fastened to the agricultural device 320. In such an example, the first component 302 may be fastened with one or more of any type of fasteners 322. For example, the fastener(s) 322 may be screws, nuts-and-bolts, rivets, lag bolts, or any other type of fastener. In another example, the first component 302 may be magnetically coupled to the agricultural device 320. In such an example, the housing 316 of the first component 302 may include a magnet 324 and may be magnetically coupled to a portion of the agricultural device 320 that facilitates magnetic coupling.

Figure 41:
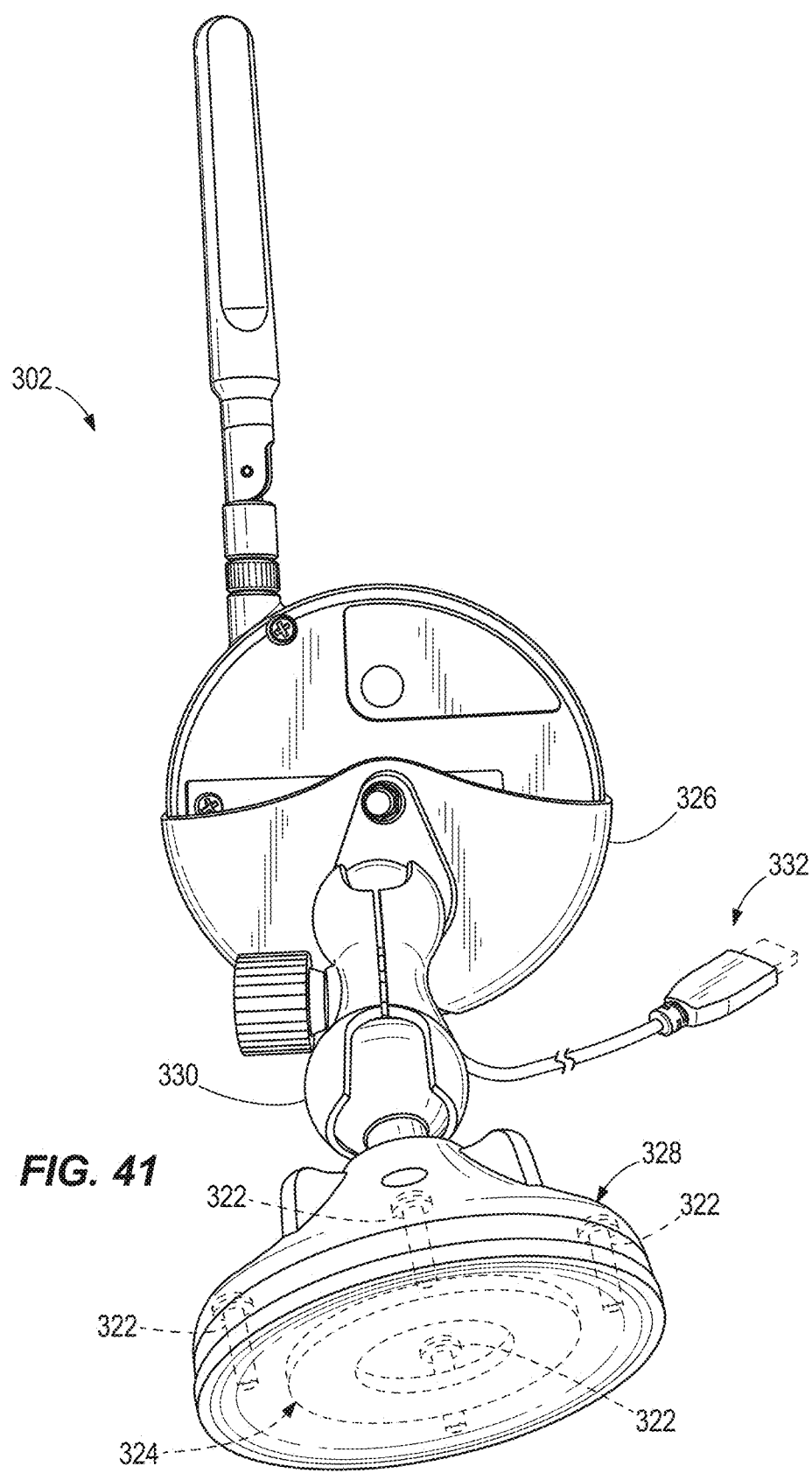
FIG. 41 is a rear view of the component shown in FIG. 40.

In one example, with reference to, for example, FIG. 41, the first component 302 is selectively positionable in a cradle 326 for supporting the first component 302. The cradle 326 is moveably coupled to a base 328 via a movable joint 330. In the illustrated example, the joint 330 is a ball-and-socket joint allowing movement along three axes, thereby provide flexibility in positioning the first component 302. The base 328 may be coupled to an agricultural device 320 in a variety of manners. In one example, fasteners 322 may be used to fasten the base to the agricultural device 320. In another example, the base 328 may include a magnetic member 324 configured to selectively magnetically couple the base 328, and therefore the first component 302, to the agricultural device 320.

In one example, the output of the at least one agricultural action 314 may include displaying the at least one agricultural action 314. In such an example, the second component 304 may be configured to display the agricultural prescription 310. Additionally, in such an example, the second component 304 may be a display or monitor (see, e.g., FIGS. 37-39) and the display or monitor may be configured to display the agricultural prescription 310.

In another example, the output of the at least one agricultural action 314 may include communicating at least one operating instruction to an agricultural device 320 (see, e.g., FIG. 42). In such an example, at least one operating instruction may be associated with at least one of planting, irrigating, fertilizing, tilling, harvesting, spraying, fumigating and fertigating.

In one example, with reference to, for example, FIGS. 37-42, the agricultural system 300 further includes an electrical coupling 332 coupled to the first component 302 and the second component 304, and the electrical coupling 332 may be configured to communicate data and power between the first component 302 and the second component 304. In such an example, the electrical coupling 332 may be a USB coupling. In one example, the electrical coupling 332 may be hardwired to one of the first component 302 and the second component 304 and may be selectively connectable to the other of the first component 302 and the second component 304. In such an example, the electrical coupling 332 is hardwired to the first component 302 and is selectively connectable to the second component 304. In another example, the electrical coupling 332 may be selectively connectable to both the first component 302 and the second component 304. In still another example, the electrical coupling 332 may be hardwired to both the first component 302 and the second component 304.

In one example, the first component 302 is configured to interrupt power over the electrical coupling 332 between the first component 302 and the second component 304, and wherein the first component 302 is configured to continue operating with power interrupted over the electrical coupling 332. In another example, a power circuit within the first component is interrupted such that the second component perceives the electrical coupling 332 between the first and second components 302, 304 has been interrupted or disconnected. In such an example, the first component may include a power source and does not lose data or power cycling due to the power source. Also, in such an example, the power circuit can be reinstated to eliminate the interruption and again reconnect the electrical coupling 332 between the first and second components 302, 304. In such an example, the second component may announce or indicate the interruption and reconnection of the first component 302 to the second component 304 over the electrical coupling 332.

In one example, with reference to, for example, FIG. 42, the first component 302 is configured to receive the agricultural prescription 310 over the network 306 from a server 334. The agricultural prescription 310 may be created and then stored in the server 334, and the server 334 may transmit notification data over the network 306 to the first component 302 when the agricultural prescription 310 is stored on the server 334. In one example, one of the first component 302 or the second component 304 may activate an indicator 336 (see, e.g., FIG. 40 with respect to the first component 302; second component indicator may be, for example, on the display or monitor) when the first component 302 receives the notification data from the server 334. The indicator 336 may be one or more of a visible indicator and/or an audible indicator. A visible indicator 336 may be a wide variety of types of indicators such as, but not limited to, an illumination device, a lighting element, a light bulb, a light-emitting-diode, a liquid crystal display, an icon on a monitor or display, physical movement of an item, movement of an item from a first position or condition to a second position or condition, or any other possible manner or structure of visibly indicating. In the illustrated exemplary embodiment, the visible indicator 336 is indicia, such as, for example, a downward arrow among other indicia, illuminated by a light emitting diode. In examples including a visible indicator 336, the visible indicator 336 is at least one of activation of an illumination device on the first component 302, activation of an illumination device on the second component 304, display of an item on the first component 302, and display of an item on the second component 304. An audible indicator 336 may be a wide variety of types of audible indicators including, but not limited to, audio emitted by an audio device such as, for example, a speaker, an instrument capable of emitting sound, or any other manner or structure of audibly indicating.

In one example, with reference to, for example, FIG. 42, at least one of the first component 302 and the second component 304 may include an input device 338. In such an example, the first component 302 may be configured to transmit activation data over the network 306 to the server 334 upon activation of the input device 338. The input device 338 may be a wide variety of input devices and all of such possibilities are intended to be within the spirit and scope of the present disclosure. For example, the input device 338 may be a keyboard, a keypad, a mouse, a mechanical or electrical button or switch, a touch screen display, a voice recognition device, or any other type of input device.

In one example, the server 334 may be configured to transmit the agricultural prescription 310 over the network 306 to the first component 302 upon receipt of the activation data.

In one example, activation of the input device 338 may be the sole action required to be performed by a user to facilitate transmission of the agricultural prescription 310 to the first component 302. In another example, the first component 302 may be self-authenticating and may not require identifying information to be provided by a user for transmission of the agricultural prescription 310 to the first component 302 from the server 334.

In one example, the server 334 may transmit a text message over the network 306 to the first component 302 when the agricultural prescription 310 is stored on the server 334.

In one example, the agricultural prescription 310 may be generated by a computing element or electronic device 340 (see, e.g., FIG. 42) and stored in the server 334, and the server 334 may transmit notification data over the network 306 to the first component 302 when the agricultural prescription 310 is stored on the server 334. In one example, the computing element 340 may evaluate agronomic factors impacting a particular crop, identify the agronomic factor limiting crop yield, and generate the agricultural prescription 310 based on the agronomic factor that limits crop yield.

In one example, with reference to, for example, FIG. 42, the agricultural system 300 further includes a GPS component 342 configured to generate GPS data associated with a global position of the GPS component 342. In such an example, the GPS data may be transmitted over the network 306 to the server 334. In one example, the GPS component 342 may transmit the GPS data over the network 306 to the server 334. In another example, the GPS component 342 may be in communication with the first component 302 and the first component 302 may transmit the GPS data over the network 306 to the server 334. In one example, the agricultural prescription 310 is one of a plurality of agricultural prescriptions 310 stored in the server 334, the plurality of agricultural prescriptions 310 may each be associated with particular GPS data, and the one of the agricultural prescriptions 310 transmitted over the network 306 to the first component 302 may be associated with the GPS data transmitted over the network 306 to the server 334. In such an example, the GPS data may be associated with an area of interest. Areas of interest may include, but not be limited to, one of a portion of a field, an entire field, multiple fields, a portion of a crop, an entire crop, or any other agricultural area.

In one example, the GPS component 342 may be part of an agricultural device 320 and the GPS data may be associated with a global position of the agricultural device 320.

In one example, the first component 302 may receive the agricultural prescription 310 from the server 334 as a result of the server 334 receiving the GPS data over the network 306. In such an example, the server 334 may authenticate the GPS data and may transmit the agricultural prescription 310 after authenticating the GPS data. Also, in such an example, no action may be required by a user to transmit GPS data over the network 306 to the server 334 and for the first component 302 to receive the agricultural prescription 310 from the server 334. In another example, a single action may be required by a user to transmit GPS data over the network 306 to the server 334 and for the first component 302 to receive the agricultural prescription 310 from the server 334.

In one example, with reference to, for example, FIG. 42, the agricultural system 300 may further include an information gathering component 344 configured to gather, collect or sense information pertaining to agricultural characteristics 312 and generate agricultural data associated with the gathered information.

In one example, the information gathering component 344 may be a sensor. In another example, the information gathering component 344 may be a camera. In a further example, the information gathering component 344 may be both a sensor and a camera.

The agricultural data collected by the sensor, camera or both may relate to a variety of agricultural characteristics including, but not limited to, seed type, weather conditions, insect infestation, plant maturity, canopy temperature, soil temperature, carbon dioxide ($CO_2$), sunlight exposure, presence and/or absence of plants, plant population, plant stand indicative of crop health, Normalized Difference Vegetation Index (NDVI), the presence of absence of plant silks or other organic matter, crop moisture, soil slope and/or various soil characteristics, including soil type, soil pH, nitrogen, mineralization, soil moisture, soil moisture holding capacity, soil slope, plant height, leaf size, quantity of leaves, quantity of agricultural product (e.g., corn ears, soybean pods, etc.), size of agricultural product (e.g., corn tassel length, ear length/size, soybean pod length/size, etc.), root lodging, quantity of agricultural products dropped to the ground from the plant (e.g., dropped corn ears, dropped soybean pods, etc.), stalk lodging, plant appearance, stay green rating, crop rot (e.g., ear rot, kernel rot, stalk rot, etc.), intactness, grain quality rating, agricultural product shape (e.g., corn ear shape, etc.), ear type (e.g., flex, semi-flex or fixed), husk cover, kernel depth, shank length, cob diameter, moisture percent, brittle snapping, tassel branch angle, days to silk, pollen shed, leaf sheath pubescence, quantity of leaves above top ear node, lateral tassel branches, number of ears per stalk husk color, leaf waves and creases, ear taper, length of internode, length of tassel, kernel rows, kernel length, kernel thickness, husk extension, position of ear, Goss' Wilt and Stewert's Wilt ratings, leaf blight, gray leaf spot rating, kernel pop score, southern rust rating, or any other agricultural characteristic. For example, multi-spectral and hyper-spectral camera or a video cameras may be utilized for measuring or characterizing normalized difference vegetation index (NDVI). Sensors for determining canopy or soil temperature may include infrared, infrared imaging, laser and thermal sensors. Sensors for determining the presence and features of a plant may include visible wavelength imaging sensors, ultrasonic sensors, capacitive sensors, photoelectric sensors, luminescence sensors, contrast sensors, video cameras, color sensors (for identify a difference in color between the soil and the plant) and laser distance sensors. Sensors for determining $CO_2$ amounts around plants (for example soybeans) may include any $CO_2$ sensor, such as, for example, the MG811 $CO_2$ sensor available from Futurlec Co. Ltd. 136 Broadmeadow Rd., New South Wales, AU 2292 (futurlec.com).

The information gathering component 344 may collect information and generate data associated with any number of the above or other agricultural characteristics. In one example, the information gathering component 344 collects information and generates data associated with a single agricultural characteristic. In another example, the information gathering component 344 collects information and generates data associated with a plurality of agricultural characteristics. In one example, the information gathering component 344 simultaneously collects information associated with presence and/or absence of a plant and a height of the plant. In one example, the information gathering component 344 collects information and generates data associated with presence and/or absence of a plant, skipped plantings, double plantings, plant size (e.g., stalk diameter), leaf count, (e.g., measures plant width), weed or other undesirable agricultural plant presence, plant height, plant height variance, soil temperature, plant temperature, and NDVI.

In one example, the information gathering component 344 may be positioned on an agricultural device 320. The agricultural device 320 may be any type of agricultural device 320 disclosed herein (e.g., see FIGS. 37-39) or alternative agricultural devices not specifically identified herein. The information gathering component 344 may be coupled to an agricultural device 320 in a variety of orientations. In one example, the information gathering component 344 may be oriented to aim downward toward the ground. In such an example, at least some of the emissions or imaging from the information gathering component 344 may be perpendicular to the ground. Also, in such an example, the information gathering component 344 would be coupled to the agricultural device 320 to look downward at the soil and/or plants from above. This downward orientation of the information gathering component 344 may be useful when plants are relatively new or young and have not reached a certain height. In another example, the information gathering component 344 may be oriented to aim horizontally. In such an example, at least some of the emissions or imaging from the information gathering component 344 may be horizontal or parallel to the ground. Also, in such an example, the information gathering component 344 would be coupled to the agricultural device 320 to look horizontally or parallel to the soil. This horizontal orientation of the information gathering component 344 may be useful when plants are older and have reached a certain age or height and the information gathering component 344 may move down a space between rows of plants. In a further example, the information gathering component 344 may be oriented at any position such as, for example, upward, any angled position between vertical and horizontal, etc.

In one example, if the information gathering component 344 is collecting information associated with plant height across a land area of interest, the system may account for the measured plant heights and provide a rolling average plant height. In one example, if the information gathering component 344 is collecting information associated with plant height across a land area of interest, the system may monitor the measured plant heights and compare the measured plant heights to an acceptable range of plant heights based on an age of the plant. If the measured plant height is outside the acceptable range of plant heights based on the age of the plant, the system identifies the plant associated with the measured height as being outside the acceptable height. In one example, the information gathering component 344 is coupled to an agricultural device 320 at a fixed height relative to the soil and/or the agricultural device 320. In this example, the information gathering component 344 measures a distance between itself and a plant (or absence of a plant) to determine at least one of a presence of a plant and/or a height of the plant. In another example, the information gathering component 344 is coupled to an agricultural device 320 at a fixed height relative to the soil and/or the agricultural device 320. In this example, the information gathering component 344 simultaneously measures a distance between itself and a plant and a distance from itself to the soil to determine at least one of a presence of a plant and/or a height of a plant.

In one example, the information gathering component 344 may be configured to measure at least one of soil temperature, plant temperature and/or ambient air temperature. In one example, the information gathering component 344 includes an imaging camera for detecting and measuring at least one of soil temperature, plant temperature and/or ambient air temperature. In one example, the information gathering component 344 includes an infrared sensor. In one example, the information gathering component 344 includes a plurality of infrared sensors. In such an example, the plurality of infrared sensors may either sense or detect temperature at a plurality of points or may cooperate to sense or detect temperature at a single point. In one example, the information gathering component 344 includes 5 infrared sensors. In such an example, the plurality of infrared sensors may either sense or detect temperature at a plurality of points (e.g., between 2 points and 5 points) or may cooperate to sense or detect temperature at a single point (e.g., the infrared sensors are focused at a single point). In one example, the one or more infrared sensors may be used to sense or detect soil moisture.

In one example, the system may include a plurality of information gathering components 344. The information gathering components 344 may collect information associated with the same agricultural characteristic(s) or different agricultural characteristics.

The agricultural data may be transmitted over the network 306 to the server 334. In such an example, the information gathering component 344 may transmit the agricultural data over the network 306 to the server 334. In another example, the information gathering component 344 may be in communication with the first component 302 and the first component 302 may transmit the agricultural data over the network 306 to the server 334.

In one example, the agricultural data may be relied upon to generate the agricultural prescription 310. In such an example, the information gathering component 344 would gather information pertaining to agricultural characteristics 312, generate agricultural data associated with the gathered information, and transmit or communicate the agricultural data to the server 334. In such an example, an electronic device 340 (see, e.g., FIG. 42) may receive the agricultural data from the server 334 over the network 306, may generate the agricultural prescription 310 based on the agricultural data, and may transmit the agricultural prescription 310 over the network 306 to the server 334 where the agricultural prescription 310 is stored. In such an example, the first component 302 may be configured to receive the agricultural prescription 310 over the network 306 from the server 334. The electronic device 340 may be a wide variety of types of electronic devices including, but not limited to, a computing element, a personal computer, a laptop, a mobile electronic device, a tablet, a cellular enabled phone, a smartphone, or any other appropriate type of electronic device.

In one example, the agricultural data may be relied upon to generate a second agricultural prescription 310 based on the agricultural data, and the second agricultural prescription 310 is different than the agricultural prescription 310. In such an example, the first component 302 may be configured to receive the second agricultural prescription 310 over the network 306 from the server 334.

In one example, an electronic device 340 (see, e.g., FIG. 42) may receive the agricultural data from the server 334 over the network 306, may generate a second agricultural prescription 310 based on the agricultural data, and may transmit the second agricultural prescription 310 over the network 306 to the server 334 where the second agricultural prescription 310 is stored. In such an example, the first component 302 may be configured to receive the second agricultural prescription 310 over the network 306 from the server 334. The electronic device 340 may be a wide variety of types of electronic devices including, but not limited to, a computing element, a personal computer, a laptop, a mobile electronic device, a tablet, a cellular enabled phone, a smartphone, or any other appropriate type of electronic device.

In one example, each of the plurality of agricultural prescriptions 310 may be associated with particular agricultural data, and the one of the agricultural prescriptions 310 transmitted over the network 306 to the first component 302 may be associated with the agricultural data transmitted over the network 306 to the server 334.

Referring now to FIGS. 45-52, one example of an information gathering component 344 is illustrated. This example of the information gathering component 344 is provided to demonstrate at least some of the principles of the present disclosure and is not intended to be limiting. In the illustrated example, the information gathering component 344 includes a housing 500, an emitting element 502, a receiving element 504, a plurality of ports 506 configured to be input and output ports, at least one indicator 508, a processor 510, memory 512, a network interface 514, a Bluetooth component 515, an inertial measurement unit (IMU) 517, and a possible GPS component 342. The emitting element 502 may emit a wide variety of emissions and the receiving element 504 may receive a wide variety of emissions reflected back to the receiving element 504 after being emitted by the emitting device. The emitting element 502 and the receiving element 504 are complementary to each other in that the receiving element 504 is configured to receive the type of emission(s) emitted from the emitting element 502. In the illustrated example, the emitting element 502 is an illumination device 502 such as, for example, one or more high powered light emitting diodes (LEDs) 502, and the emission is light. In one example, the LED(s) 502 may emit light at a wavelength between about 800 nanometers and about 1000 nanometers. In one example, the LED(s) 502 may emit light at a wavelength of about 920 nanometers. In one example, the illumination device 502 may pulse light and modulate a signal. In this example, modulation may be used to distinguish light emitted from the emitting element from ambient light. In one example, the information gathering component 344 may be a LIDAR device.

In the illustrated example, the receiving element 504 is configured to receive light reflected back from a surface(s) engaged by the light emissions from the emitting element 502. The receiving element 504 may be a wide variety of devices configured to detect light. In one example, the receiving element 504 may be a photo detector 504. In such an example, the photo detector 504 may be a wide variety of photo detectors such as, for example, a 16 segment photo diode, a 32 segment photo diode, a 64 segment photo diode, a 128 segment photo diode, etc. In another example, the photo detector 504 may be a camera such as, for example, a camera with 300×300 pixels, etc. In the illustrated example, a transparent or translucent lens 516 covers the receiving element 504. In one example, the lens 516 may be convex. In another example, the lens 516 may be substantially flat or planar. In a further example, the lens 516 may be concave.

Figure 52:
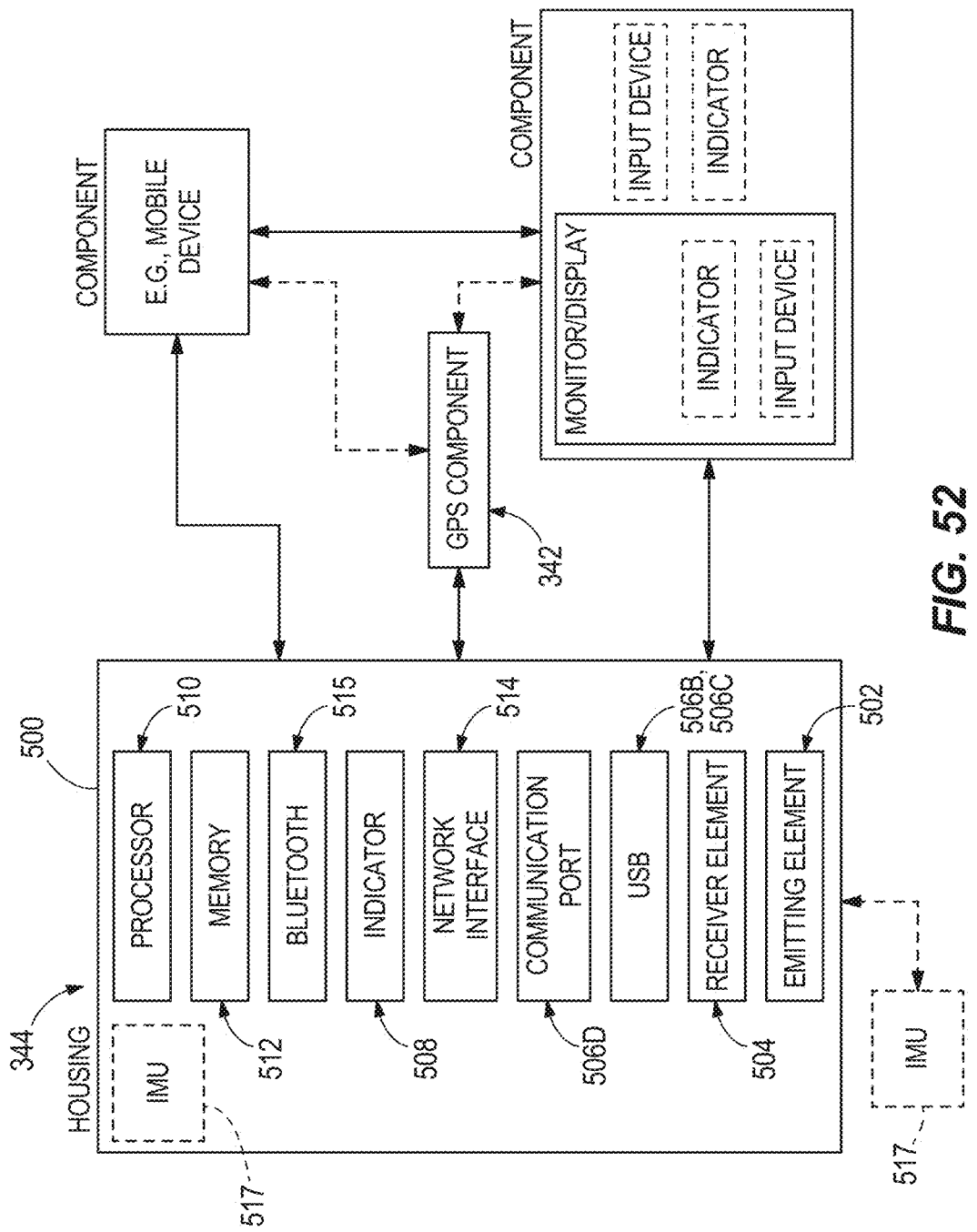
FIG. 52 is a block schematic diagram of one example of at least a portion of an agricultural system of the present disclosure including one example of an information gathering component.

In one example and with reference to FIG. 52, the information gathering component 344 illustrates the processor 510, the memory 512, the plurality of ports 506, the network interface 514, the indicator 508, the Bluetooth component 515, the IMU 517 and a possible GPS component 342. In the illustrated example, the plurality of ports 506 are comprised of a serial port 506A, a USB port 506B, a micro USB port 506C, a communication port 506D and a power supply connection 506E. The USB port 506B and the micro USB port 506C may be used as input and/or output ports, thereby facilitating input and/or output of agricultural data based on information associated with the monitored agricultural characteristic(s). In one example, the USB port 506B and the micro USB port 506C may also be used to supply electrical power to the information gathering component 344 from an electrical power source. In the illustrated example, the power supply connection 506E may be used to couple a power supply cord to the information gathering component 344 in order to supply electrical power to the information gathering component 344 from an electrical power source.

The network interface 514 may be a wide variety of types of network interfaces and may be configured to interface with a wide variety of types of networks including, but not limited to, cellular, Wi-Fi, the Internet, local area networks, wide area networks, any other type of network described herein or other types of networks. In one example, the network interface 514 may be in electrical communication with one or more of the plurality of ports 506. In another example, the network interface 514 may not be in electrical communication with the plurality of ports 506. In one example, the information gathering component 344 includes the IMU 517. In this example, the IMU 517 assists with ensuring accurate measurements and readings as the agricultural device 320 and information gathering component 344 traverse a land area of interest. Traversing a field may result in vibration, vertical and horizontal movement (e.g., bouncing around), or other external influences applied to the agricultural device 320 and the information gathering component 344, thereby impacting the measurements or readings taken by the information gathering component 344. The IMU 517 is configured to accommodate these external influences and ensure the measurements or readings are more accurate. In one example, the system includes the IMU 517 and the IMU 517 cooperates with the information gathering component 344 to accommodate external influences and ensure more accurate measurements or readings by the information gathering component 344.

In one example, the information gathering component 344 includes an onboard GPS component 342 configured to generate data associated with the global position of the information gathering component 344 and send or communicate the GPS data to the server 334 where the GPS data may be utilized to generate a prescription 310. In another example, the information gathering component 344 does not have an onboard GPS component and instead operates in conjunction with an external GPS component 342 that may be associated with the agricultural device 320. In a further example, the information gathering component 344 does not have an onboard GPS component and instead operates in conjunction with an external GPS component 342 that may be associated with the electrical component. In one example, the indicator 508 is configured to provide an indication to a user. In one example, the indicator 508 may be an illumination device 508. In another example, the indicator 508 may be a display or monitor 508.

In examples where the information gathering component 344 is coupled to an agricultural device 320 that moves, the information gathering component 344 is configured to gather or collect agricultural information associated with one or more agricultural characteristic(s) while moving. Agricultural devices 320 may move at a relatively high speed and the information gathering component 344 is configured to gather or collect agricultural information at the relatively high speed. In one example, the elements (e.g., hardware and/or software) of the information gathering component 344 are able of processing data at a high rate. In one example, the information gathering component 344 is configured to process data at about 100 Hz. In another example, the information gathering component 344 is configured to process data at a rate greater than 100 Hz. In one example, the information gathering component 344 is capable of sending or communicating data out at about 10 Hz.

The information gathering component 344 is capable of operating in a variety of manners, collecting or gathering a wide variety of information associated with a wide variety of agricultural characteristics and generating agricultural data associated with the agricultural characteristics. In one example, the emitting element 502 may emit pulsed streams of light, the light may reflect off of one or more objects (such as, for example, plants when they are present or soil when a plant is not present), the receiving element 504 will receive or sense the reflected back light, and measure a time period from emission of light to receipt of reflected back light. The measured time period will identify information about the object that was contacted by the light. In one example, if the light engages a plant, a first time period will be measured by the information gathering component 344. In one example, if light engages soil, a second time period will be measured by the information gathering component 344 and the second time period will be different than the first time period. In examples where the light engages a plant, the measured time period may also indicate a height of the plant. For example, the time period will be longer if the plant is short and the time period will be shorter if the plant is taller.

Figure 53:
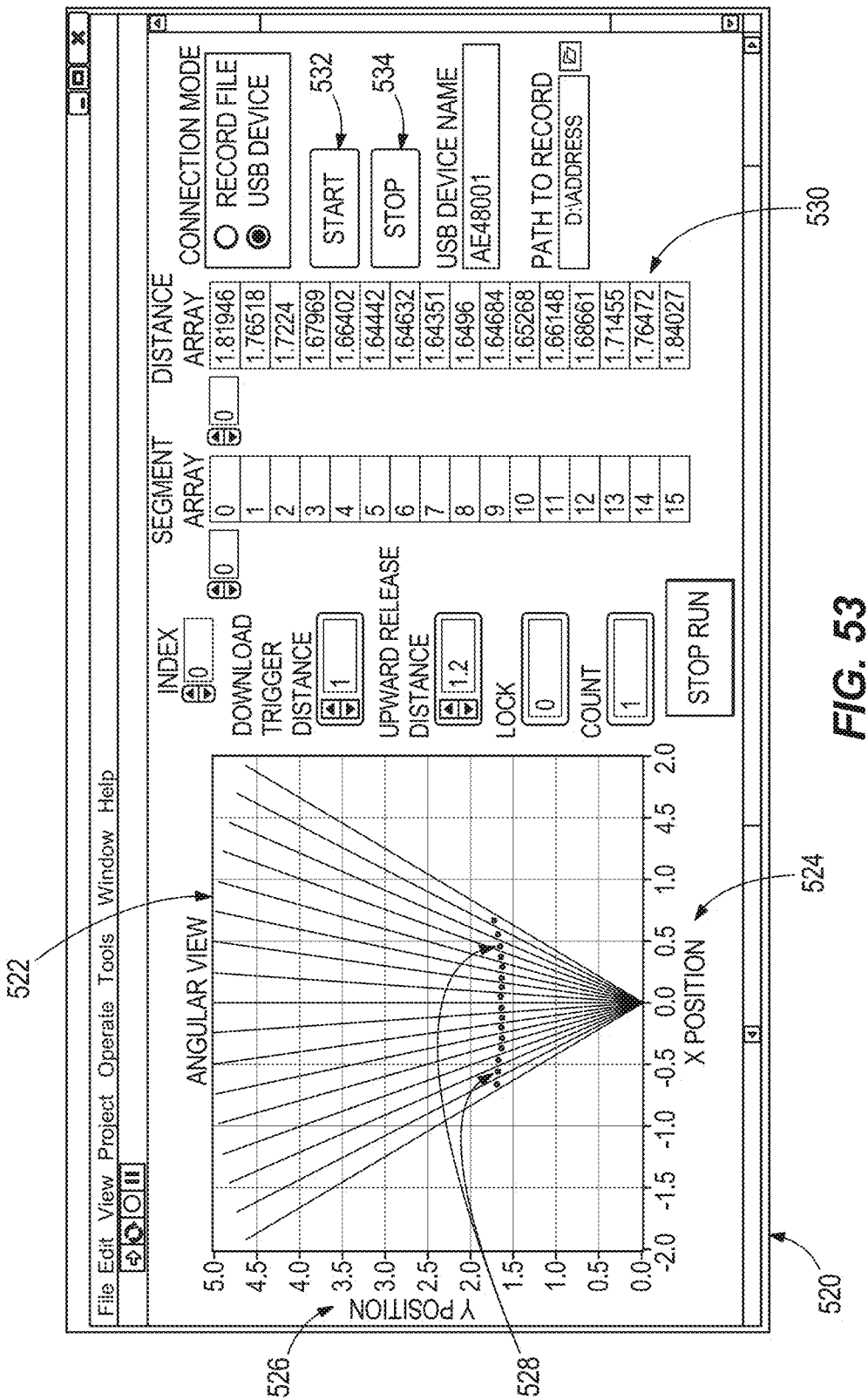
FIG. 53 is one example of a user interface provided by an agricultural system of the present disclosure associated with an information gathering component of the agricultural system.
Figure 54:
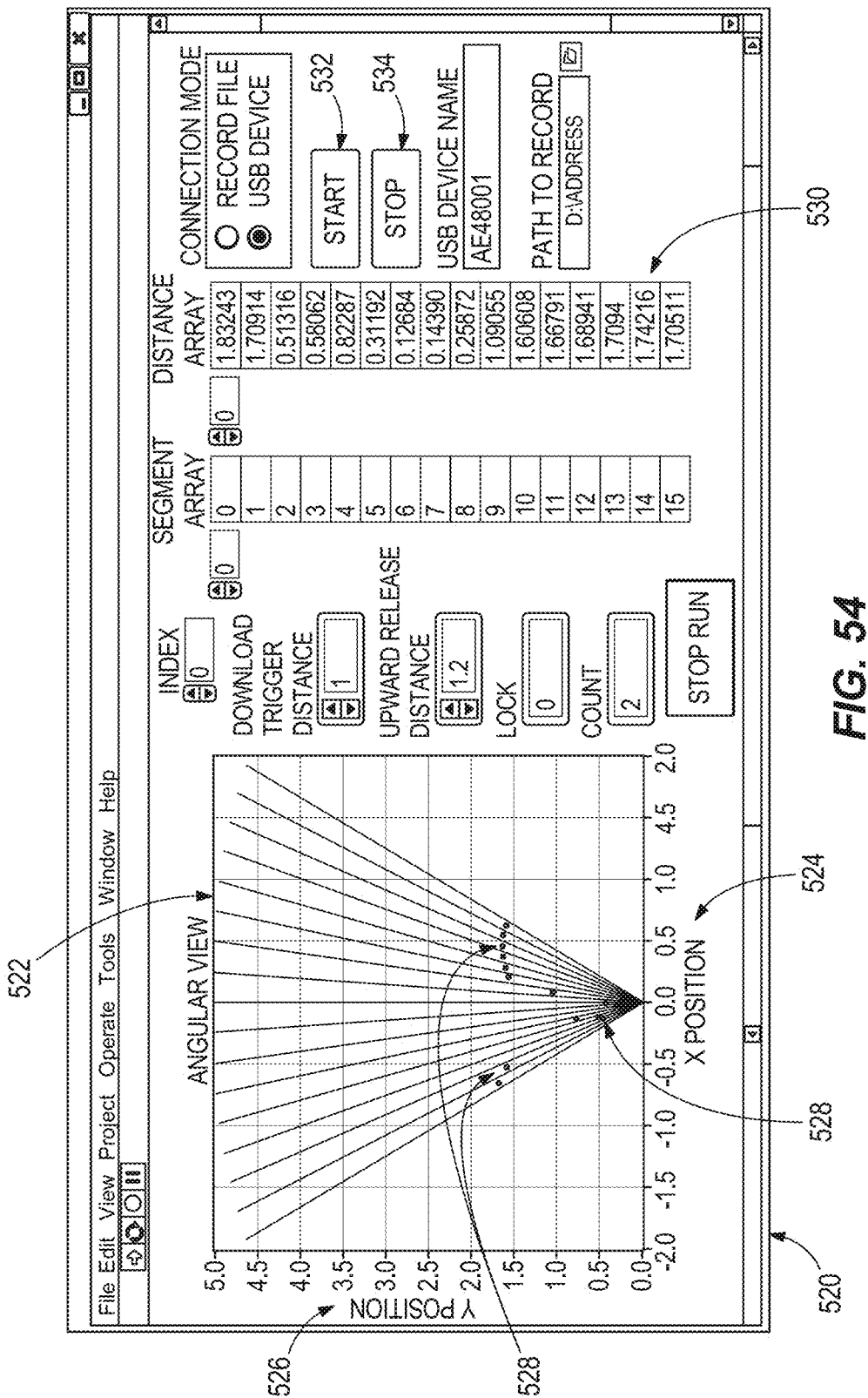
FIG. 54 is one example of a user interface provided by an agricultural system of the present disclosure associated with an information gathering component of the agricultural system.

Referring now to FIGS. 53 and 54, examples of user interfaces 520 provided by the system are illustrated and are associated with agricultural information collected or gathered by the information gathering component 344. With respect to FIG. 53, the user interface 520 includes a display portion 522 for displaying images or graphics to a user that convey information collected or gathered by the information gathering component 344. In this example, the display portion 522 includes a two-dimensional area having two axes, one for the X-position 524 and one for the Y-position 526. A plurality of indicators 528 (e.g., green dots) appear on the display portion 522 and represent a plurality of objects engaged by emissions (e.g., light) emitted by the emitting device 502 (e.g., LEDs) and reflected back to the information gathering component 344 where the receiving element 504 received the reflected back emissions. In one example, as illustrated in FIG. 53, the indicators 528 are generally in a straight line indicating that no plants or objects were detected by the information gathering component 344. The user interface 520 also displays a plurality of numeric distances 530 associated with each indicator 528 representing the numerical value associated with each indicator 528.

The user interface 520 also includes icons 532, 534 that may be selected or activated by a user to start and stop the information gathering process.

With respect to FIG. 54, the user interface 520 includes a display portion 522 for displaying images or graphics to a user that convey information collected or gathered by the information gathering component 344. In this example, the display portion 522 includes a two-dimensional area having two axes, one for the X-position 524 and one for the Y-position 526. A plurality of indicators 528 (e.g., green dots) appear on the display portion and represent a plurality of objects engaged by emissions (e.g., light) emitted by the emitting device 502 (e.g., LEDs) and reflected back to the information gathering component 344 wherein the receiving element 504 received the reflected back emissions. In one example, the indicators 528 are at various positions along the Y-position axis 526 indicating that plants are present and were detected by the information gathering component 344. In this example, indicators 528 with their Y-position value nearer the X-position axis 524 means a plant was detected by the information gathering component 344. This example of the user interface 520 also displays a plurality of numeric values 530 associated with each indicator 528 representing the numerical value associated with each plant. The user interface 520 also includes icons 532, 534 that may be selected or activated by a user to start and stop the information gathering process.

In one example, the first component 302 may have identifying data, and the first component 302 may transmit the identifying data over the network 306 to the server 334. In such an example, no action is required by a user to transmit the identifying data over the network 306 to the server 334 and for the first component 302 to receive the agricultural prescription 310 from the server 334. In another example, a single action may be required by a user to transmit the identifying data over the network 306 to the server 334 and for the first component 302 to receive the agricultural prescription 310 from the server 334.

Figure 44:
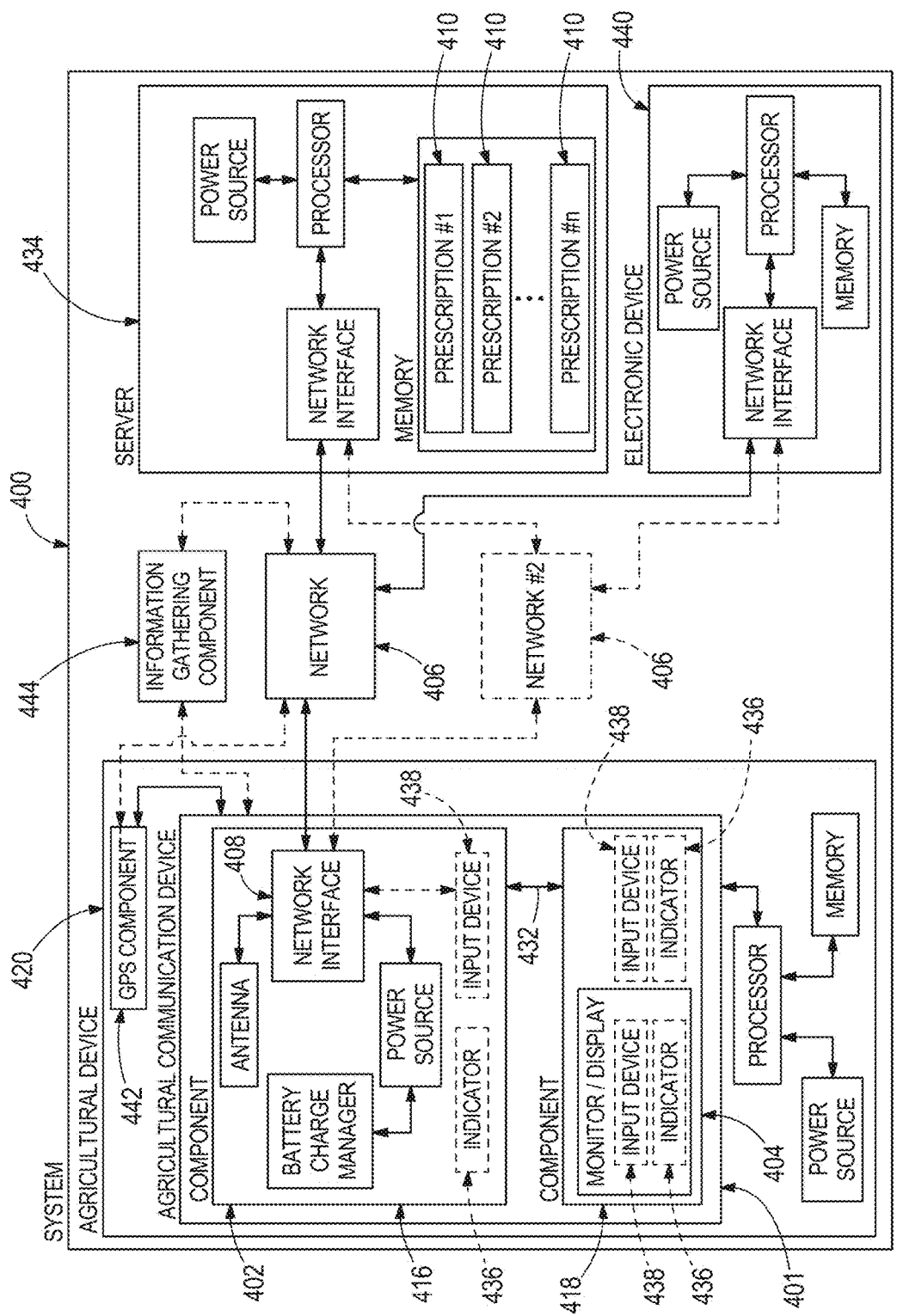
FIG. 44 is a block schematic diagram of one example of an agricultural system of the present disclosure, the agricultural system is configured to perform at least a portion of the functionality and methods of the present disclosure.
Figure 45:
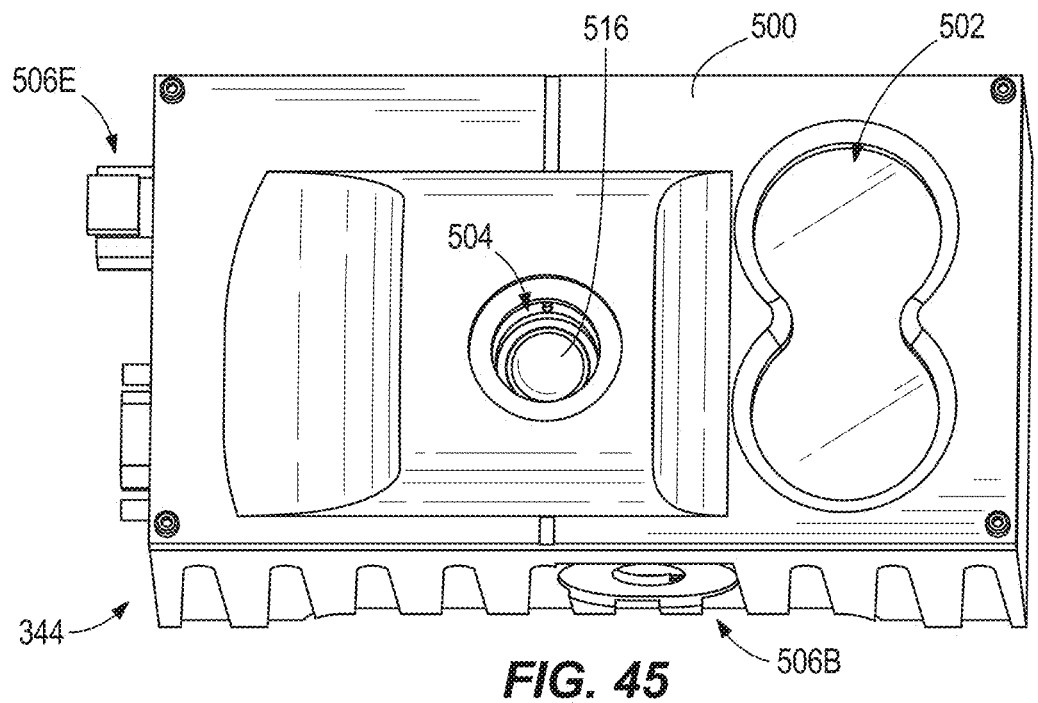
FIG. 45 is a perspective view of one example of an information gathering component of an agricultural system of the present disclosure.
Figure 46:
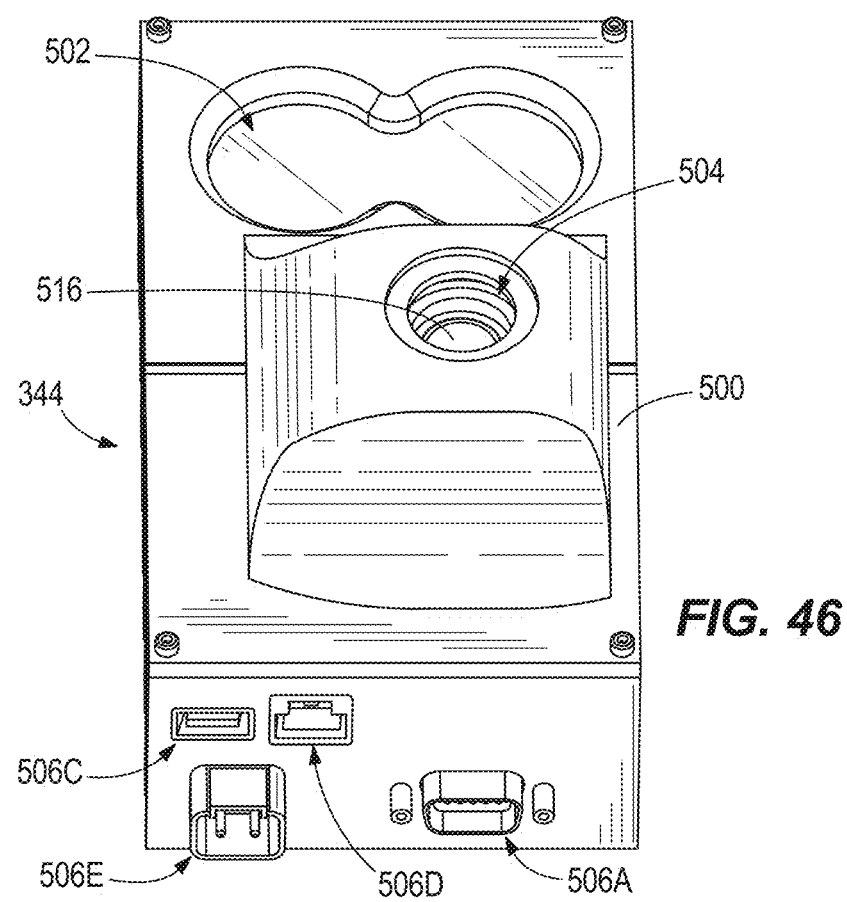
FIG. 46 is another perspective view of the information gathering component shown in FIG. 45.
Figure 47:
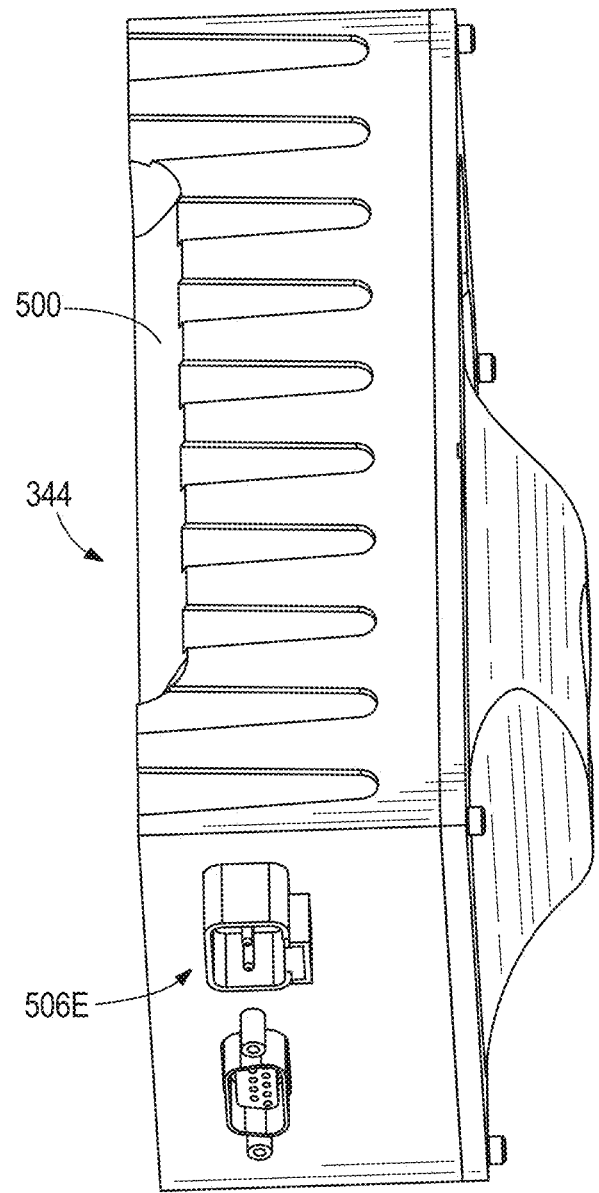
FIG. 47 is a side view of the information gathering component shown in FIG. 45.
Figure 48:
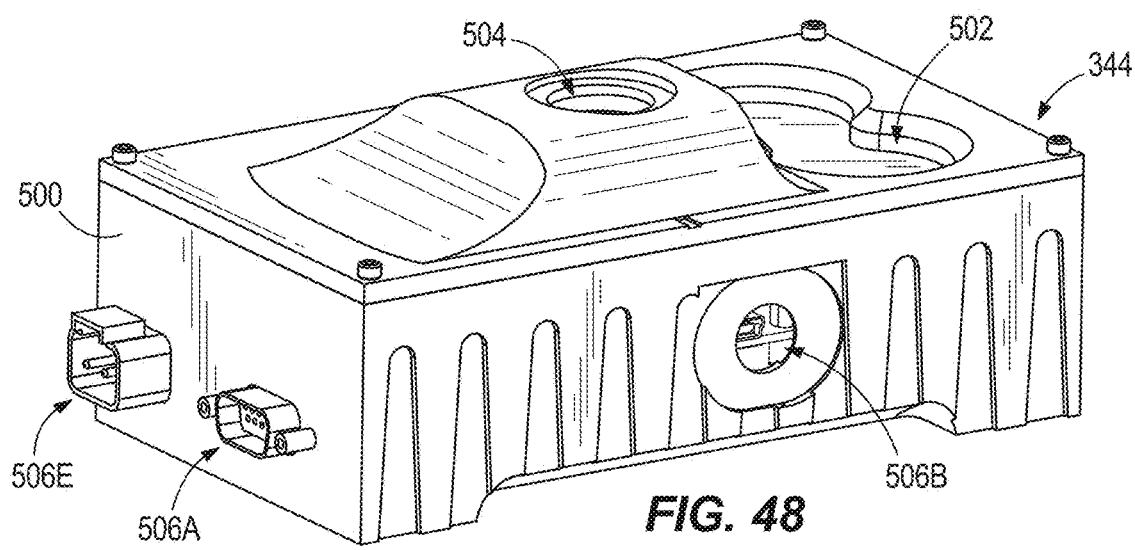
FIG. 48 is another perspective view of the information gathering component shown in FIG. 45.
Figure 49:
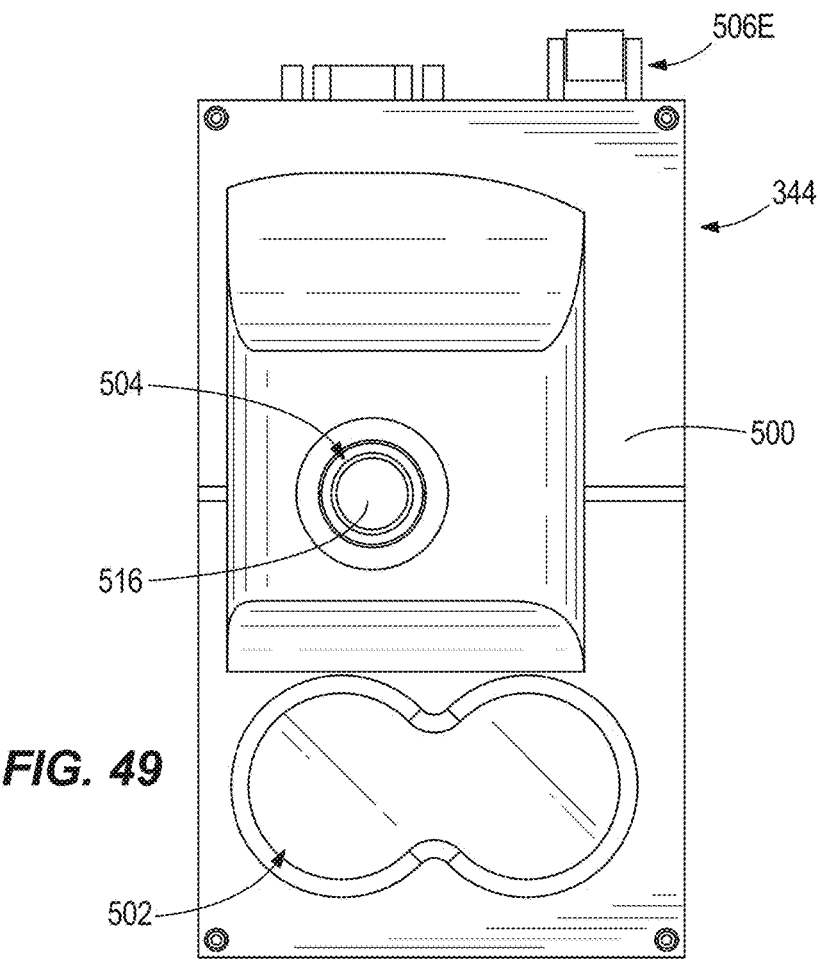
FIG. 49 is a side view of the information gathering component shown in FIG. 45.
Figure 50:
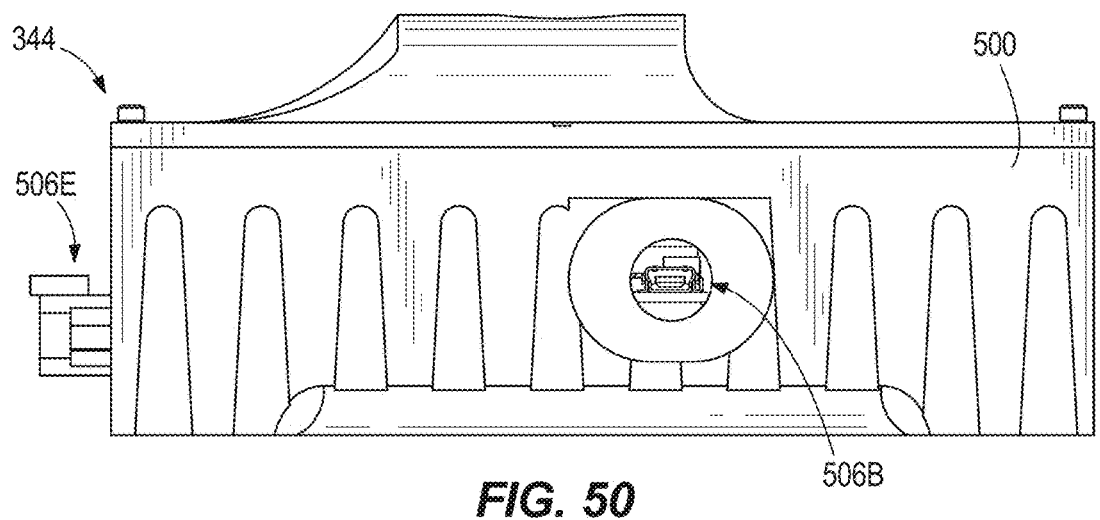
FIG. 50 is another side view of the information gathering component shown in FIG. 45.
Figure 51:
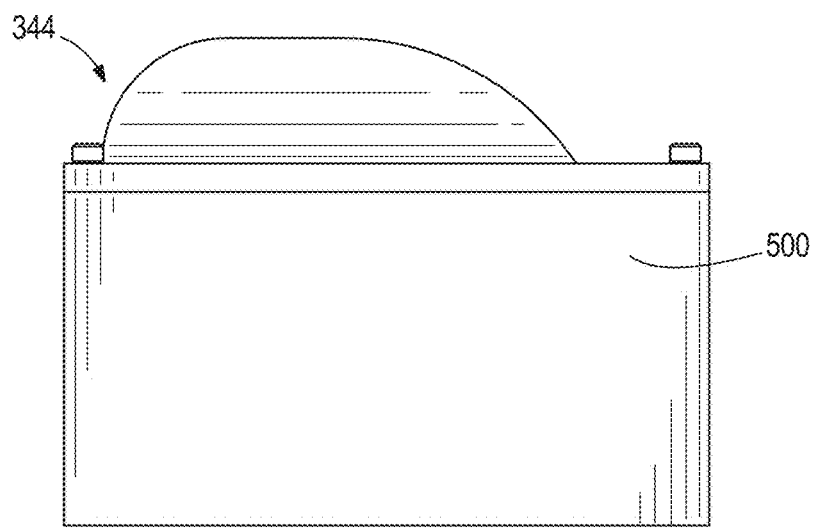
FIG. 51 is another side view of the information gathering component shown in FIG. 45.

In one example, with reference to, for example, FIG. 44, an agricultural system 400 includes an agricultural device 420 and an agricultural communication device 401 including a network interface 408 for receiving an agricultural prescription 410 over a network 406, and the agricultural prescription 410 may include at least one agricultural characteristic 412 and at least one agricultural action 414. The agricultural device 420 may be configured to output the agricultural action 414. This agricultural system 400 and the elements thereof are capable of having similar features, structures, functionalities, alternatives, etc., of the agricultural systems described herein and thus will not be repeated. For example, the agricultural device 420 may be at least one of a tractor, a planter, a fertilizer, a combine, a spraying device, a harvesting device, and an agricultural implement (e.g., tillage or soil conditioning equipment).

In one example, the agricultural communication device 401 may include the first component 402 including the network interface 408 for receiving the agricultural prescription 410 over the network and the second component 404 in communication with the first component 402 and configured to receive the agricultural prescription 410 from the first component 402. In such an example, the second component 404 may be configured to output the at least one agricultural action 414.

In one example, the first component 402 may have a first housing and the second component 404 may have a second housing independent from the first housing. In another example, the first component 402 and the second component 404 may be within a single housing. In one example, the agricultural communication device 401 includes a housing and the first component 402 and the second component 404 are within the housing. In such an example, the agricultural communication device 401 is a single component capable of performing all of the operations and functionalities of the first component 402 and the second component 404 in other agricultural systems disclosed herein. The agricultural communication device 401 may be referred to as a component of the agricultural system 400 since it is the single component capable of performing the desired operations and functionalities.

In one example, with reference to, for example, FIG. 44, the agricultural communication device 401 may include a display or monitor and the display or monitor may be configured to display the at least one agricultural action 414.

In one example, with reference to, for example, FIG. 44, the agricultural communication device 401 may be configured to receive the agricultural prescription 410 over the network 406 from a server 434. In such an example, the agricultural prescription 410 may be created and stored in the server 434, and the server 434 may transmit notification data over the network 406 to the agricultural communication device 401 when the agricultural prescription 410 is stored on the server 434. In such an example, the agricultural communication device 401 may activate an indicator 436 (see, e.g., FIG. 44) when the agricultural communication device 401 receives the notification data from the server 434. In such an example, the indicator 436 may be at least one of a visible indicator and an audible indicator. In another example, the indicator 436 may be both a visible indicator and an audible indicator. In examples where the indicator 436 is a visible indicator, the visible indicator 436 is at least one of activation of an illumination device on the agricultural communication device and display of an item on the agricultural communication device.

In one example, with reference to, for example, FIG. 44, the agricultural communication device 401 may include an input device 438, and the agricultural communication device 401 may be configured to transmit activation data over the network 406 to the server 434 upon activation of the input device 438. In such an example, the server 434 may be configured to transmit the agricultural prescription 410 over the network 406 to the agricultural communication device 401 upon receipt of the activation data.

In one example, activation of the input device 438 is the sole action required to be performed by a user to facilitate transmission of the agricultural prescription 410 to the agricultural communication device 401.

In another example, the agricultural communication device 401 is self-authenticating and does not require identifying information to be provided by a user for transmission of the agricultural prescription 410 to the agricultural communication device 401 from the server 434.

In one example, the server 434 may transmit a text message over the network 406 to the agricultural communication device 401 when the agricultural prescription 410 is stored on the server 434.

In one example, with reference, for example, to FIG. 44, the agricultural prescription 410 may be generated by the computing element or electronic device 440 and stored in the server 434, and the server 43 may transmit notification data over the network 406 to the agricultural communication device 401 when the agricultural prescription 410 is stored on the server 434.

In one example, with reference to, for example, FIG. 44, the agricultural communication device 401 may be configured to receive the agricultural prescription 410 over the network 406 from the server 434, the agricultural system 400 may further include the GPS component 442 which is configured to generate GPS data associated with the global position of the GPS component 442. The GPS data may be transmitted over the network 406 to the server 434. In one example, the GPS component 442 transmits the GPS data over the network 406 to the server 434. In another example, the GPS component 442 may be in communication with the agricultural communication device 401 and the agricultural communication device 401 may transmit the GPS data over the network 406 to the server 434. In such an example, each of the plurality of agricultural prescriptions 410 (see, e.g., FIG. 44) are associated with particular GPS data, and the one of the agricultural prescriptions 410 transmitted over the network 406 to the agricultural communication device 401 may be associated with the GPS data transmitted over the network 406 to the server 434.

In one example, the agricultural communication device 401 may receive the agricultural prescription 410 from the server 434 as a result of the server 434 receiving the GPS data over the network 406. In such an example, the server 434 may authenticate the GPS data and may transmit the agricultural prescription 410 after authenticating the GPS data. Also, in such an example, no action may be required by a user to transmit GPS data over the network 406 to the server 434 and for the agricultural communication device 401 to receive the agricultural prescription 410 from the server 434. In another example, a single action may be required by a user to transmit GPS data over the network 406 to the server 434 and for the agricultural communication device 401 to receive the agricultural prescription 410 from the server 434.

In one example, with reference to, for example, FIG. 44, the agricultural system 400 also includes an information gathering component 444 configured to gather information pertaining to agricultural characteristics 412 and generate agricultural data associated with the gathered information. The agricultural data may be transmitted over the network 406 to the server 434. In such an example, the information gathering component 444 may transmit the agricultural data over the network 406 to the server 434. Alternatively, in such an example, the information gathering component 444 may be in communication with the agricultural communication device 401 and the agricultural communication device 401 may transmit the agricultural data over the network 406 to the server 434.

In one example, the agricultural data may be relied upon to generate the agricultural prescription 410. In such an example, the information gathering component 444 would gather information pertaining to agricultural characteristics 412, generate agricultural data associated with the gathered information, and transmit or communicate the agricultural data to the server 434. In such an example, an electronic device 440 (see, e.g., FIG. 44) may receive the agricultural data from the server 434 over the network 406, may generate the agricultural prescription 410 based on the agricultural data, and may transmit the agricultural prescription 410 over the network 406 to the server 434 where the agricultural prescription 410 is stored. In such an example, the first component 402 may be configured to receive the agricultural prescription 410 over the network 406 from the server 434. The electronic device 440 may be a wide variety of types of electronic devices including, but not limited to, a computing element, a personal computer, a laptop, a mobile electronic device, a tablet, a cellular enabled phone, a smartphone, or any other appropriate type of electronic device.

In one example, the agricultural data may be relied upon to generate the second agricultural prescription 410 based on the agricultural data with the second agricultural prescription 410 being different than the agricultural prescription 410. In one example, the agricultural communication device 401 may be configured to receive the second agricultural prescription 410 over the network 406 from the server 434.

In one example, the plurality of agricultural prescriptions 410 (see, e.g., FIG. 44) may each be associated with particular agricultural data, and the one of the agricultural prescriptions 410 transmitted over the network 406 to the agricultural communication device 401 may be associated with the agricultural data transmitted over the network 406 to the server 434.

In one example, the agricultural communication device 401 may have identifying data, and the agricultural communication device 401 may transmit the identifying data over the network 406 to the server 434. In this example, no action may be required by a user to transmit the identifying data over the network 406 to the server 434 and for the agricultural communication device 401 to receive the agricultural prescription 410 from the server 434. In another example, a single action may be required by a user to transmit the identifying data over the network 406 to the server 434 and for the agricultural communication device 401 to receive the agricultural prescription 410 from the server 434.

The agricultural systems disclosed herein and alternatives thereof are capable of performing a wide variety of operations, functionalities and processes. At least a portion those operations, functionalities and processes are disclosed herein and are provided to demonstrate at least a portion of the principles of the present disclosure. The agricultural systems may be capable of performing other operations, functionalities and processes and all of such possibilities are intended to be within the spirit and scope of the present disclosure.

In one example, a method of operating an agricultural system is provided. The method may include transmitting the agricultural prescription over the network from a server, and receiving the agricultural prescription with the first component 302 of the agricultural system. The first component 302 may include a network interface and the agricultural prescription may be comprised of at least one agricultural characteristic and at least one agricultural action. The method also includes communicating the agricultural prescription from the first component 302 to the second component 304, and outputting the at least one agricultural action with the second component 304.

It should be understood that any of the features and structures of the agricultural systems described herein and their associated operations and/or functionalities may result in one or more steps of a process or method, and such step(s) may be incorporated into this example of a method of operating an agricultural system in any quantity and any combination, and all of such possibilities are intended to be within the spirit and scope of the present disclosure.

In one example, another method of operating an agricultural system is provided. The method may consist essentially of generating the agricultural prescription with a computing device with the agricultural prescription comprised of at least one agricultural characteristic and at least one agricultural action, storing the agricultural prescription on the server, transmitting data from the first component 302 of the agricultural system to the server over a network, transmitting the agricultural prescription from the server to the first component 302 over the network upon receipt of the data by the server, receiving the agricultural prescription with the first component 302, communicating the agricultural prescription to the second component 304 of the agricultural system, and outputting the agricultural action with the second component 304.

It should be understood that any of the features and structures of the agricultural systems described herein and their associated operations and/or functionalities may result in one or more steps of a process or method, and such step(s) may be incorporated into this example of a method of operating an agricultural system in any quantity and any combination, and all of such possibilities are intended to be within the spirit and scope of the present disclosure.

In one example, a further method of operating an agricultural system is provided. The method consists essentially of generating the agricultural prescription with the computing device with the agricultural prescription comprised of at least one agricultural characteristic and at least one agricultural action, storing the agricultural prescription on the server, and transmitting the agricultural prescription from the server to a component of the agricultural system over a network.

It should be understood that any of the features and structures of the agricultural systems described herein and their associated operations and/or functionalities may result in one or more steps of a process or method, and such step(s) may be incorporated into this example of a method of operating an agricultural system in any quantity and any combination, and all of such possibilities are intended to be within the spirit and scope of the present disclosure.

In one example, yet another method of operating an agricultural system is provided. The method consists essentially of receiving the agricultural prescription over the network with the first component 302 of the agricultural system. The agricultural prescription is comprised of at least one agricultural characteristic and at least one agricultural action. The method also consisting essentially of communicating the agricultural prescription to the second component 304 of the agricultural system, outputting the agricultural action with the second component 304, and executing the agricultural action with the agricultural device.

It should be understood that any of the features and structures of the agricultural systems described herein and their associated operations and/or functionalities may result in one or more steps of a process or method, and such step(s) may be incorporated into this example of a method of operating an agricultural system in any quantity and any combination, and all of such possibilities are intended to be within the spirit and scope of the present disclosure.

It should also be understood that words like transmit, communicate, etc., used with respect to data transfers are not intended to be restrictive to a particular manner in which data is transferred between two elements. That is, these and other words do not imply a pushing or pulling requirement of the data between two elements. Rather, the present disclosure intends that data may be transferred between two elements in any manner and all of such possibilities are intended to be within the spirit and scope of the present disclosure.

It should also be understood that any feature, function, process, and/or method of the present disclosure may be customizable by a user and all of such customization is intended to be within the spirit and scope of the present disclosure. For example, zones and/or slopes may be customized by a user as desired.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the systems, methods, processes, apparatuses and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the systems, apparatuses, devices, methods and/or processes via the use of block diagrams, schematics, flowcharts, and/or examples. Insofar as such block diagrams, schematics, flowcharts, and/or examples contain one or more functions and/or operations, it will be understood by those within the art that each function and/or operation within such block diagrams, schematics, flowcharts, or examples can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to, physically mateable and/or physically interacting components, and/or wirelessly interactable and/or wirelessly interacting components, and/or logically interacting and/or logically interactable components.

Unless specifically stated otherwise or as apparent from the description herein, it is appreciated that throughout the present disclosure, discussions utilizing terms such as "accessing," "aggregating," "analyzing," "applying," "brokering," "calibrating," "checking," "combining," "comparing," "conveying," "converting," "correlating," "creating," "defining," "deriving," "detecting," "disabling," "determining," "enabling," "estimating," "filtering," "finding," "generating," "identifying," "incorporating," "initiating," "locating," "modifying," "obtaining," "outputting," "predicting," "receiving," "reporting," "sending," "sensing," "storing," "transforming," "updating," "using," "validating," or the like, or other conjugation forms of these terms and like terms, refer to the actions and processes of a computer system or computing element (or portion thereof) such as, but not limited to one or more or some combination of: a visual organizer system, a request generator, an Internet coupled computing device, a computer server, etc. In one example, the computer system and/or the computing element may manipulate and transform information and/or data represented as physical (electronic) quantities within the computer system's and/or computing element's processor (s), register(s), and/or memory(ies) into other data similarly represented as physical quantities within the computer system's and/or computing element's memory(ies), register(s) and/or other such information storage, processing, transmission, and/or display components of the computer system(s), computing element(s) and/or other electronic computing device(s). Under the direction of computer-readable instructions, the computer system(s) and/or computing element(s) may carry out operations of one or more of the processes, methods and/or functionalities of the present disclosure.

Those skilled in the art will recognize that it is common within the art to implement apparatuses and/or devices and/or processes and/or systems in the fashion(s) set forth herein, and thereafter use engineering and/or business practices to integrate such implemented apparatuses and/or devices and/or processes and/or systems into more comprehensive apparatuses and/or devices and/or processes and/or systems. That is, at least a portion of the apparatuses and/or devices and/or processes and/or systems described herein can be integrated into comprehensive apparatuses and/or devices and/or processes and/or systems via a reasonable amount of experimentation.

Although the present disclosure has been described in terms of specific embodiments and applications, persons skilled in the art can, in light of this teaching, generate additional embodiments without exceeding the scope or departing from the spirit of the present disclosure described herein. Accordingly, it is to be understood that the drawings and description in this disclosure are proffered to facilitate comprehension of the present disclosure, and should not be construed to limit the scope thereof.

What is claimed is:

1. An agricultural system comprising:
    a remote server operatively coupled to a wireless network and to at least one database, the remote server configured to access agricultural data in the at least one database;
    a first data processor mounted to an agricultural device, the agricultural device having at least one of a motor, an actuator, a pump, a valve, and a meter;
    the first data processor having an antenna in operative communication with the wireless network, and coupled to a network interface for transmitting data to the wireless network and for receiving data from the wireless network, wherein the network interface receives an agricultural prescription from the remote server, and wherein the agricultural prescription includes an agricultural characteristic and an agricultural action;
    a second data processor mounted to the agricultural device and in operative communication with the first data processor, the second data processor configured to receive the agricultural prescription from the first data processor and output the agricultural action, wherein outputting the agricultural action controls the at least one of the motor, actuator, pump, valve, and meter of the agricultural device; and
    an information processor in operative communication with at least one of the first data processor and the second data processor, the information processor having at least one sensor configured to gather information pertaining to the agricultural characteristic, wherein the information processor generates further agricultural data associated with the gathered information and transmits the further agricultural data to the remote server over the wireless network.

2. The agricultural system of claim 1, wherein the first data processor is configured to receive the agricultural prescription over the network from the remote server, and wherein the agricultural data is configured to be transmitted over the wireless network to the remote server.

3. The agricultural system of claim 1, wherein the information processor transmits the agricultural data over the wireless network.

4. The agricultural system of claim 1, wherein the information processor is in communication with the first data processor and the first data processor transmits the agricultural data over the wireless network.

5. The agricultural system of claim 4, wherein the agricultural data is relied upon to generate a second agricultural prescription based on the agricultural data, and wherein the second agricultural prescription is different than the agricultural prescription.

6. The agricultural system of claim 5, wherein the first data processor is configured to receive the second agricultural prescription over the wireless network.

7. The agricultural system of claim 4, wherein an electronic device receives the transmitted agricultural data, generates a second agricultural prescription based on the agricultural data, and transmits the second agricultural prescription.

8. The agricultural system of claim 7, wherein the electronic device transmits the second agricultural prescription to the remote server where the second agricultural prescription is stored.

9. The agricultural system of claim 7, wherein the first data processor is configured to receive the second agricultural prescription over the wireless network.

10. The agricultural system of claim 7, wherein the electronic device is a computing element.

11. The agricultural system of claim 7, wherein the electronic device is at least one of a personal computer, a laptop, a mobile electronic device, a tablet, a cellular enabled phone, and a smartphone.

12. The agricultural system of claim 1, wherein the agricultural prescription is one of a plurality of agricultural prescriptions, wherein the plurality of agricultural prescriptions are each associated with particular agricultural data, and wherein the one of the agricultural prescriptions received by the first data processor over the wireless network is associated with the agricultural data transmitted over the wireless network.

13. The agricultural system of claim 1, wherein the agricultural data is associated with one of water, sunlight, temperature, humidity, barometric pressure, soil characteristics, nitrogen, a pest, an undesired plant and a fungus.

14. The agricultural system of claim 1, wherein the information processor further includes a light emitter configured to emit light and a light detector configured to receive light.

15. The agricultural system of claim 14, wherein the light emitter is configured to emit light that engages an object, the light is configured to reflect back toward the light detector after engaging the object, and the light detector is configured to receive the reflected back light, and wherein the agricultural data is associated with the light received by the light detector.

16. The agricultural system of claim 15, wherein the agricultural data is associated with at least one of a presence of a plant, an absence of a plant and a height of a plant.

17. The agricultural system of claim 14, wherein the light emitter is an illumination device and the sensor is a photo detector.

18. The agricultural system of claim 1, wherein the information processor includes a camera.

19. The agricultural system of claim 1, wherein the information processor is physically mounted to the agricultural device.

20. The agricultural system of claim 19, wherein the agricultural device is one of a tractor, a harvester, a planter, a sprayer, an agricultural implement, an unmanned aerial vehicle, a manned aerial vehicle, an all-terrain vehicle, an automobile, and an irrigation device.

21. The agricultural system of claim 1, further comprising a housing, wherein the first data processor is at least partially positioned inside the housing.

22. The agricultural system of claim 21, wherein the second data processor is at least partially positioned in the housing.

23. An agricultural system comprising:
a remote server operatively coupled to a wireless network and to at least one database, the remote server configured to access agricultural data in the at least one database;
a computing element including a processor and a memory, the computing element operatively mounted to an agricultural device, the agricultural device having at least one of a motor, an actuator, a pump, a valve, and a meter;
the computing element coupled with an antenna and in operative communication with the wireless network, and coupled to a network interface for transmitting data to the wireless network and for receiving data from the wireless network;
wherein the computing element receives from the network interface, data that identifies a limiting agronomic characteristic from a plurality of agronomic characteristics that limits a yield of a crop, wherein the computing element receives an agricultural prescription comprised of at least one agricultural characteristic and at least one agricultural action, and wherein the agricultural prescription is configured to be transmitted over the wireless network, wherein the agricultural action controls at least one of the motor, actuator, pump, valve, and meter of the agricultural device; and
an information processor in operative communication with computing element, the information processor coupled to at least one sensor configured to gather information pertaining to the agricultural characteristic, wherein the information processor generates further agricultural data associated with the gathered information, and transmits the further agricultural data to the remote server over the wireless network.

24. The agricultural system of claim 23, wherein the computing element receives the agricultural prescription over the wireless network and outputs the at least one agricultural action.

25. The agricultural system of claim 24, wherein the at least one sensor is coupled to the agricultural device.

26. The agricultural system of claim 23, wherein the comprising element is included in a first data processing component.

27. The agricultural system of claim 26, further comprising a second data processing component in communication with the first data processing component, the second data processing component configured to receive the agricultural prescription from the first data processing component, wherein the second data processing component is configured to output the at least one agricultural action.

28. The agricultural system of claim 23, wherein the computing element is configured to generate a second agricultural prescription based on the agricultural data generated by the at least one sensor, and wherein the second agricultural prescription is configured to be transmitted over the wireless network.

29. The agricultural system of claim 28, wherein the agricultural device receives the agricultural prescription and the second agricultural prescription, over the wireless network.

* * * * *